(12) United States Patent
Astolfi Filho et al.

(10) Patent No.: US 6,281,329 B1
(45) Date of Patent: Aug. 28, 2001

(54) VECTOR FOR EXPRESSION OF HETEROLOGOUS PROTEIN AND METHODS FOR EXTRACTING RECOMBINANT PROTEIN AND FOR PURIFYING ISOLATED RECOMBINANT INSULIN

(75) Inventors: Spartaco Astolfi Filho; Beatriz Dolabela de Lima, both of Brasilia; Josef Ernst Thiemann, Montes Claros; Heloisa Ribeiro Tunes de Sousa, Montes Claros; Luciano Vilela, Montes Claros, all of (BR)

(73) Assignees: Biobrás S.A., Monte Claros; Universidade de Brasilia, Brasilia, both of (BR)

( * ) Notice: Subject to any disclaimer, the term of this patent is extended or adjusted under 35 U.S.C. 154(b) by 0 days.

(21) Appl. No.: 09/306,949

(22) Filed: May 7, 1999

Related U.S. Application Data

(62) Division of application No. 08/886,967, filed on Jul. 2, 1997, now Pat. No. 6,068,993.

(51) Int. Cl.[7] .............................. A61K 38/28; C07K 5/00; C07K 7/00; C12P 21/06; C12N 1/20
(52) U.S. Cl. ..................... 530/305; 435/69.1; 435/69.4; 435/70.1; 435/252.3; 435/325; 435/455; 530/303; 530/305
(58) Field of Search .............................. 435/69, 1, 69.4, 435/91.1, 70.1, 91.5, 252.3, 252.8, 320.1; 530/305, 300, 303, 324, 350, 412; 536/23.1, 23.4, 23.5

(56) References Cited

U.S. PATENT DOCUMENTS 6,013,514 * 1/2000 Chong et al. ..................... 435/320.1

* cited by examiner

Primary Examiner—Robert A. Schwartzman
Assistant Examiner—Jane Zara
(74) Attorney, Agent, or Firm—Frommer, Lawrence & Haug LLP; Edgar H. Haug; Thomas J. Kowalski

(57) ABSTRACT

The present invention relates to a vector for expression of a heterologous protein by a Gram negative bacteria, wherein the vector includes a nucleic acid such as DNA encoding the following: an origin of replication region; optionally and preferably a selection marker; a promoter; an initiation region such as translation initiation region and/or a ribosome binding site, at least one restriction site for insertion of heterologous nucleic acid, e.g. DNA, encoding the heterologous protein, and a transcription terminator. The inventive vector may contain DNA encoding the heterologous protein, e.g., pro-insulin such as pro-insulin with a His tag. Additionally, the invention provides a method for extracting a recombinant protein from within a recombinant Gram negative bacteria having a cell membrane, without lysing the bacteria, as well as a method for purifying an isolated recombinant human insulin, wherein the isolated recombinant human pro-insulin is subjected to sulfitolysis, Ni-chelation chromatography, renaturation, limited proteolysis and chromatography separation to provide purified, isolated, recombinant human insulin.

11 Claims, 66 Drawing Sheets

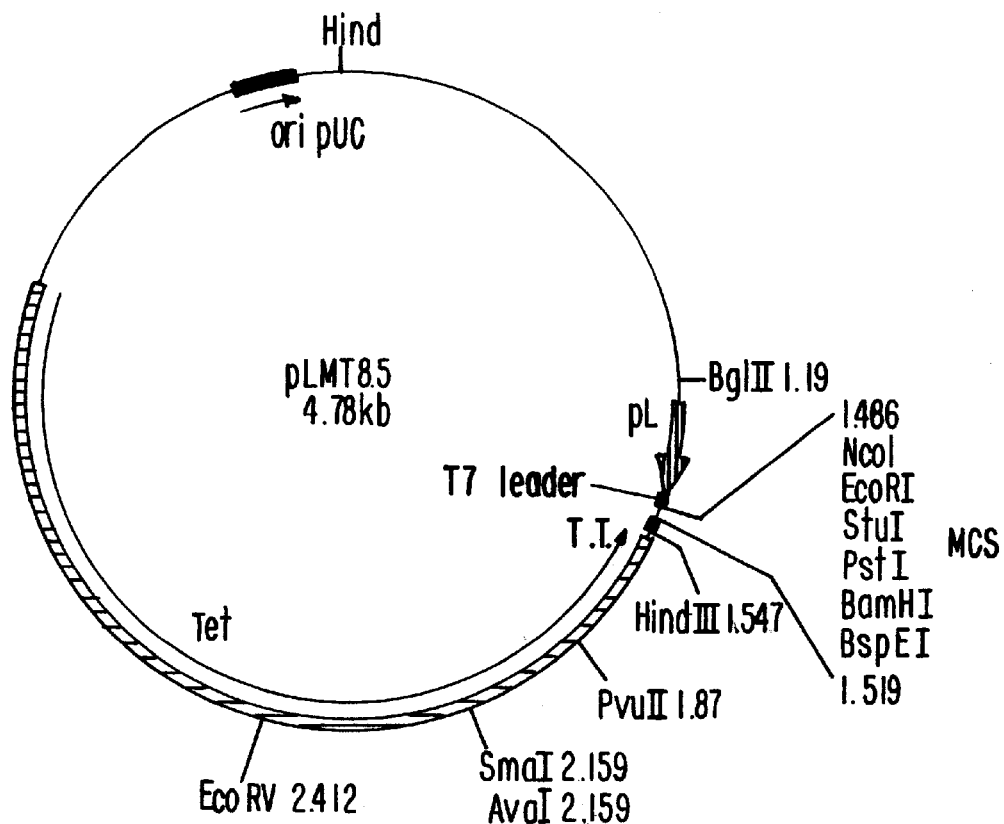
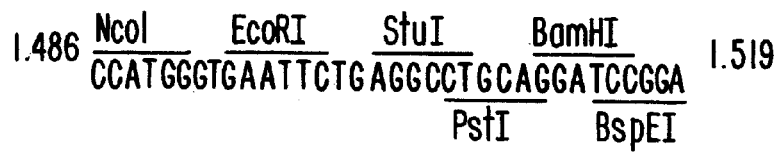
Brief Description of the vector:
1. ori-replication origin of the plasmid pUC8
2. Tet-resistance gene to tetracicline of the plasmid RP4
3. pL-lambda phage promoter
4. T7 leader-Shine Dalgarno region of the T7 phage gene 10
5. MCS-multiple site cloning
6. TT-Rho-indepent transcription termination
FIG. 5A 1 pH 5,5
2 pH 5,5
3 pH 5,0
4 pH 5,0
5 pH 4,5
6 pH 4,5
7 pH 4,0
M MW marker

FIG. 10a-1

Positions of Restriction Endonucleases sites

```
        Eco57 I
          Alu I            Mse I                   Mnl I           Hinf I  Hinf I             Th111 II
        HinD III Mbo II                                                                                                                                    80
          | | |              |                       |               |      |                   |
        AAGCTTCAGTTGAAGATATTAAGAACAGCCTCGCAGATGAGAATCATTGGGATTCCATCTTTTTGTTGTTGAAGGC
        TTCGAAGTCAACTTCTATAATTCTTGTCGGAGCGTCTACTCTTAGTAACCCTAAGGTAGAAAAACAACTTCCG
          | | |              |                       |               |      |                   |

Sau3A I
                                                         Mbo I
                                                         Dpn I
                                  Hae III                                                Mse I
                                  Sau96 I  Fok I                                                                                                          160
                                    ||      |                                              |
        GACACCATTGGTTTGCCAGAACTGTTTCGGGCCGACCATCGATCTGACAGATTTTTAATGGGAAAGGAATGTC
        CTGTGGTAACCAAACGGTCTTGACAAAGCCCGGCTGGTAGCTAGACTGTCTAAAAATTACCCTTTCCTTACAG
                                    ||      |                                              |

Nsi I
                  BstU I                                                                   Nde I
                  HinP I                                           Nla IV                Nsi I
          Mse I    Hha I                                   Mnl I     |                      |                                                             240
            |      ||                                       |        |                      |
        ATTAAGCAGTGAGCGGTTCAGATAGAGCCACTGATGAGGGAACCACCAAAGACGAGTTATGCATATGCATTTCA
        TAATTCGTCACTCGCCAAGTCTATCTCGGTGACTACTCCCTTGGTGGTTTCTGCTCAATACGTATACGTAAAGT
            |      ||                                       |        |                      |
```

FIG. 10a-2

```
Hae III
Gdi II
Eag I                              Alu I                    Mse I   Dde I
Eae I           Hph I                                                            320
|| |             |                   |                        |       |
TCGGCGAACAAGGTGAAGTAGAAGCCAAGCTACCTGTATTTGGCGATATATTAAGGTCTTAGGGCAACAGATATT
AGCCGCTTGTTCCACTTCATCTTCGGTTCGATGGACATAAACCGCTATATAATTCCAGAATCCGTTGTCTATAA

Ple I                Mse I                              Sty I
                 Hinf I               Dra I                              Sec I  400
         Alu I    ||                    ||                                |
GAAGGGAGCTTTTGACTCATTGGATATAGTCATTAAGCCAAAATTTAAAGGGATATAAATTTCCTATATTTTCCAAGGTTGCCAAGGATAT
CTTCCCTCGAAAACTGAGTAACCTATATCAGTAATTCGGTTTTAAATTTCCTATATTTAAAGGATATAAAAGGTTGCCAACGGTTCCTATA Msp I
                                                          Hpa II
         Mnl I                                            Hae III
         Hph I                         Taq I              Mnl I                  Mse I  480
Mse I    Mae III                       |                   |||                     |
TATTTTAACCGTCACCTCAATTTCGACATTAGCCTGGGCAAAGATGAGGCAAAGATTAAACAGAACATTA
ATAAAAATTGGCAGTGGAGTTAAAGCTGTAATCGGACCCGTTTCTACTCCGTTTCTAATTGTCTTGTAAT
```

FIG. 10b-1

```
                                                                            560
                                          HinP I                            |
                                          Hha I                    Hph I
                                          Hae II                   Mae III   Mbo II
                                                                             Ear I
  Hae III      Dde I Mnl I                BstE II     Dde I Alu I   Eco57 I
  Hae I        |   |                      |||         |    |        |
  | |          |   |                      |||         |    |        |
TCTATCAGAAAAGGCCATTCTCAGGCGCCCTCTGAACAAGGTCACCAATGCTGAGATAGCTGAAGAGATGGCATATTGCT
AGATAGTCTTTTCCGGTAAGAGTCCGCGGGAGACTTGTTCCAGTGGTTACGACTCTATCGACTTCTCTACCGTATAACGA
                                                                            640
                                                                            |
                      Mse I                             Ase I
                      Dra I   BspM I          Mse I     Mse I
         Bsr I        |   |   |               |         ||
         |            |   |   |               |         ||
ACGCAAGAATGAAAAGTGATATACTGGAAGTTTAAAAGGCAGTGGCAAAGTTAAGGATTAATATCAGGAGTAATT
TGCGTTCTTACTTTTCACTATATGACCTTCAAATTTTCCGTCACCGTTCAATTATAGTCCTCATTAA
                                                                            720
                                                                            |
  ScrF I
  EcoR II
  Nla III                                     Mae II
  Hinf I BstN I                               |
  |      |                                    |
ATGCGGAACGAATCATGCCTGTGTTACATAGTAATAATTCCTAGTTATGTAAGCATTGCTATCCTTTTCG
TACGCCTTGCTTAGTACGGACCACAAATGTATCATTATTAAGGATCAATACATTCGTAACGATAGGAAAAGC
```

FIG. 10b-2

```
                                                                                         800
                                                         Th111 I   Nde I   Nla IV
  ScrF I                                                                   Nla III
  EcoR II
Xcm I  BstN I                    Alu I
  —      —                         —                       —       —        —
CCACTACTACTTCCTGTGTTTCTTTTTCAGCTCTCATAGAGATGGTCTTGGGCGACATTGTCATCATATGCAGGAACCATGA
GGTGATGATGAAGGACACAAAGAAAAAGTCGAGAGTATCTCTACCAGAACCCGCTGTAACGTAGTATACGTCCTTGGTACT
  ·           ·           ·           ·           ·           ·           ·           ·

Hae III
                                               Bsr I
                                           HinP I  Msc I                              880
                                           Hha I   Hae I
            Fnu4H I                        BstU I  Eae I
            Bbv I   Mae II                   =       =
              —       —                      =       =
TTGCAATCTGATTGCGCTTGAGTTTCTAATCGGAAGCAGAAGCGGCGACTGGCCAAGATTAGAGAGTATGGGTAT
AACGTTAGACTAACGCGAACTCAAAGATTAGCCTTCGTCTTCGCGCTGACCGGTTCTAATCTCTCATACCCATA
  ·           ·           ·           ·           ·           ·           ·
```

```
                    Dde I  ScrF I
                    Mnl I  Nci I                              Sau3A I
                    Hae III  Msp I                            Mbo I
              Msp I      Hpa II                               Dpn I
              Hpa II     Bcn I                                Pvu I
              ScrF I  HinP I
              Nci I   Hha I
Mne I         Bcn I   Hae II                       Mnl I                                   1120
TCCAACTATATAATTGCCAGAGAACAAGAATAACCCGCCTCAGCGCCGGTTTCTTTGCCTCACGATGCGCCCAAA
AGGTTGATATATTAACGGTCTCTTGTTCTTATTGGGCGGAGTCGCGGCCCAAAGAAACGGAGTGCTAGCGGGGTTT
```

```
                                         Hph I                                    Tth111 II
                                         Sau3A I                                        1200
                                         Mbo I
                                         Dpn I
                                         BstY I
                                         Bgl II
AACATAACCAATTGTATTTATTGAAAAATAAATAGATACAACTCACTAAACATAGCAATTCAGATCTCCTACCAAA
TTGTATTGGTTAACATAAATAACTTTTTATTTATTTATCTATGTTGATTGTATCGTTAAGTCTAGAGAGTGATGGTTT
```

FIG. 10c-2

```
                                                                    HgiE II  Hph I                                 HinC II
                                                                    —       —                                      —          1280
CAATGCCCCTGCAAAAAATTCATATATAAAAAACATACAGATATAACCATCTGCGGTGATAATTATCTCGGGGTG
GTTACGGGGACGTTTTTTAATTAAGTATATATTTTTGTATGCTATTGGTAGACGCCACTATTAATAGAGACCCCAC

Mae III
                                                                              Hph I
              HgiA I                                                                   Nla III  Hga I  Mse I
              Bsp1286 I                                                                —        —     —            1360
         Bsr I    Dde I                             Hga I
         —        —                                 —
         HgiE II Hph I
TTGACATAAATACCACTGCGGTGATATACTGAGCACATCAGCAGCCACTGACCACCATGAAGTGACGCTCTAAAAA
AACTGTATTTATGGTGACGCCACTATATGACTCGTGTAGTCGTCGGTGACTGGTGGTACTTCCACTGCGAGATTTTT

Hae III
                                                                                        Gdi II
        Mbo II       Bsm I                                                              Eae I
        EcoN I       Fnu4H I                                                            —          1440
        —            —                                                                  —
Mse I   Eco57 I      Bbv I
—       —            —
TTAAGCCCTGAAGAAGGCAGCATTCAAAGCAGAAGGCTTTGGGTGTGATACGAAACGAAGCATTGGCGTAAGTGC
AATTCGGGACTCTTCCGTCGTAAGTTTCGTCTTCCGAAACCCACACTATGCTTTGCTTCGTAACGGCATTCACG
```

```
                                                                                             Msp I
                                                                                             Nae I
                                                                                             Cfr10 I
                                                                                             HinP I
                                                                                             Hha I
                                                            ScrF I                           Hae II
                                                            EcoR II                          Fnu4H I
                                             BstX I                          Bbv I    Bsm I
  Fnu4H I                                                   BstN I           Tth111 II Hpa II  SfaN I
  Bbv I
  Alu I  ScrF I
  Pvu II EcoR II
  NspB II
  Fnu4H I            Fok I
Bsr I  Bbv I  Sec I  Mnl I  BspM I
 |     ||||   ||     |      |        |       |     ||   |||                  1840
 CCAGTGAGCTTGCAGCTGGGTTCCTGACAGTCTTGACACATTGCTTGCAGCGGCGCATTCCGATG
 GGTCACTCGAACGTCGACCCAAGGACTGTCAGAACTGTGTAACGAACGTCGCCGCGTAAGGCTAC
 |     ||||   ||     |      |        |       |     ||   |||
                     |      |        |
                     Sau3A I
                     Mbo I
                     Nla III
              Sau96 I
              Ava I   Dpn I   Fok I            Fok I
  Tth111 II                   Fok I   BstU I   Fok I
                              Nru I   Tth111 II
 |         |       |      |   ||      ||       |                             1920
 CCACCCGAAGCAGGACCATGATGGGAAGGCCATCATCCCGTGCCAAGCAGGATGTAGCCTGTGCC
 GGTGGGCTTCGTCCTGGTACTAGCCCTTCCGGTAGTAGGGCACGGTTCGTCCTACATCGGACACG
 |         |       |      |   ||      ||       |
```

FIG. 10e-2

```
                                                                    Sau3A I
                                                                    Mbo I
                                                                    Dpn I
                                                                    Bcl I       Sec I
                                                                    Hph I       ScrF I
                                              Fnu4H I    Msp I      EcoR II
                                                         Hpa II     BstN I
                                    ScrF I               Cfr10 I
                                    Nci I                Hae III
                                    Msp I                Sau96 I
                                    Hpa II
                                    Bcn I
Bsp1286 I
Nla III
``` positions ~2000 and ~2080

FIG. 10f-1

```
Msp I
Hpa II
Nae I
Cfr10 I                                                                                    Xma I
Hae III                                                                                    Sma I
Gdi II                                                                                     Sec I
Eag I                                                                                      ScrF I
Eae I                                                                                      Nci I
Fnu4H I                                                                                    Bcn I
BstU I                                                    Mbo II                            Ava I
HinP I  Nla IV                                            Mbo II  Bgl I                     Sec I
Hha I   Ban I   Mme I                    Nla III  Bbv II          Fnu4H I  Nla III
  ||||  ||      |                         |        |               |       |                |
ACCCAAAGCGGCGGCCACCTGTCGACAAGTTCGATGATGAAGAGACCGCCATCAGGCGGCGACGGTCATGCC 2160
TGGGTTTCGCCGCCGGTGGACAGCTGTTCAAGCTACTACTTCTCTGGCGGTAGTCCGCCGCTGCCAGTACGG
  ||||  ||      |                         |        |               |       |                |
```

FIG.10f-2

```
                                              Msp I
                                              Hpa II
                                              Nae I                    Msp I
                                              Cfr10 I                  Hpa II
                                              Hae III                  Ple I
                            Msp I             Gdi II                   Hinf I
                            Hpa II            Eag I
                            ScrF I            Eae I
                            Nci I
           Dde I            Bcn I
           Esp I            Mnl I   Mae III                                                2240
  Sau96 I  Alu I            |       |                                                      |
  Hae III  |||              |||     |                                                      |
  Sau96 I                                                                                  |
  Nla IV
  Bsp1286 I
  Ban II
  Apa I
  ScrF I
  Nci I
  Msp I
  Hpa II
  Bcn I
  |||
CGGGCCCACCGAAGCTGAGCGGGTTGAGAGCCTCCGGGTAACGGCGGTTGCGCTTGTGCGACTCGGCA
GCCCGGGTGGCTTCGACTCGCCCAACTCTCGGAGGCCCATTGCCGCCAACGCGAACGCGTGAGCCGT
  |||         |||                 ||||               ||||            |
```

FIG. 10f-3

```
                                                    Mbo II
                    Fnu4H I
                    BstU I
                    Sec I
                    Sac II
                    NspB II
                    Dsa I
                    Fnu4H I
          Hae III   Bbv I
          Mnl I     Fnu4H I
```

2320
AAAGGAAACAGCCGTCAGGAAATTGAGGCGTCAAGGCTGCCGGGGAAGAACGGAGGTGGGGAGAAACGCCC
TTTCCTTTGTCGGCAGTCCTTTAACTCCGCAGTTCCGACGGCCCCTTCTTGCCTCCACCCCCTCTTTGCGGG

FIG. 10g-1

```
                                                                              HinP I
                                                                              Hha I
                                                                              BstU I
                                                                              HinP I
                                                                              Hha I
                                                                              BssH II
                                                                              BstU I
                                                                              HinP I
                                                                              Hha I
                                                                              BssH II
                                                       Nla III                BstU I
                                                       BspH I                 Fnu4H I
                                                       HinP I
                                                       Hha I
                                                       Hae II
                        Sau96 I
                        Nla IV
                        Ava II
                        PpuM I
                        EcoO109 I
             HgiA I
             Bsp1286 I  BstU I     Fok I                                          2400
ATCAGCCCACCGAGCACAGGTCCCGACCATCCGAAACAGGGCTCATGAAGCCGAAACCGGAAGTGCGGCGGCTC
TAGTCGGGTGGCTCGTGTCCAGGGCTGGTAGGCTTTGTCCCGAGTACTTCGGCTTCACGCCGCCGCCGAG
```

```
                                                                    Gdi II
                                         Hae III                    Eae I    2560
                                         Gdi II
                                         Eae I
                                         Msp I
                                         Hpa II
                                         Nae I
                                         Cfr10 I
                                         HinP I
                                         Hha I
                                         Nla IV
                                         Nar I
                                         Hae II
                                         Bbe I
                               Taq I     Ban I
                               Sal I     Aha II                  BsmA I
              HinP I           HinC II   ||||                      |
              Hha I   Nla III  Acc I     ||||                      |
              Hae II Bgl I     ||        ||                        |
              ||     |         ||        ||       •              • |    •
TATAGAGAACCCAAAGGAAAGGCGCTGTGCCATGATGGCCAGGTAGTGCCGGCGCCAGGAGCGAGCAAGATT
ATATCTCTTGGGTTTCCTTTCCGCGACACGGTACTACCGGTCCATCACGGCCGCGGTCCATCACGGCCGCGGTCGTTCTAA
        •              •              •              •              •
```

```
                                                                                                    2880
         Hinf I
         BstU I
Sau96 I  HinP I
Ava II   Hha I
NspB II  BstU I
CTCCGCTGGTCGTCGGGATTGAACCCGGATCTTATCACTGATAAGTTGGTGGACATATTAGTTTATCAGTGATAAGTG
GAGGCGACCAGCAGCCCTAACTTGGGCCTAAGAATAGTGACTATTCAACCACCTGTATAATCAAATAGTCACTATTTCAC Sau3A I
                            Mbo I
                            Dpn I     Mae I
Nla III  Fnu4H I            Alw I     Fnu4H I       Mnl I     Acc I                                 2960
Th111 II Bbv I
TCAAGCATGACAAAGTTGCACCCGAATACAGTCGTGCCCTAGACGTATCGTTGAACGAGGTGGGCGTAGACGGTCT
AGTTCGTACTGTTTCAACGTGGGCTTATGTCAGCACGGGATCTGCATAGCAACTTGCTCCACCCGCATCTGCCAGA
```

```
                                                                              3280
HinP I                                                                         |
Hha I   Hae III                                                       Sec I
        Gdi II  Fnu4H I                                               ScrF I
        Eag I   Hga I  Alu I                                          Nci I
        Eae I   Hinp I Bbv I                                          Msp I
                Hha I  BstU I                      Mnl I Mnl I        Hpa II
                |      |      |                    |     |            Bcn I
                |      |      |                    |     EcoN I       Hae III
                |      |      |                    |     |            Gdi II  Tth111 I
                |      |      |                    |     |            Eag I   Hga I
                |      |      |                    |     |            Eae I   Aha II
                |      |      |                    |     |            |       |
GGGCGCACGGCAGATGGAAACGGCGGACGCAGCTTCGCTCTGGAGGCGGGTTTTTCGGGGACGCCGTCA
CCCGCGTGCCGTCTACCTTTGCCGCCTGCGTCGAAGCGAGACCTCCGCCCAAAAAGCCCCTGCGGCAGT
```

```
                BstU I                                                                           Sau96 I
                Ple I   Hph I                                           Mnl I           Mae II   Ava II
Taq I           Hinf I                          Taq I                     |               |        |
  |               |                               |                       |               |        |
AGCGTTCGAGCAGGACTGCGGTGATGATTGGGATTGTCAGGAAGGAGGCTGTGTCAGGAAGTTGAAGGACCGA   3520
TCGCAAGCTCGTCCTGACGCCACTACTAACCCTAACAGTCCTTCCGACACAGTCCTTCAACTTCCTGGCT
                                                            ·                     ·                ·
              Sau96 I
              Ava II    Msp I
              Sau3A I   Hpa II
              Mbo I     Fnu4H I
Mae III       Dpn I    Bbv I   HinP I                                     Acc I             Mnl I
Hph I         Bcl I    NspB II Hha I                                      Nla III   Fok I
  |             |        |      |                                           |         |       |
GAAAGGGTGACGATTGATCAGGACCCGCCGAGCGCCAACCACTACAGACCATGTAGACACATCCCTC    3600
CTTTCCCACTGCTAACTAGTCCTGGGCGGCTCGCGGTTGGTGATGTCTGGTACATCTGTGTAGGGAG
                                                            ·                     ·                ·
              Bsp1286 I
              Ban II           HinP I                                                          Fnu4H I
Hga I                          Hha I                              Hga I                         BstU I
BstU I                         Hae II                             Mae I       Mnl I
  |                              |                                  |           |                 |
CCCTTTCCACGGTCAGAGCCCGGCCTAGCGCCCTAGCGGTCCTTTCATGCCTCAAGCCTTCACGCC    3680
GGGAAAGGTGCCAGTCTCGGGCCGGATCGCGGGATCGCCAGGAAAGTACGGAAGTTCGGAAGTGCGG
                                                      Nla III    Mae I        Mnl I
```

```
                                                                              Taq I
                                                                              Sal I
                                                                              HinC II
                                                                              Acc I
                    Gdi II                                              Sau3A I
                Sec I  Hae III                                           Mbo I
                ScrF I                                                   Dpn I
                EcoR II  Mbo II                              HinP I      Alw I
                BstN I   Bbv II                              Hha I       BstY I
         Sau96 I  Eag I                                      Fsp I
         Mnl I    Eae I
  HinP I
  Hha I
  Hae II         BstU I  Ava II  Fnu4H I       Mae II
```

TCGTGCGCTGGCGGCTGCAGGGCGGGGCGTCCAGGGCGAGTCCTTGCCTTCAGTTCTGCCGCTGGCCAGATGAGATAGATCCGTCGA 3840
AGCACGCGACCGCCGACGTCCCGCCCCGCAGGTCCCGCTCAGGAACGGACGGTCGTACTCTATCGAGGCAGCT

```
                Sau3A I
          Mae I Mbo I
          Sau3A I Dpn I
          Mbo I  Alw I
          Dpn I  BstY I
          BstY I Mbo II                                  Nla III              Mae II         Hga I
          Alw I  Hph I                                   BspH I               Mse I          Dde I
```

CCAAAAGGATCTAGGTGAAGATCCTTTTTGATAATCTCATGACCAAAATCCCTTAACGTGAGTTTTCGTTCCACTGAGCG 3920
GGTTTTCCTAGATCCACTTCTAGGAAAACTATTAGAGTACTGGTTTTAGGGAATTGCACTCAAAAGCAAGGTGACTCGC

FIG. 10k-3

```
                                                                                                    4000
              Sau3A I                                              Tth111 II
              Mbo I      Sau3A I                          BstU I
              Dpn I      Mbo II   Mbo I                   HinP I   Fnu4H I
   Sau3A I    Mbo I      Dpn I    Dpn I                   Hha I    Bbv I   Tth111 II
   Mbo I  BstY I         Alw I    Alw I
   Dpn I  Alw I          BstY I   BstY I
     |  |  |               ||       ||                      |||      |     ||
TCAGACCCGTAGAAAAGATCAAAGATCTTGAGATCTTCTTGAGATCTTGCGGTAATCGCTTGCAAACAAAAAA
AGTCTGGGCCATCTTTTCTAGTTTCTAGAAGAACTCTAGAAGAACTCTAGAACGCCATTAGCGAACGTTTGTTTTTT
                  ||       ||
                  Sau3A I
                  Mbo I
                  Dpn I
                  Alw I
              Msp I
              Hpa II                Alu I
   NspB II    Tth111 II              |
   HgiE II      |                                                           4080
     |                                                    Eco57 I
                                                          Bsr I           HinP I
                                                          Mae III         Hha I
                                                            |               ||
ACCACCGGCTACCAGGGTGGTTGTTGCCGGATCAAGAGCTACCAACTCTTTTTCCGAAGTAACTGGCTTCAGCAGAG
TGGTGGCCGATGGTCCCACCAACAACGGCCTAGTTCTCGATGGTTGAGAAAAAGGCTTCATTGACCGAAGTCGTCTC
```

```
Dde I         HinP I                              Msp I  Fnu4H I
              Hha I                               Hpa II
              Hae II
 |             ||                                   ||
AACTGAGATACTACAGGCGTGAGCATTGAGAAAGGCCAGCGTTCCGAAGCGAGAAAGGCGGACAGTATCCGGTAAGC    4400
TTGACTCTATGATGTCCGCACTGTAACTCTTTCCGGTCGCAAGGCTTCGCTCTTTCCGCCTGTCATAGGCCATTCG
 |                                                  |             |
Mme I                Sec I
                     ScrF I
            Mnl I    EcoR II          ScrF I
            HinP I   BstN I           EcoR II
            Hha I    Alu I            BstN I
             |        ||               |
GGCAGGGGTGGAACAGAGAGGCACGAGGGAGCTTCCAGGGGAAACGCCTGTATCTTTATAGTCCTGTGGGTTTCG    4480
CCGTCCCCACCTTGTCTCTCCGTGCTCCCTCGAAGGTCCCCTTTGCGGACATAGAAATATCAGGACACCCAAAGC
                                        |
```

FIG. 101-3

```
                                                            Hae III
                                                            Fnu4H I
                Drd I  Taq I                                BstU I
                    Hga I                                   |||
          Mnl I Hae III        SfaN I       Nla IV                    4560
            |    |  |            |            |              ||
     CCACCTCGACTTGAGGGTCGATTTTGTATGCGAGGGGGGGAGCCTATGCGAAAAACGCCAGCAACGCGCCT
     GGTGGAGACTGAACTCCAGCTAAAAACATACGCTCCCCCCCTCGGATACGCTTTTTGCGGTCGTTGCGCGGA
                     ScrF I                 Nla III
                     EcoR II                NspH I
                     BstN I Hae III         Nsp7524 I
                     |      Hae I           Afl III
          Nla IV     ||     ||              |||

Hinf I
                                                     |                4640
     TTTTACGTTCCTGGCCTTTGCTGGCCTTTTGCTCCTCACATGTCTTCTCCGGTTATCCCGATTCTGTGGATAACCGT
     AAAATGCAAGGACCGGAAACGACCGGAAAACGAGGAGTGTACAGAAGAGGCAATAGGGCTAAGACACCTATTGGCA
```

FIG. 10m-1

```
         Alu I   Fnu4H I              Fnu4H I                    Fnu4H I                    Ple I
                 Bbv I                Bbv I                      Bbv I                      Mbo II
                                                                 HinP I          Mnl I      Ear I
                                                                 Hha I   Hinf I
ATTACCGCCTTTGAGTGAGCTGATACCGCTCGCCGCAGCCGAACGACCGAGCGCAGCGAGTCAGTGAGCGAGGAAGCGGA   4720
TAATGGCGAAACTCACTCGACTATGGCGAGCGGCGTCGGCTTGCTGGCTCGCGTCGCTCAGTCACTCGCTCCTTCGCCT
   •           •           •           •           •           •           •
```

```
  HinP I                          BstU I   HinP I   Mse I
  Hha I                           Gdi II   Hha I    Hinf I
  Hae II              Mnl I       Eae I    BstU I   Hae III   Ase I
AGAGCGCCCAATAGCGCAAACCGCCTCTCCCCGCGGTTGGCCGATTCATTAATGCAGAATT   4781
TCTCGCGGGTTATCGCGTTTGGCGGAGAGGGGCGCCAACCGGCTAAGTAATTACGTCTTAA
   •           •           •           •           •           •
```

FIG. 10m-2

Restriction Endonucleases site usage

| Enzyme | Count | Enzyme | Count | Enzyme | Count |
|---|---|---|---|---|---|
| Aat II | 1 | BspH I | 2 | EcoR V | 1 | 
| Acc I | 4 | BspM I | 2 | Esp I | 1 |
| Afl II | – | BspM II | 3 | Fnu4H I | 51 |
| Afl III | 1 | Bsr I | 14 | Fok I | 9 |
| Aha II | 5 | BssH II | 6 | Fsp I | 2 |
| Alu I | 17 | BstB I | – | Gdi II | 12 |
| Alw I | 13 | BstE II | 1 | Gsu I | – |
| AlwN I | 3 | BstN I | 9 | Hae I | 7 |
| Apa I | 1 | BstU I | 34 | Hae II | 20 |
| ApaL I | 1 | BstX I | 1 | Hae III | 35 |
| Ase I | 2 | BstY I | 7 | Hga I | 15 |
| Asp718 | – | Bsu36 I | – | HgiA I | 4 |
| Ava I | 1 | Cfr10 I | 14 | HgiE II | 3 |

| Enzyme | Count | Enzyme | Count |
|---|---|---|---|
| Mme I | 6 | Rsr II | 1 |
| Mnl I | 35 | Sac I | – |
| Msc I | 1 | Sac II | 2 |
| Mse I | 18 | Sal I | 2 |
| Msp I | 34 | Sau3A I | 26 |
| Nae I | 11 | Sau96 I | 18 |
| Nar I | 1 | Sca I | – |
| Nci I | 11 | ScrF I | 20 |
| Nco I | 1 | Sec I | 12 |
| Nde I | 2 | SfaN I | 7 |
| Nhe I | – | Sfi I | – |
| Nla III | 19 | Sma I | 1 |
| Nla IV | 15 | SnaB I | – |

FIG. 10m-3

| Count | Enzyme | Count | Enzyme | Count | Enzyme | Count | Enzyme |
|---|---|---|---|---|---|---|---|
| 10 | Ava II | – | Cla I | 52 | Hha I | – | Not I |
| – | Avr II | 11 | Dde I | 3 | HinC II | 1 | Nru I |
| 1 | BamH I | 26 | Dpn I | 2 | HinD III | 3 | Nsi I |
| 4 | Ban I | 2 | Dra I | 13 | Hinf I | 1 | Nsp7524 I |
| 2 | Ban II | – | Dra III | 52 | HinP I | 8 | NspB II |
| 1 | Bbe I | 1 | Drd I | – | Hpa I | 1 | NspH I |
| 24 | Bbv I | 3 | Dsa I | 34 | Hpa II | – | PaeR7 I |
| 2 | Bbv II | 13 | Eae I | 15 | Hph I | 6 | PflM I |
| 2 | Bcl I | 6 | Eag I | – | Kpn I | – | Ple I |
| 11 | Bcn I | 3 | Ear I | 5 | Mae I | 1 | Rnl I |
| 4 | Bgl I | – | Eco47 III | 8 | Mae II | 1 | PpuM I |
| 1 | Bgl II | 6 | Eco57 I | 9 | Mae III | 4 | Pst I |
| – | BsaA I | 2 | EcoN I | 26 | Mbo I | 1 | Pvu I |
| 6 | Bsm I | 1 | EcoO109 I | 11 | Mbo II | – | Pvu II |
| 1 | BsmA I | 1 | EcoR I | – | Mlu I | – | Rsa I |
| 7 | Bsp1286 I | 9 | EcoR II | | | | |

| Count | Enzyme |
|---|---|
| – | Spe I |
| – | Sph I |
| – | Spl I |
| – | Ssp I |
| 1 | Stu I |
| 2 | Sty I |
| 11 | Taq I |
| 3 | Tth111 I |
| 10 | Tth111 II |
| – | Xba I |
| – | Xca I |
| 1 | Xho I |
| – | Xcm I |
| 1 | Xma I |
| – | Xmn I |

FIG.11a-1

| Enzyme | Site | Use | Site position | (Fragment length) | Fragment order |
|---|---|---|---|---|---|
| Aat II | gacgt/c | 1 | 1( 2658) | 2659( 2123) | 2 |
| Afl III | a/crygt | 1 | 1( 4596) | 4597( 185) | 2 |
| Apa I | gggcc/c | 1 | 1( 2162) | 2163( 2619) | 1 |
| ApaL I | g/tgcac | 1 | 1( 4282) | 4283( 499) | 2 |
| Ava I | c/ycgrg | 1 | 1( 2159) | 2160( 2622) | 1 |
| BamH I | g/gatcc | 1 | 1( 1510) | 1511( 3271) | 1 |
| Bbe I | ggcgc/c | 1 | 1( 2532) | 2533( 2249) | 2 |
| Bgl II | a/gatct | 1 | 1( 1181) | 1182( 3600) | 1 |
| BsmA I | gtctc 1/5 | 1 | 1( 2545) | 2546( 2236) | 2 |
| BstE II | g/gtnacc | 1 | 1( 519) | 520( 4262) | 1 |
| BstX I | ccannnnn/ntgg | 1 | 1( 1796) | 1797( 2985) | 1 |
| Drd I | gacnnnn/nngtc | 1 | 1( 4488) | 4489( 293) | 2 |
| EcoO109 I | rg/gnccy | 1 | 1( 2337) | 2338( 2444) | 1 |
| EcoR I | g/aattc | 1 | 1( 1493) | 1494( 3288) | 1 |
| EcoR V | gat/atc | 1 | 1( 2412) | 2413( 2369) | 2 |
| Esp I | gc/tnagc | 1 | 1( 2178) | 2179( 2603) | 1 |
| Msc I | tgg/cca | 1 | 1( 854) | 855( 3927) | 1 |
| Nar I | gg/cgcc | 1 | 1( 2532) | 2533( 2249) | 2 |
| Nco I | c/catgg | 1 | 1( 1485) | 1486( 3296) | 1 |
| Nru I | tcg/cga | 1 | 1( 1889) | 1890( 2892) | 1 |
| Nsp7524 I | r/catgy | 1 | 1( 4596) | 4597( 185) | 2 |

FIG. 11a-2

| | | | | | | |
|---|---|---|---|---|---|---|
| NspH I | rcatg/y | 1 | 1( 4595) 1 | 4597( 185) 2 | | |
| PpuM I | rg/gwccy | 1 | 1( 2337) 2 | 2338( 2444) 1 | | |
| Pst I | ctgca/g | 1 | 1( 1505) 2 | 1506( 3276) 1 | | |
| Pvu II | cag/ctg | 1 | 1( 1773) 2 | 1774( 3008) 1 | | |
| Rsr II | cg/gwccg | 1 | 1( 3428) 1 | 3429( 1353) 2 | | |
| Sma I | ccc/ggg | 1 | 1( 2159) 2 | 2160( 2622) 1 | | |
| Stu I | agg/cct | 1 | 1( 1501) 2 | 1502( 3280) 1 | | |
| Xcm I | ccannnn/nnnntgg | 1 | 1( 720) 2 | 721( 4061) 1 | | |
| Xma I | c/ccggg | 1 | 1( 2159) 2 | 2160( 2622) 1 | | |
| Ase I | at/taat | 2 | 1( 620) 2 | 621( 4147) 1 | 4768( 14) 3 | |
| Ban II | grgcy/c | 2 | 1( 2162) 1 | 2163( 1456) 2 | 3619( 1163) 3 | |
| Bbv II | gaagac 2/6 | 2 | 1( 2124) 1 | 2125( 1674) 2 | 3799( 983) 3 | |
| Bcl I | t/gatca | 2 | 1( 1982) 1 | 1983( 1552) 2 | 3535( 1247) 3 | |
| BspH I | t/catga | 2 | 1( 2372) 1 | 2373( 1504) 2 | 3877( 905) 3 | |
| BspM I | acctgc 4/8 | 2 | 1( 600) 3 | 601( 1198) 2 | 1799( 2983) 1 | |
| Dra I | ttt/aaa | 2 | 1( 365) 2 | 366( 227) 3 | 593( 4189) 1 | |
| EcoN I | cctnn/nnnagg | 2 | 1( 1366) 3 | 1367( 1876) 1 | 3243( 1539) 2 | |
| Fsp I | tgc/gca | 2 | 1( 2601) 1 | 2602( 1214) 2 | 3816( 966) 3 | |
| HinD III | a/agctt | 2 | 1( 0) 3 | 1( 1547) 2 | 1548( 3234) 1 | |
| Nde I | ca/tatg | 2 | 1( 227) 3 | 228( 555) 2 | 783( 3999) 1 | |
| Sac II | ccgc/gg | 2 | 1( 2282) 1 | 2283( 1454) 2 | 3737( 1045) 3 | |
| Sal I | g/tcgac | 2 | 1( 2523) 1 | 2524( 1312) 2 | 3836( 946) 3 | |
| Sty I | c/cwwgg | 2 | 1( 390) 3 | 391( 1095) 2 | 1486( 3296) 1 | |

FIG.11a-3

| | | | | | | | | |
|---|---|---|---|---|---|---|---|---|
| AlwN I | cagnnn/ctg | 3 | 1( 1655) 1 | 1656( 1492) 2 | 3148( 1035) 3 | 4183( 599) 4 | | |
| BspM II | t/ccgga | 3 | 1( 1513) 1 | 1514( 1276) 3 | 2790( 642) 4 | 3432( 1350) 2 | | |
| Dsa I | c/crygg | 3 | 1( 1485) 1 | 1486( 797) 4 | 2283( 1454) 2 | 3737( 1045) 3 | | |
| Ear I | ctcttc 1/4 | 3 | 1( 541) 3 | 542( 1175) 2 | 1717( 3002) 1 | 4719( 63) 4 | | |
| HgiE II | accnnnnnggt | 3 | 1( 1247) 2 | 1248( 44) 4 | 1292( 2718) 1 | 4010( 772) 3 | | |
| HinC II | gty/rac | 3 | 1( 1279) 2 | 1280( 1244) 3 | 2524( 1312) 1 | 3836( 946) 4 | | |
| Nsi I | atgca/t | 3 | 1( 224) 3 | 225( 6) 4 | 231( 796) 2 | 1027( 3755) 1 | | |
| Tth111 I | gacn/nngtc | 3 | 1( 771) 3 | 772( 1953) 1 | 2725( 546) 4 | 3271( 1511) 2 | | |
| Acc I | gt/mkac | 4 | 1( 2523) 1 | 2524( 426) 4 | 2950( 634) 3 | 3584( 252) 5 | | |
| | | | 3836( 946) 2 | | | | | |
| Ban I | g/gyrcc | 4 | 1( 2095) 1 | 2096( 437) 4 | 2533( 554) 3 | 3087( 277) 5 | | |
| | | | 3364( 1418) 2 | | | | | |

FIG.11b-1

| | | | | | | | | | |
|---|---|---|---|---|---|---|---|---|---|
| Bgl I | gccnnnn/nggc | 4 | 1( 2131) 1 | 2132( 378) 5 | 2510( 548) 4 | 3058( 630) 3 |
| | | | 3688( 1094) 2 | | | |
| HgiA I | gwgcw/c | 4 | 1( 1309) 2 | 1310( 1022) 3 | 2332( 412) 5 | 2744( 1539) 1 |
| | | | 4283( 499) 4 | | | |
| Pvu I | cgat/cg | 4 | 1( 1106) 2 | 1107( 479) 3 | 1586( 148) 5 | 1734( 303) 4 |
| | | | 2037( 2745) 1 | | | |
| Aha II | gr/cgyc | 5 | 1( 2532) 1 | 2533( 126) 6 | 2659( 612) 3 | 3271( 141) 5 |
| | | | 3412( 309) 4 | 3721( 1061) 2 | | |
| Mae I | c/tag | 5 | 1( 1446) 2 | 1447( 1479) 1 | 2926( 734) 3 | 3660( 191) 6 |
| | | | 3851( 253) 5 | 4104( 678) 4 | | |
| Bsm I | gaatgc 1/-1 | 6 | 1( 1380) 2 | 1381( 449) 5 | 1830( 173) 6 | 2003( 7) 7 |
| | | | 2010( 630) 3 | 2640( 489) 4 | 3129( 1653) 1 | |
| BssH II | g/cgcgc | 6 | 1( 2390) 1 | 2391( 2) 6 | 2393( 193) 5 | 2586( 587) 3 |
| | | | 3173( 2) 7 | 3175( 575) 4 | 3750( 1032) 2 | |
| Eag I | c/ggccg | 6 | 1( 241) 5 | 242( 1849) 1 | 2091( 118) 6 | 2209( 1012) 2 |
| | | | 3221( 42) 7 | 3263( 531) 4 | 3794( 988) 3 | |
| Eco57 I | ctgaag 16/14 | 6 | 1( 3) 7 | 4( 536) 5 | 540( 828) 3 | 1368( 1650) 1 |
| | | | 3018( 123) 6 | 3141( 929) 2 | 4070( 712) 4 | |
| Mme I | tccrac 20/18 | 6 | 1( 1040) 2 | 1041( 688) 3 | 1729( 375) 5 | 2104( 475) 4 |
| | | | 2579( 1644) 1 | 4223( 184) 7 | 4407( 375) 6 | |
| Ple I | gagtc 4/5 | 6 | 1( 335) 5 | 336( 1895) 1 | 2231( 1115) 2 | 3346( 109) 6 |
| | | | 3455( 772) 3 | 4227( 471) 4 | 4698( 84) 7 | |

FIG.11b-2

| | | | | | | |
|---|---|---|---|---|---|---|
| Bsp1286 I gdgch/c | 7 | 1( 1309) 1 | 1310( 634) 4 | 1944( 219) 7 | 2163( 169) 8 | |
| | | 2332( 412) 6 | 2744( 875) 2 | 3619( 664) 3 | 4283( 499) 5 | |
| BstY I r/gatcy | 7 | 1( 1181) 2 | 1182( 329) 4 | 1511( 2319) 1 | 3830( 17) 6 | |
| | | 3847( 12) 7 | 3859( 86) 5 | 3945( 11) 8 | 3956( 826) 3 | |
| Hae I wgg/ccw | 7 | 1( 492) 4 | 493( 362) 6 | 855( 647) 3 | 1502( 1283) 2 | |
| | | 2785( 1336) 1 | 4121( 452) 5 | 4573( 11) 8 | 4584( 198) 7 | |
| SfaN I gcatc 5/9 | 7 | 1( 1009) 2 | 1010( 19) 8 | 1029( 808) 3 | 1837( 621) 4 | |
| | | 2458( 261) 7 | 2719( 460) 5 | 3179( 1331) 1 | 4510( 272) 6 | |
| Mae II a/cgt | 8 | 1( 686) 5 | 687( 137) 7 | 824( 862) 3 | 1686( 974) 1 | |
| | | 2660( 120) 8 | 2780( 726) 4 | 3506( 299) 6 | 3805( 91) 9 | |
| NspB II cmg/ckg | 8 | 1( 1773) 1 | 1774( 509) 5 | 2283( 520) 4 | 2803( 588) 2 | |
| | | 3391( 153) 9 | 3544( 193) 8 | 3737( 275) 6 | 4012( 245) 7 | |
| | | 3896( 886) 2 | | | | |
| | | 4257( 525) 3 | | | | |

FIG. 11b-3

| Enzyme | Sequence | | | Positions (length) rank |
|---|---|---|---|---|
| BstN I | cc/wgg | 9 | 1( 658) 3<br>1804( 188) 6<br>4450( 121) 7 | 659( 72) 8<br>1992( 1796) 1<br>4571( 211) 5 | 731( 1051) 2<br>3788( 649) 4 | 1782( 22) 9<br>4437( 13)10 |
| EcoR II | /ccwgg | 9 | 1( 658) 3<br>1804( 188) 6<br>4450( 121) 7 | 659( 72) 8<br>1992( 1796) 1<br>4571( 211) 5 | 731( 1051) 2<br>3788( 649) 4 | 1782( 22) 9<br>4437( 13)10 |
| Fok I | ggatg | 9/13 9 | 1( 120) 7<br>1876( 4)10 | 121( 909) 2<br>1880( 25) 9 | 1030( 764) 4<br>1905( 445) 5 | 1794( 82) 8<br>2350( 830) 3 |
| Mae III | /gtnac | 9 | 1( 412) 7<br>2205( 452) 6<br>3180( 412) 6<br>4178( 63)10 | 413( 108) 9<br>2657( 870) 1<br>3592( 1190) 1<br>4241( 541) 4 | 521( 824) 3<br>3527( 535) 5 | 1345( 860) 2<br>4062( 116) 8 |
| Ava II | g/gwcc | 10 | 1( 1726) 1<br>2793( 15)11<br>3541( 204) 6 | 1727( 130) 7<br>2808( 622) 3<br>3745( 40) 9 | 1857( 482) 4<br>3430( 84) 8<br>3785( 997) 2 | 2339( 454) 5<br>3514( 27)10 |
| Tth111 II | caarca | 11/9 10 | 1( 66) 7<br>1851( 48) 8<br>3984( 6)11 | 67( 1130) 1<br>1899( 983) 2<br>3990( 33)10 | 1197( 619) 5<br>2882( 438) 6<br>4023( 759) 3 | 1816( 35) 9<br>3320( 664) 4 |
| Bcn I | ccs/gg | 11 | 1( 1074) 1<br>2160( 1)12 | 1075( 13)11<br>2161( 38)10 | 1088( 875) 3<br>2199( 253) 6 | 1963( 197) 8<br>2452( 241) 7 |

FIG. 11c-1

| Enzyme | Site | | | | | | | | | | | | | |
|---|---|---|---|---|---|---|---|---|---|---|---|---|---|---|
| Dde I | c/tnag | | 11 | 2693 | (506) 5 | 3199 | (67) 9 | 3266 | (953) 2 | 4219 | (563) 4 |
| | | | | 1 | (301) 7 | 302 | (200) 9 | 502 | (29)12 | 531 | (377) 6 |
| | | | | 908 | (173)11 | 1081 | (227) 8 | 1308 | (191)10 | 1499 | (681) 2 |
| | | | | 2180 | (567) 3 | 2747 | (1167) 1 | 3914 | (409) 5 | 4323 | (459) 4 |
| Mbo II | gaaga | 8/7 | 11 | 1 | (11)11 | 12 | (530) 4 | 542 | (828) 2 | 1370 | (347) 6 |
| | | | | 1717 | (405) 5 | 2122 | (3)12 | 2125 | (165) 7 | 2290 | (1510) 1 |
| | | | | 3800 | (57)10 | 3857 | (91) 8 | 3948 | (771) 3 | 4719 | (63) 9 |
| Nae I | gcc/ggc | | 11 | 1 | (1630) 1 | 1631 | (195) 7 | 1826 | (267) 5 | 2093 | (118)10 |
| | | | | 2211 | (220) 6 | 2431 | (30)12 | 2461 | (75)11 | 2536 | (464) 3 |
| | | | | 3000 | (187) 8 | 3187 | (147) 9 | 3334 | (420) 4 | 3754 | (1028) 2 |
| Nci I | cc/sgg | | 11 | 1 | (1074) 1 | 1075 | (13)11 | 1088 | (875) 3 | 1963 | (197) 8 |
| | | | | 2160 | (1)12 | 2161 | (38)10 | 2199 | (253) 6 | 2452 | (241) 7 |
| | | | | 2693 | (506) 5 | 3199 | (67) 9 | 3266 | (953) 2 | 4219 | (563) 4 |
| Taq I | t/cga | | 11 | 1 | (425) 4 | 426 | (1311) 1 | 1737 | (788) 2 | 2525 | (142) 9 |
| | | | | 2667 | (65)10 | 2732 | (309) 7 | 3041 | (378) 5 | 3419 | (27)11 |
| | | | | 3446 | (24)12 | 3470 | (367) 6 | 3837 | (662) 3 | 4499 | (283) 8 |
| Gdi II | yggccg | -5/-1 | 12 | 1 | (241) 7 | 242 | (1186) 1 | 1428 | (663) 3 | 2091 | (118) 9 |
| | | | | 2209 | (254) 6 | 2463 | (75)10 | 2538 | (22)13 | 2560 | (490) 5 |
| | | | | 3050 | (171) 8 | 3221 | (42)11 | 3263 | (531) 4 | 3794 | (964) 2 |
| Sec I | c/cnngg | | 12 | 4758 | (24)12 | | | | | | |
| | | | | 1 | (390) 5 | 391 | (1095) 1 | 1486 | (295) 7 | 1781 | (211) 8 |
| | | | | 1992 | (167)10 | 2159 | (1)13 | 2160 | (123)11 | 2283 | (168) 9 |
| | | | | 2451 | (815) 2 | 3266 | (471) 4 | 3737 | (51)12 | 3788 | (649) 3 |
| | | | | 4437 | (345) 6 | | | | | | |

FIG. 11c-2

| Enzyme | Site | p1 | p2 | | | | | | | | |
|---|---|---|---|---|---|---|---|---|---|---|---|
| Alw I | ggatc | 4/5 | 13 | 1( 1510) 1 | 1511( 1)14 | 1512( 42)10 | 1554( 510) 4 |
| | | | | 2064( 406) 5 | 2470( 107) 7 | 2577( 336) 6 | 2913( 918) 2 |
| | | | | 3831( 16)11 | 3847( 13)12 | 3860( 85) 8 | 3945( 12)13 |
| | | | | 3957( 74) 9 | 4031( 751) 3 | | |
| Eae I | y/ggccr | | 13 | 1( 241) 8 | 242( 613) 3 | 855( 573) 4 | 1428( 663) 2 |
| | | | | 2091( 118)10 | 2209( 254) 7 | 2463( 75)11 | 2538( 22)14 |
| | | | | 2560( 490) 6 | 3050( 171) 9 | 3221( 42)12 | 3263( 531) 5 |
| | | | | 3794( 964) 1 | | | |
| Hinf I | g/antc | | 13 | 1( 41)12 | 42( 10)14 | 52( 284) 6 | 336( 315) 5 |
| | | | | 651( 1580) 1 | 2231( 595) 3 | 2826( 246) 8 | 3072( 274) 7 |
| | | | | 3346( 109) 9 | 3455( 772) 2 | 4227( 396) 4 | 4623( 75)10 |
| | | | | 4698( 65)11 | 4763( 19)13 | | |
| Bsr I | actgg | 1/-1 | 14 | 1( 582) 3 | 583( 270) 9 | 853( 442) 6 | 1295( 466) 5 |
| | | | | 1761( 292) 8 | 2053( 391) 7 | 2444( 529) 4 | 2973( 38)12 |
| | | | | 3011( 37)13 | 3048( 59)11 | 3107( 17)14 | 3124( 941) 1 |
| | | | | 4065( 117)10 | 4182( 13)15 | 4195( 587) 2 | |
| Cfr10 I | r/ccggy | | 14 | 1( 1630) 1 | 1631( 195) 6 | 1826( 152) 9 | 1978( 115)12 |
| | | | | 2093( 118)11 | 2211( 220) 5 | 2431( 30)15 | 2461( 75)14 |
| | | | | 2536( 166) 8 | 2702( 298) 4 | 3000( 187) 7 | 3187( 147)10 |
| | | | | 3334( 93)13 | 3427( 327) 3 | 3754( 1028) 2 | |

FIG. 11c-3

| | | | | | | | |
|---|---|---|---|---|---|---|---|
| Hga I | gacgc | 5/10 | 15 | 1( 1323) 1<br>2048( 681) 2<br>3271( 141)11<br>3663( 59)12 | 1324( 23)16<br>2729( 314) 5<br>3412( 24)15<br>3722( 196) 8 | 1347( 276) 7<br>3043( 183) 9<br>3436( 177)10<br>3918( 578) 3 | 1623( 425) 4<br>3226( 45)14<br>3613( 50)13<br>4496( 286) 6 |
| Hph I | ggtga | 8/7 | 15 | 1( 253) 7<br>1189( 68)13<br>1491( 259) 6<br>2656( 806) 2 | 254( 160)10<br>1257( 44)15<br>1750( 231) 8<br>3462( 64)14 | 414( 108)12<br>1301( 43)16<br>1981( 474) 4<br>3526( 328) 5 | 522( 667) 3<br>1344( 147)11<br>2455( 201) 9<br>3854( 928) 1 |
| Nla IV | ggnncc | | 15 | 1( 203)10<br>1726( 370) 5<br>2533( 554) 4<br>3378( 366) 6 | 204( 587) 3<br>2096( 67)13<br>3087( 226) 7<br>3744( 784) 1 | 791( 720) 2<br>2163( 176)12<br>3313( 51)14<br>4528( 39)15 | 1511( 215) 8<br>2339( 194)11<br>3364( 14)16<br>4567( 215) 9 |
| Alu I | ag/ct | | 17 | 1( 1)18<br>538( 210)10 | 2( 269) 5<br>748( 173)11 | 271( 57)16<br>921( 7)17 | 328( 210) 9<br>928( 621) 3 |

FIG.11d-1

Mse I   t/taa   18

| | | | |
|---|---|---|---|
| 1549( 226) 7 | 1775( 403) 4 | 2178( 961) 1 | 3139( 94)14 |
| 3233( 65)15 | 3298( 741) 2 | 4039( 257) 6 | 4296(136)12 |
| 4432( 226) 8 | 4658( 124)13 | | |

Sau96 I   g/gncc   18

| | | | |
|---|---|---|---|
| 1( 18)14 | 19( 122) 6 | 141( 21)12 | 162(132) 4 |
| 294( 61) 9 | 355( 12)16 | 367( 39)11 | 406( 61)10 |
| 467( 127) 5 | 594( 21)13 | 615( 7)17 | 622(732) 3 |
| 1354( 7)18 | 1361( 102) 7 | 1463( 6)19 | 1469( 77) 8 |
| 1546(2347) 1 | 3893( 876) 2 | 4769( 13)15 | |

| | | | |
|---|---|---|---|
| 1( 110)10 | 111(1616) 1 | 1727( 130) 8 | 1857(119) 9 |
| 1976( 187) 6 | 2163( 1)19 | 2164( 175) 7 | 2339(352) 4 |
| 2691( 102)11 | 2793( 15)17 | 2808( 506) 3 | 3314( 87)12 |
| 3401( 29)15 | 3430( 84)13 | 3514( 27)16 | 3541(193) 5 |
| 3734( 11)18 | 3745( 40)14 | 3785( 997) 2 | |

Nla III   catg/   19

| | | | |
|---|---|---|---|
| 1( 654) 2 | 655( 141)15 | 796( 180)11 | 976(362) 5 |
| 1338( 149)14 | 1487( 183)10 | 1670( 191) 8 | 1861( 78)18 |
| 1939( 177)12 | 2116( 39)20 | 2155( 219) 7 | 2374(138)16 |
| 2512( 374) 4 | 2886( 174)13 | 3060( 124)17 | 3184(397) 3 |
| 3581( 68)19 | 3649( 229) 6 | 3878( 720) 1 | 4598(184) 9 |

FIG.11d-2

| Hae II | rgcgc/y | 20 | | | | | | | | |
|---|---|---|---|---|---|---|---|---|---|---|
| | | | 1( | 504) 5 | 505( | 579) 2 | 1084( | 544) 4 | 1628( | 29)21 |
| | | | 1657( | 97) 9 | 1754( | 69)14 | 1823( | 545) 3 | 2368( | 60)16 |
| | | | 2428( | 73)13 | 2501( | 32)19 | 2533( | 97)10 | 2630( | 373) 7 |
| | | | 3003( | 30)20 | 3033( | 77)12 | 3110( | 40)18 | 3150( | 478) 6 |
| | | | 3628( | 79)11 | 3707( | 63)15 | 3770( | 583) 1 | 4353( | 370) 8 |
| | | | 4723( | 59)17 | | | | | | |
| ScrF I | cc/ngg | 20 | | | | | | | | |
| | | | 1( | 658) 2 | 659( | 72)14 | 731( | 344) 6 | 1075( | 13)19 |
| | | | 1088( | 694) 1 | 1782( | 22)18 | 1804( | 159)12 | 1963( | 29)17 |
| | | | 1992( | 168)11 | 2160( | 1)21 | 2161( | 38)16 | 2199( | 253) 7 |
| | | | 2452( | 241) 8 | 2693( | 506) 4 | 3199( | 67)15 | 3266( | 522) 3 |
| | | | 3788( | 431) 5 | 4219( | 218) 9 | 4437( | 13)20 | 4450( | 121)13 |
| | | | 4571( | 211)10 | | | | | | |
| Bbv I | gcagc | 8/12 24 | | | | | | | | |
| | | | 1( | 814) 1 | 815( | 563) 2 | 1378( | 248) 7 | 1626( | 29)21 |
| | | | 1655( | 118)12 | 1773( | 3)24 | 1776( | 45)19 | 1821( | 458) 3 |
| | | | 2279( | 418) 5 | 2697( | 201)10 | 2898( | 99)15 | 2997( | 39)20 |
| | | | 3036( | 101)14 | 3137( | 16)23 | 3153( | 78)17 | 3231( | 208) 8 |
| | | | 3439( | 107)13 | 3546( | 170)11 | 3716( | 266) 6 | 3982( | 206) 9 |
| | | | 4188( | 3)25 | 4191( | 65)18 | 4256( | 419) 4 | 4675( | 18)22 |
| | | | 4693( | 89)16 | | | | | | |

FIG. 11d-3

Dpn I    ga/tc    26

| | | | |
|---|---|---|---|
| 1( 125) 9 | 126( 982) 1 | 1108( 75)16 | 1183( 329) 5 |
| 1512( 42)19 | 1554( 26)21 | 1580( 7)27 | 1587( 121)10 |
| 1708( 27)20 | 1735( 129) 8 | 1864( 120)11 | 1984( 54)18 |
| 2038( 26)22 | 2064( 406) 4 | 2470( 107)12 | 2577( 102)13 |
| 2679( 79)14 | 2758( 155) 7 | 2913( 623) 3 | 3536( 295) 6 |
| 3831( 17)23 | 3848( 12)24 | 3860( 78)15 | 3938( 8)26 |
| 3946( 11)25 | 3957( 75)17 | 4032( 750) 2 | |

Mbo I    /gatc    26

| | | | |
|---|---|---|---|
| 1( 125) 9 | 126( 982) 1 | 1108( 75)16 | 1183( 329) 5 |
| 1512( 42)19 | 1554( 26)21 | 1580( 7)27 | 1587( 121)10 |
| 1708( 27)20 | 1735( 129) 8 | 1864( 120)11 | 1984( 54)18 |
| 2038( 26)22 | 2064( 406) 4 | 2470( 107)12 | 2577( 102)13 |
| 2679( 79)14 | 2758( 155) 7 | 2913( 623) 3 | 3536( 295) 6 |
| 3831( 17)23 | 3848( 12)24 | 3860( 78)15 | 3938( 8)26 |
| 3946( 11)25 | 3957( 75)17 | 4032( 750) 2 | |

Sau3A I    /gatc    26

| | | | |
|---|---|---|---|
| 1( 125) 9 | 126( 982) 1 | 1108( 75)16 | 1183( 329) 5 |
| 1512( 42)19 | 1554( 26)21 | 1580( 7)27 | 1587( 121)10 |
| 1708( 27)20 | 1735( 129) 8 | 1864( 120)11 | 1984( 54)18 |
| 2038( 26)22 | 2064( 406) 4 | 2470( 107)12 | 2577( 102)13 |
| 2679( 79)14 | 2758( 155) 7 | 2913( 623) 3 | 3536( 295) 6 |
| 3831( 17)23 | 3848( 12)24 | 3860( 78)15 | 3938( 8)26 |
| 3946( 11)25 | 3957( 75)17 | 4032( 750) 2 | |

```
BstU I   cg/cg
34      1( 176)10    177( 669) 2    846( 774) 1   1620( 271) 5
     1891( 156)11   2047(  42)23   2089( 195) 8   2284(  60)17
     2344(  46)22   2390(   2)30   2392(   2)31   2394( 193) 9
     2587(  95)14   2682(  55)19   2737(  83)15   2820(   2)32
     2822( 344) 4   3166(   8)29   3174(   2)33   3176(  18)27
     3194(  34)24   3228( 130)13   3358(  47)21   3405(  54)20
     3459( 153)12   3612(  68)16   3680(  58)18   3738(  11)28
     3749(   2)34   3751(  25)26   3776( 196) 7   3972( 581) 3
     4553( 198) 6   4751(   2)35   4753(  29)25

Hpa II   c/cgg
34      1( 455) 2    456( 620) 1   1076(  12)30   1088( 427) 3
     1515( 117)15   1632( 195) 9   1827( 136)14   1963(  16)28
     1979( 115)17   2094(  67)22   2161(  39)24   2200(  12)31
     2212(  23)26   2235( 197) 8   2432(  21)27   2453(   9)33
     2462(  75)20   2537( 157)12   2694(   9)34   2703(  88)18
     2791( 210) 6   3001( 187)11   3188(  11)32   3199(  67)23
     3266(  69)21   3335(  15)29   3350(  78)19   3428(   5)35
     3433( 117)16   3550( 205) 7   3755( 274) 5   4029( 190)10
     4219(  26)25   4245( 147)13   4392( 390) 4

Msp I    c/cgg
34      1( 455) 2    456( 620) 1   1076(  12)30   1088( 427) 3
     1515( 117)15   1632( 195) 9   1827( 136)14   1963(  16)28
     1979( 115)17   2094(  67)22   2161(  39)24   2200(  12)31
     2212(  23)26   2235( 197) 8   2432(  21)27   2453(   9)33
     2462(  75)20   2537( 157)12   2694(   9)34   2703(  88)18
     2791( 210) 6   3001( 187)11   3188(  11)32   3199(  67)23
     3266(  69)21   3335(  15)29   3350(  78)19   3428(   5)35
     3433( 117)16   3550( 205) 7   3755( 274) 5   4029( 190)10
     4219(  26)25   4245( 147)13   4392( 390) 4
```

| Hae III | gg/cc | 35 | | | | | |
|---|---|---|---|---|---|---|---|
| | | | 1( | 111)16 | 112( | 131)13 | 243( 211) 9 | 454( 40)26 |
| | | | 494( | 362) 3 | 856( 222) 8 | 1078( 351) 4 | 1429( 74)18 |
| | | | 1503( | 474) 1 | 1977( 115)15 | 2092( 72)19 | 2164( 46)24 |
| | | | 2210( | 58)22 | 2268( 196)10 | 2464( 75)17 | 2539( 22)31 |
| | | | 2561( | 130)14 | 2691( 24)29 | 2715( 71)20 | 2786( 265) 7 |
| | | | 3051( | 171)12 | 3222( 42)25 | 3264( 51)23 | 3315( 18)33 |
| | | | 3333( | 69)21 | 3402( 285) 6 | 3687( 12)35 | 3699( 36)28 |
| | | | 3735( | 22)32 | 3757( 38)27 | 3795( 327) 5 | 4122( 434) 2 |
| | | | 4556( | 18)34 | 4574( 11)36 | 4585( 174)11 | 4759( 23)30 |
| Mnl I | cctc | 7/7 | 35 | | | | |
| | | | 1( | 28)29 | 29( 171)10 | 200( 217) 9 | 417( 35)27 |
| | | | 452( | 57)23 | 509( 496) 1 | 1005( 75)17 | 1080( 22)31 |
| | | | 1102( | 399) 3 | 1501( 150)12 | 1651( 69)22 | 1720( 3)36 |
| | | | 1723( | 16)33 | 1739( 52)25 | 1791( 276) 6 | 2067( 129)14 |
| | | | 2196( | 70)20 | 2266( 423) 2 | 2689( 99)16 | 2788( 12)34 |
| | | | 2800( | 141)13 | 2941( 302) 5 | 3243( 7)35 | 3250( 75)18 |
| | | | 3325( | 164)11 | 3489( 108)15 | 3597( 75)19 | 3672( 17)32 |
| | | | 3689( | 70)21 | 3759( 24)30 | 3783( 377) 4 | 4160( 267) 7 |
| | | | 4427( | 57)24 | 4484( 226) 8 | 4710( 33)28 | 4743( 39)26 |

FIG.11e-3

Fnu4H I  gc/ngc
51

```
   1( 814) 1     815( 154) 9     969( 409) 2    1378( 228) 3
1606(  20)36    1626(  29)33    1655(  45)29    1700(  57)25
1757(  16)41    1773(   3)44    1776(  45)30    1821( 146)10
1967(  54)26    2021(  69)23    2090(  51)28    2141( 138)12
2279(   3)45    2282(   3)46    2285( 103)18    2388( 174) 7
2562(   3)47    2565( 132)13    2697( 201) 5    2898(  22)35
2920(  77)22    2997(  39)31    3036( 101)19    3137(  16)42
3153(  78)21    3231( 128)15    3359(   3)48    3362(  28)34
3390(  13)43    3403(  36)32    3439( 107)17    3546( 132)14
3678(  19)37    3697(  19)38    3716(   3)49    3719(  17)40
3736(   3)50    3739(  54)27    3793( 189) 6    3982( 206) 4
4188(   3)51    4191(  65)24    4256( 143)11    4399( 155) 8
4554( 118)16    4672(   3)52    4675(  18)39    4693(  89)20
```

Hha I  gcg/c
52

| | | | |
|---|---|---|---|
| 1085( 519) 1 | 1604( 25)42 | 1629( 29)36 | 1658( 97)15 |
| 1755( 69)21 | 1824( 264) 6 | 2088( 281) 4 | 2369( 22)43 |
| 2391( 2)48 | 2393( 2)49 | 2395( 34)31 | 2429( 73)20 |
| 2502( 32)33 | 2534( 52)25 | 2586( 2)50 | 2588( 15)45 |
| 2603( 28)37 | 2631( 52)26 | 2683( 53)24 | 2736( 85)16 |
| 2821( 183) 9 | 3004( 30)34 | 3034( 77)17 | 3111( 40)30 |
| 3151( 22)44 | 3173( 2)51 | 3175( 2)52 | 3177( 26)40 |
| 3203( 26)41 | 3229( 54)23 | 3283( 74)18 | 3357( 198) 8 |
| 3555( 74)19 | 3629( 52)27 | 3681( 27)39 | 3708( 42)29 |
| 3750( 2)53 | 3752( 13)46 | 3765( 6)47 | 3771( 46)28 |
| 3817( 154)12 | 3971( 109)13 | 4080( 174)11 | 4254( 100)14 |
| 4354( 67)22 | 4421( 270) 5 | 4691( 33)32 | 4724( 28)38 |
| 4752( 30)35 | | | |

FIG.11f-2

HinP I    g/cgc    52

```
   1( 175)10     176( 330) 3     506( 341) 2     847( 238) 7
1085( 519) 1    1604(  25)42    1629(  29)36    1658(  97)15
1755(  69)21    1824( 264) 6    2088( 281) 4    2369(  22)43
2391(   2)48    2393(   2)49    2395(  34)31    2429(  73)20
2502(  32)33    2534(  52)25    2586(   2)50    2588(  15)45
2603(  28)37    2631(  52)26    2683(  53)24    2736(  85)16
2821( 183) 9    3004(  30)34    3034(  77)17    3111(  40)30
3151(  22)44    3173(   2)51    3175(   2)52    3177(  26)40
3203(  26)41    3229(  54)23    3283(  74)18    3357( 198) 8
3555(  74)19    3629(  52)27    3681(  27)39    3708(  42)29
3750(   2)53    3752(  13)46    3765(   6)47    3771(  46)28
3817( 154)12    3971( 109)13    4080( 174)11    4254( 100)14
4354(  67)22    4421( 270) 5    4691(  33)32    4724(  28)38
4752(  30)35
```

991 sites found

FIG. 11f-3

No Sites found for the following Restriction Endonucleases

| | | | | |
|---|---|---|---|---|
| Afl II | c/ttaag | Kpn I | ggtac/c | Sfi I | ggccnnnn/nggcc |
| Asp718 | g/gtacc | Mlu I | a/cgcgt | SnaB I | tac/gta |
| Avr II | c/ctagg | Nhe I | g/ctagc | Spe I | a/ctagt |
| BsaA I | yac/gtr | Not I | gc/ggccgc | Sph I | gcatg/c |
| BstB I | tt/cgaa | PaeR7 I | c/tcgag | Spl I | c/gtacg |
| Bsu36 I | cc/tnagg | PflM I | ccannnn/ntgg | Ssp I | aat/att |
| Cla I | at/cgat | Pml I | cac/gtg | Xba I | t/ctaga |
| Dra III | cacnnn/gtg | Rsa I | gt/ac | Xca I | gta/tac |
| Eco47 III | agc/gct | Sac I | gagct/c | Xho I | c/tcgag |
| Gsu I | ctggag 16/14 | Sca I | agt/act | Xmn I | gaannn/nnttc |
| Hpa I | gtt/aac | | | | |

Figure A
Strategy for the construction of plasmid pIA7 containing the pro-insulin gene.

Figure B- Strategy for the construction of plasmid pHIS containing pro-insulin gene with the oligo (HIS)$_6$ insertion (Met-Ala-His-His-His-His-His-His-Met-Gly-Arg).

Construction of the pPLT4 Expression Vector

The plasmid pLC28 was cleaved with restriction enzyme EcoRI and ligated with the synthetic fragment of the Leader sequence of phage T7. The resulting fragment was utilized to transform Escherichia Coli CELLS N4830-1, giving rise to plasmid pPLT-4

FIG. 15

5' AAT TTC TAG AAA TAA TTT TGT TTA ACT TTA AGA AGG AGA
AG ATC TTT ATT AAA ACA AAT TGA AAT TCT TCC TCT

TAT ATC CAT GGT G 3'
ATA TAG GAT CCA CTT AA

Nucleotide sequence of the synthetic fragment containing the leader region of phage T7

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 9562 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
AAGCTTCAGT TGAAGATATT AAGAACAGCC TCGCAGATGA CGAATCATTG GGATTCCCAT      60

CTTTTTTGTT TGTTGAAGGC TTCGAAGTCA ACTTCTATAA TTCTTGTCGG AGCGTCTACT     120

GCTTAGTAAC CCTAAGGGTA GAAAAAACAA ACAACTTCCG GACACCATTG GTTTTGCCAG     180

AACTGTTTTC GGGCCGACCA CATCCGATCT GACAGATTTT TTAATCGGGA AAGGAATGTC     240

CTGTGGTAAC CAAAACGGTC TTGACAAAAG CCCGGCTGGT GTAGGCTAGA CTGTCTAAAA     300

AATTAGCCCT TTCCTTACAG ATTAAGCAGT GGAGAGCGCG TTCAGATAGA GCCACTGATG     360

AGGGGAACCA CCAAAGACGA TGTTATGCAT ATGCATTTCA TAATTCGTCA CCTCTCGCGC     420

AAGTCTATCT CGGTGACTAC TCCCCTTGGT GGTTTCTGCT ACAATACGTA TACGTAAAGT     480

TCGGCCGAAC AACGGTGAAG GTAGAAGCCA AGCTACCTGT ATTTGGCGAT ATATTAAAGG     540

TCTTAGGGGC AACAGATATT AGCCGGCTTG TTGCCACTTC CATCTTCGGT TCGATGGACA     600

TAAACCGCTA TATAATTTCC AGAATCCCCG TTGTCTATAA GAAGGGGAGC TTTTTGACTC     660

ATTGGATATA GTCATTAAGC CAAAATTTAA AAGGGATATA AAAAAGGTTG CCAAGGATAT     720

CTTCCCCTCG AAAAACTGAG TAACCTATAT CAGTAATTCG GTTTTAAATT TTCCCTATAT     780
```

```
TTTTTCCAAC GGTTCCTATA TATTTTTAAC CCGTCACCTC AATTTTCGAC ATTAGCCTGC      840

GGGCAAAAGA TGAGGCCGGA GATATTTTAA CAGAACATTA ATAAAAATTG GGCAGTGGAG      900

TTAAAAGCTG TAATCGGACG CCCGTTTTCT ACTCCGGCCT CTATAAAATT GTCTTGTAAT      960

TCTATCAGAA AAAGGCCATC TCTCAGCGCC TCTGAACAAG GTCACCAATG CTGAGATAGC     1020

TGAAGAGATG GCATATTGCT AGATAGTCTT TTTCCGGTAG AGAGTCGCGG AGACTTGTTC     1080

CAGTGGTTAC GACTCTATCG ACTTCTCTAC CGTATAACGA ACGCAAGAAT GAAAAGTGAT     1140

ATACTGGAAT GTTTTAAAAG GCAGGTGGGC AAAGTTAAGG ATTAATTATC AGGAGTAATT     1200

TGCGTTCTTA CTTTTCACTA TATGACCTTA CAAAATTTTC CGTCCACCCG TTTCAATTCC     1260

TAATTAATAG TCCTCATTAA ATGCGGAACA GAATCATGCC TGGTGTTTAC ATAGTAATAA     1320

TTCCTTACGT TATCGTAAGC ATTTGCTATC TCCTTTTCCG TACGCCTTGT CTTAGTACGG     1380

ACCACAAATG TATCATTATT AAGGAATGCA ATAGCATTCG TAAACGATAG AGGAAAAGGC     1440

CCACTACATT CCTGGTGTTT CTTTTTCAGC TCATAGAGAT GGTCTTGGGG CGACATTGTC     1500

ATCATATGCA GGAACCATGA GGTGATGTAA GGACCACAAA GAAAAAGTCG AGTATCTCTA     1560

CCAGAACCCC GCTGTAACAG TAGTATACGT CCTTGGTACT TTGCAATCCT GATTGCTGCC     1620

TTGACGTTTC TAATCGGAAG CAGAACGCGC CGACTGGCCA AGATTAGAGA GTATGGGTAT     1680

AACGTTAGGA CTAACGACGG AACTGCAAAG ATTAGCCTTC GTCTTGCGCG GCTGACCGGT     1740

TCTAATCTCT CATACCCATA ATGACATCGG TAGTTATTGT CTATGCCCTT AGTTTTGTTG     1800

AGCTTGGAGC TTTGTTTTTC TGCGGGTTAT TGCTTCTTTC TACTGTAGCC ATCAATAACA     1860

GATACGGGAA TCAAAACAAC TCGAACCTCG AAACAAAAAG ACGCCCAATA ACGAAGAAAG     1920

CAGCATAAGC GGCTACATGA TACCCACTAT CGCCATCGGC ATTGCTCTG CATCGTTCAT      1980

TCATATATGC ATCCTTGTTT GTCGTATTCG CCGATGTACT ATGGGTGATA GCGGTAGCCG     2040

TAACGGAGAC GTAGCAAGTA AGTATATACG TAGGAACAAA TCCAACTATA TAATTTGCCA     2100

GAGAACAAGA ATAACCCGGC CTCAGCGCCG GGTTTTCTTT GCCTCACGAT CGCCCCCAAA     2160

AGGTTGATAT ATTAAACGGT CTCTTGTTCT TATTGGGCCG GAGTCGCGGC CCAAAAGAAA     2220

CGGAGTGCTA GCGGGGGTTT AACATAACCA ATTGTATTTA TTGAAAAATA AATAGATACA     2280

ACTCACTAAA CATAGCAATT CAGATCTCTC ACCTACCAAA TTGTATTGGT TAACATAAAT     2340

AACTTTTTAT TTATCTATGT TGAGTGATTT GTATCGTTAA GTCTAGAGAG TGGATGGTTT     2400

CAATGCCCCC CTGCAAAAAA TAAATTCATA TAAAAAACAT ACAGATAACC ATCTGCGGTG     2460

ATAAATTATC TCTGGCGGTG GTTACGGGGG GACGTTTTTT ATTTAAGTAT ATTTTTTGTA     2520

TGTCTATTGG TAGACGCCAC TATTTAATAG AGACCGCCAC TTGACATAAA TACCACTGGC     2580

GGTGATACTG AGCACATCAG CAGGACGCAC TGACCACCAT GAAGGTGACG CTCTTAAAAA     2640

AACTGTATTT ATGGTGACCG CCACTATGAC TCGTGTAGTC GTCCTGCGTG ACTGGTGGTA     2700

CTTCCACTGC GAGAATTTTT TTAAGCCCTG AAGAAGGGCA GCATTCAAAG CAGAAGGCTT     2760

TGGGGTGTGT GATACGAAAC GAAGCATTGG CCGTAAGTGC AATTCGGGAC TTCTTCCCGT     2820

CGTAAGTTTC GTCTTCCGAA ACCCCACACA CTATGCTTTG CTTCGTAACC GGCATTCACG     2880

GATTGGCTAG AAATAATTTT GTTTAACTTT AAGAAGGAGA TATATCCATG GGTGAATTCT     2940

GAGGCCTGCA GGATCCGGAA CTAACCGATC TTTATTAAAA CAAATTGAAA TTCTTCCTCT     3000

ATATAGGTAC CCACTTAAGA CTCCGGACGT CCTAGGCCTT GCCCGCCTAA TGAGCGGGCT     3060

TTTTTTTAAG CTTGATCCAA TTCCCCCTAT CGTTCCACG ATCAGCGATC GGCTCGTTGC      3120

CGGGCGGATT ACTCGCCCGA AAAAAAATTC GAACTAGGTT AAGGGGGATA GCAAAGGTGC     3180
```

-continued

```
TAGTCGCTAG CCGAGCAACG CCTGCGCCGC TCCAAAGCCC GCGACGCAGC GCCGGCAGGC    3240

AGAGCAAGTA GAGGGCAGCG CCTGCAATCC ATGCCCACCC GGACGCGGCG AGGTTTCGGG    3300

CGCTGCGTCG CGGCCGTCCG TCTCGTTCAT CTCCCGTCGC GGACGTTAGG TACGGGTGGG    3360

GTTCCACGTT GTTATAGAAG CCGCATAGAT CGCCGTGAAG AGGAGGGGTC CGACGATCGA    3420

GGTCAGGCTG GTGAGCGCCG CAAGGTGCAA CAATATCTTC GGCGTATCTA GCGGCACTTC    3480

TCCTCCCCAG GCTGCTAGCT CCAGTCCGAC CACTCGCGGC CCAGTGAGCC TTGCAGCTGC    3540

CCCTGGCGTT CCTCATCCAC CTGCCTGGAC AACATTGCTT GCAGCGCCGG CATTCCGATG    3600

GGTCACTCGG AACGTCGACG GGGACCGCAA GGAGTAGGTG GACGGACCTG TTGTAACGAA    3660

CGTCGCGGCC GTAAGGCTAC CCACCCGAAG CAAGCAGGAC CATGATCGGG AACGCCATCC    3720

ATCCCCGTGT CGCGAAGGCA AGCAGGATGT AGCCTGTGCC GGTGGGCTTC GTTCGTCCTG    3780

GTACTAGCCC TTGCGGTAGG TAGGGGCACA GCGCTTCCGT TCGTCCTACA TCGGACACGG    3840

GTCGGCAATC ATTCCGAGCA TGAGTGCCCG CCTTTCGCCG AGCCGGGCGG CTACAGGGCC    3900

GGTGATCATT GCCTGGGCGA CAGCCGTTAG TAAGGCTCGT ACTCACGGGC GGAAAGCGGC    3960

TCGGCCCGCC GATGTCCCGG CCACTAGTAA CGGACCCGCT GTGAATGCAG AATGCCAAAT    4020

GCGGCAAGCG AAATGCCGAT CGTGGTCGCG TCCCAGTGAA AGCGATCCTC GCCGAAAATG    4080

CACTTACGTC TTACGGTTTA CGCCGTTCGC TTTACGGCTA GCACCAGCGC AGGGTCACTT    4140

TCGCTAGGAG CGGCTTTTAC ACCCAAAGCG CGGCCGGCAC CTGTCCGACA AGTTGCATGA    4200

TGAAGAAGAC CGCCATCAGG GCGGCGACGA CGGTCATGCC TGGGTTTCGC GCCGGCCGTG    4260

GACAGGCTGT TCAACGTACT ACTTCTTCTG GCGGTAGTCC CGCCGCTGCT GCCAGTACGG    4320

CCGGGCCCAC CGAACGAAGC TGAGCGGGTT GAGAGCCTCC CGGCGTAACG GCCGGCGTTC    4380

GCCTTTGTGC GACTCCGGCA GGCCCGGGTG GCTTGCTTCG ACTCGCCCAA CTCTCGGAGG    4440

GCCGCATTGC CGGCCGCAAG CGGAAACACG CTGAGGCCGT AAAGGAAACA GCCCGTCAGG    4500

AAATTGAGGC CGTTCAAGGC TGCCGCGGCG AAGAACGGAG CGTGGGGGA GAAACCGCCC    4560

TTTCCTTTGT CGGGCAGTCC TTTAACTCCG GCAAGTTCCG ACGGCGCCGC TTCTTGCCTC    4620

GCACCCCCCT CTTTGGCGGG ATCAGCCCAC CGAGCACAGG TCCCGCGACC ATCCCGAACC    4680

CGAAACAGGC GCTCATGAAG CCGAAGTGCC GCGCGCGCTC TAGTCGGGTG GCTCGTGTCC    4740

AGGGCGCTGG TAGGGCTTGG GCTTTGTCCG CGAGTACTTC GGCTTCACGG CGCGCGCGAG    4800

ATCGCCATCA GTGATATCGG CAATATAAGC GCCGGCTACC GCCCCAGTCG CCCCGGTGAT    4860

GCCGCCACG ATCCGCCCGA TAGCGGTAGT CACTATAGCC GTTATATTCG CGGCCGATGG    4920

CGGGGTCAGC GGGGCCACTA CGGCCGGTGC TAGGCGGGCT TATAGAGAAC CCAAAGGAAA    4980

GGCGCTGTCG CCATGATGGC GTAGTCGACA GTGGCGCCGG CCAGCGAGAC GAGCAAGATT    5040

ATATCTCTTG GGTTTCCTTT CCGCGACAGC GGTACTACCG CATCAGCTGT CACCGCGGCC    5100

GGTCGCTCTG CTCGTTCTAA GGCCGCCGCC CGAAACGATC CGACAGCGCG CCCAGCACAG    5160

GTGCGCAGGC AAATTGCACC AACGCATACA GCGCCAGCAG CCGGCGGCGG GCTTTGCTAG    5220

GCTGTCGCGC GGGTCGTGTC CACGCGTCCG TTTAACGTGG TTGCGTATGT CGCGGTCGTC    5280

AATGCCATAG TGGGCGGTGA CGTCGTTCGA GTGAACCAGA TCGCGCAGGA GGCCCGGCAG    5340

CACCGGCATA ATCAGGCCGA TTACGGTATC ACCCGCCACT GCAGCAAGCT CACTTGGTCT    5400

AGCGCGTCCT CCGGGCCGTC GTGGCCGTAT TAGTCCGGCT TGCCGACAGC GTCGAGCGCG    5460

ACAGTGCTCA GAATTACGAT CAGGGGTATG TTGGGTTTCA CGTCTGGCCT CCGGACCAGC    5520
```

```
ACGGCTGTCG CAGCTCGCGC TGTCACGAGT CTTAATGCTA GTCCCCATAC AACCCAAAGT    5580

GCAGACCGGA GGCCTGGTCG CTCCGCTGGT CCGATTGAAC GCGCGGATTC TTTATCACTG    5640

ATAAGTTGGT GGACATATTA TGTTTATCAG TGATAAAGTG GAGGCGACCA GGCTAACTTG    5700

CGCGCCTAAG AAATAGTGAC TATTCAACCA CCTGTATAAT ACAAATAGTC ACTATTTCAC    5760

TCAAGCATGA CAAAGTTGCA GCCGAATACA GTGATCCGTG CCGCCCTAGA CCTGTTGAAC    5820

GAGGTCGGCG TAGACGGTCT AGTTCGTACT GTTTCAACGT CGGCTTATGT CACTAGGCAC    5880

GGCGGGATCT GGACAACTTG CTCCAGCCGC ATCTGCCAGA GACGACACGC AAACTGGCGG    5940

AACGGTTGGG GGTTCAGCAG CCGGCGCTTT ACTGGCACTT CAGGAACAAG CGGGCGCTGC    6000

CTGCTGTGCG TTTGACCGCC TTGCCAACCC CCAAGTCGTC GGCCGCGAAA TGACCGTGAA    6060

GTCCTTGTTC GCCCGCGACG TCGACGCACT GGCCGAAGCC ATGCTGGCGG AGAATCATAG    6120

CACTTCGGTG CCGAGAGCCG ACGACGACTG GCGCTCATTT AGCTGCGTGA CCGGCTTCGG    6180

TACGACCGCC TCTTAGTATC GTGAAGCCAC GGCTCTCGGC TGCTGCTGAC CGCGAGTAAA    6240

CTGACTGGGA ATGCCCGCAG CTTCAGGCAG GCGCTGCTCG CCTACCGCGA TGGCGCGCGC    6300

ATCCATGCCG GCACGCGACC GACTGACCCT TACGGGCGTC GAAGTCCGTC CGCGACGAGC    6360

GGATGGCGCT ACCGCGCGCG TAGGTACGGC CGTGCGCTGG GGGCGCACCG CAGATGGAAA    6420

CGGCCGACGC GCAGCTTCGC TTCCTCTGCG AGGCGGGTTT TCGGCCGGG DACGCCGTCA    6480

CCCGCGTGGC GTCTACCTTT GCCGGCTGCG CGTCGAAGCG AAGGAGACGC TCCGCCCAAA    6540

AAGCCGGCCC CTGCGGCAGT ATGCGCTGAT GACAATCAGC TACTTCACTG TTGGGGCCGT    6600

GCTTGAGGAG CAGGCCGGCG ACAGCGAGTC CGGCGAGCGC TACGCGACTA CTGTTAGTCG    6660

ATGAAGTGAC AACCCCGGCA CGAACTCCTC GTCCGGCCGC TGTCGCTCAG GCCGCTCGCG    6720

GGCGGCACCG TTGAACAGGC TCCGCTCTCG CCGCTGTTGC GGGCCGCGAT AGACGCCTTC    6780

GACGAAGCCG GTCCGGACGC CCGCCGTGGC AACTTGTCCG AGGCGAGAGC GGCGACAACG    6840

CCCGGCGCTA TCTGCGGAAG CTGCTTCGGC CAGGCCTGCG AGCGTTCGAG CAGGGACTCG    6900

CGGTGATTGT CGATGGATTG GCGAAAAGGA GGCTCGTTGT CAGGAACGTT GAAGGACCGA    6960

TCGCAAGCTC GTCCCTGAGC GCCACTAACA GCTACCTAAC CGCTTTTCCT CCGAGCAACA    7020

GTCCTTGCAA CTTCCTGGCT GAAAGGGTGA CGATTGATCA GGACCGCTGC CGGAGCGCAA    7080

CCCACTCACT ACAGCAGAGC CATGTAGACA ACATCCCCTC CTTTCCCACT GCTAACTAGT    7140

CCTGGCGACG GCCTCGCGTT GGGTGAGTGA TGTCGTCTCG GTACATCGT TGTAGGGGAG    7200

CCCCTTTCCA CCGCGTCAGA GCCCCGTAGC GCCCGCTACG GGCTTTTTCA TGCCCTGCCC    7260

TAGCGTCCAA GCCTCACGCC GGGGAAAGGT GGCGCAGTCT CGGGGCATCG CGGGCGATGC    7320

CCGAAAAAGT ACGGGACGGG ATCGCAGGTT CGGAGTGCGG GCGCTCGGCC TCTCTGGCGG    7380

CCTTCTGGCG CTCCTGCTGC GGCGTCCGCT CGTGGGCCGC GGCGGGTCCG CGCGCCGGCC    7440

CGCGAGCCGG AGAGACCGCC GGAAGACCGC GAGGACGACG CCGCAGGCGA GCACCCGGCG    7500

CCGCCCAGGC GCGCGGCCGG TCGTGCGCTG GCGCTCGCGG GCGAGGTCCA GGGCGGCCGT    7560

CTTCACGTTC TGCCTTGCGC AGATGAGATA GATCCGTCGA AGCACGCGAC CGCGAGCGCC    7620

CGCTCCAGGT CCCGCCGGCA GAAGTGCAAG ACGGAACGCG TCTACTCTAT CTAGGCAGCT    7680

CCAAAAGGAT CTAGGTGAAG ATCCTTTTTG ATAATCTCAT GACCAAAATC CCTTAACGTG    7740

AGTTTTCGTT CCACTGAGCG GGTTTTCCTA GATCCACTTC TAGGAAAAAC TATTAGAGTA    7800

CTGGTTTTAG GGAATTGCAC TCAAAAGCAA GGTGACTCGC TCAGACCCCG TAGAAAAGAT    7860

CAAAGGATCT TCTTGAGATC CTTTTTTTCT GCGCGTAATC TGCTGCTTGC AAACAAAAAA    7920
```

```
AGTCTGGGGC ATCTTTTCTA GTTTCCTAGA AGAACTCTAG GAAAAAAAGA CGCGCATTAG      7980

ACGACGAACG TTTGTTTTTT ACCACCGCTA CCAGCGGTGG TTTGTTTGCC GGATCAAGAG      8040

CTACCAACTC TTTTTCCGAA GGTAACTGGC TTCAGCAGAG TGGTGGCGAT GGTCGCCACC      8100

AAACAAACGG CCTAGTTCTC GATGGTTGAG AAAAAGGCTT CCATTGACCG AAGTCGTCTC      8160

CGCAGATACC AAATACTGTC CTTCTAGTGT AGCCGTAGTT AGGCCACCAC TTCAAGAACT      8220

CTGTAGCACC GCCTACATAC GCGTCTATGG TTTATGACAG GAAGATCACA TCGGCATCAA      8280

TCCGGTGGTG AAGTTCTTGA GACATCGTGG CGGATGTATG CTCGCTCTGC TAATCCTGTT      8340

ACCAGTGGCT GCTGCCAGTG GCGATAAGTC GTGTCTTACC GGGTTGGACT CAAGACGATA      8400

GAGCGAGACG ATTAGGACAA TGGTCACCGA CGACGGTCAC CGCTATTCAG CACAGAATGG      8460

CCCAACCTGA GTTCTGCTAT GTTACCGGAT AAGGCGCAGC GGTCGGGCTG AACGGGGGGT      8520

TCGTGCACAC AGCCCAGCTT GGAGCGAACG ACCTACACCG CAATGGCCTA TTCCGCGTCG      8580

CCAGCCCGAC TTGCCCCCCA AGCACGTGTG TCGGGTCGAA CCTCGCTTGC TGGATGTGGC      8640

AACTGAGATA CCTACAGCGT GAGCATTGAG AAAGCGCCAC GCTTCCCGAA GGGAGAAAGG      8700

CGGACAGGTA TCCGGTAAGC TTGACTCTAT GGATGTCGCA CTCGTAACTC TTTCGCGGTG      8760

CGAAGGGCTT CCCTCTTTCC GCCTGTCCAT AGGCCATTCG GGCAGGGTCG AACAGGAGA      8820

GCGCACGAGG GAGCTTCCAG GGGGAAACGC CTGGTATCTT TATAGTCCTG TCGGGTTTCG      8880

CCGTCCCAGC CTTGTCCTCT CGCGTGCTCC CTCGAAGGTC CCCCTTTGCG GACCATAGAA      8940

ATATCAGGAC AGCCCAAAGC CCACCTCTGA CTTGAGCGTC GATTTTGTG ATGCTCGTCA       9000

GGGGGGCGGA GCCTATGGAA AAACGCCAGC AACGCGGCCT GGTGGAGACT GAACTCGCAG      9060

CTAAAAACAC TACGAGCAGT CCCCCCGCCT CGGATACCTT TTTGCGGTCG TTGCGCCGGA      9120

TTTTACGGTT CCTGGCCTTT TGCTGGCCTT TTGCTCACAT GTTCTTTCCT GCGTTATCCC      9180

CTGATTCTGT GGATAACCGT AAAATGCCAA GGACCGGAAA ACGACCGGAA AACGAGTGTA      9240

CAAGAAAGGA CGCAATAGGG GACTAAGACA CCTATTGGCA ATTACCGCCT TTGAGTGAGC      9300

TGATACCGCT CGCCGCAGCC GAACGACCGA GCGCAGCGAG TCAGTGAGCG AGGAAGCGGA      9360

TAATGGCGGA AACTCACTCG ACTATGGCGA GCGGCGTCGG CTTGCTGGCT CGCGTCGCTC      9420

AGTCACTCGC TCCTTCGCCT AGAGCGCCCA ATACGCAAAC CGCCTCTCCC CGCGCGTTGG      9480

CCGATTCATT AATGCAGAAT TTCTCGCGGG TTATGCGTTT GGCGGAGAGG GGCGCGCAAC      9540

CGGCTAAGTA ATTACGTCTT AA                                              9562

(2) INFORMATION FOR SEQ ID NO:2:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

AATTTCTAGA ATAATTTTG TTTAACTTTA AGAAGGAGAT ATATCCATGG TG              52

(2) INFORMATION FOR SEQ ID NO:3:

(i) SEQUENCE CHARACTERISTICS:
        (A) LENGTH: 52 base pairs
        (B) TYPE: nucleic acid
        (C) STRANDEDNESS: single
```

```
            (D) TOPOLOGY: linear (ii) MOLECULE TYPE: DNA (genomic)

(xi) SEQUENCE DESCRIPTION: SEQ ID NO:3:

AGATCTTTAT TAAAACAAAT TGAAATTCTT CCTCTATATA GGTACCACTT AA            52

(2) INFORMATION FOR SEQ ID NO:4:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:4:

AATTAAGCTT TTCGCGAATT CTGAGGCCTG CAGGATCC                            38

(2) INFORMATION FOR SEQ ID NO:5:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

TTCGAAAAGC GCTTAAGACT CCGGACGTCC TAGGTTAA                            38

(2) INFORMATION FOR SEQ ID NO:6:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:6:

GATCCGGAAG CCCGCCTAAT GAGCGGGCTT TTTTTTAAGC TT                       42

(2) INFORMATION FOR SEQ ID NO:7:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:7:

GCCTTCGGGC GGATTACTCG CCCGAAAAAA AATTCGAACT AG                       42
```

VECTOR FOR EXPRESSION OF HETEROLOGOUS PROTEIN AND METHODS FOR EXTRACTING RECOMBINANT PROTEIN AND FOR PURIFYING ISOLATED RECOMBINANT INSULIN

This application is a division of allowed U.S. application Ser. No. 08/886,967, filed Jul. 2, 1997 now U.S. Pat No. 6,068,993.

FIELD OF THE INVENTION

The present invention relates to a multi-purpose vector. The vector can be for expressing at least one heterologous protein in a suitable cell such as E. coli or other Gram negative bacteria. More specifically, the present invention relates to: a vector for expression of heterologous proteins comprising nucleic acid molecules for: an origin of replication region, optionally but preferably a selection marker (which can be a coding nucleic acid molecule inserted in a restriction site), a promoter, an initiation region e.g. a translation initiation region and/or a ribosome binding site, at least one restriction site and preferably multiple restriction sites, and a transcription terminator; a method for extracting recombinant protein without lysing the cell, e.g., bacteria; and a method for purifying isolated recombinant protein. The vector can facilitate the thermo-regulated production of a heterologous protein or proteins, e.g., pro-insulin.

Several publications are referenced in this application. Full citation to these publications is found at the end of the specification, immediately preceding the claims, or where the publication is mentioned; and each of these publications is hereby incorporated by reference. These publications relate to the state of the art to which the invention pertains; however, there is no admission that any of these publications is indeed prior art.

BACKGROUND OF THE INVENTION

Recombinant DNA technology has enabled the expression of foreign (heterologous) proteins in microbial and other host cells. A vector containing genetic material directing the host cell to produce a protein encoded by a portion of the heterologous DNA sequence is introduced into the host, and the transformant host cells can be fermented and subjected to conditions which facilitate the expression of the heterologous DNA, leading to the formation of large quantities of the desired protein.

The advantages of using a recombinantly produced protein in lieu of isolation from a natural source include: the ready availability of raw material; high expression levels, which is especially useful for proteins of low natural abundance; the ease with which a normally intracellular protein can be excreted into the expression medium, facilitating the purification process; and the relative ease with which modified (fusion) proteins can be created to further simplify the purification of the resultant protein.

However, the aforementioned benefits of recombinant DNA technology are also accompanied by several disadvantages, namely: the required elements of the active protein which result from post-translational modification (i.e., glycosylation) may not be carried out in the expression medium; proteolytic degradation of newly formed protein may result upon expression in host cells; and the formation of high molecular weight aggregates, often referred to as "inclusion bodies" or "refractile bodies", which result from the inability of the expressed proteins to fold correctly in an unnatural cellular environment. The recombinant protein cannot be excreted into the culture media upon formation of inclusion bodies.

Inclusion bodies contain protein in a stable non-native conformation; or, the protein aggregates may be amorphous, comprised of partially and completely denatured proteins, in addition to aberrant proteins synthesized as a result of inaccurate translation. Such inclusion bodies constitute a large portion of the total cell protein.

Inclusion bodies present significant problems during the purification of recombinant proteins, as they are relatively insoluble in aqueous buffers. Denaturants and detergents, i.e., guanidine hydrochloride, urea, sodium dodecylsulfate (SDS) and Triton X-100, may be necessary to isolate the proteins from the inclusion bodies, often at the expense of the biological activity of the protein itself, resulting from incorrect folding and modification of the amino acid residues in the sequence.

Additionally, a result of the expression of recombinant DNA in E. coli is the accumulation of high concentrations of acetate in the media, mainly during the induction phase. The deleterious effect of acetate accumulation (greater than 5 g/L) on cell growth and recombinant protein expression has been well documented in the literature.

Further, the recovery of the desired protein from inclusion bodies is often complicated by the need to separate the desired protein from other host cellular materials, in addition to separating the desired protein from inclusion body heterologous protein contaminants. The latter problem results from the strong attraction that inclusion body proteins have for one another, due to strong ionic and hydrophobic interactions.

Consequently, most established protocols for the isolation of recombinant proteins from inclusion bodies result in large quantities of biologically inactive material, and very low yields of active protein, uncontaminated by extraneous heterologous protein.

Researchers have focused on the manipulation of phage in order to stimulate protein synthesis by a variety of methods.

The promoters of the Lambda phage ($P_L$ and $P_R$) are strong promoters that are negatively controlled by the repressor coded by the gene cl. The mutation $cl^{857}$ rendered the repressor inactivate at temperatures above 37° C. Thus, the expression of a sequence controlled by these promoters and by the repressor $cl^{857}$ can be activated by a simple change in temperature. These promoters are often used in E. coli expression vectors, because they are strong and efficiently repressed (Denhardt & Colasanti, 1987).

Remaut et al. (1981) constructed a set of plasmids containing the promoter $P_L$. The promoter and the trp region of the gene were taken from a family of phages (trp44) and inserted in the plasmid pBR322, creating the first plasmid of a series, plasmid pPLa2. After several manipulations, other plasmids were obtained. The plasmids pPLa2 and pPLa8 contained the promoter $P_L$ fragment, the origin of replication, the ampicillin resistance gene from the plasmid pBR322, and a kanamycin resistance gene from the plasmid pMK20. The promoter region contained the promoter/ operator and the nutL site (antitermination), but it was lacking the beginning of the gene N.

The plasmids pPLc236, pPLc28 and pPLc24 are different from the previously identified plasmids, with respect to the direction of transcription from the promoter $P_L$ in relation to the orientation of the origin of replication, as found in pBR322 (a=anticlockwise, c=clockwise). The kanamycin resistance gene is absent in these three vectors. The difference between pPLc236 and pPLc8 is the presence or absence of a region (present in the former and absent in the latter), which affects the region of unique cloning sites. pPLc24 was derived from pPLc28 by insertion of a region containing the ribosome binding site of the gene for replicase from the phage MS2, enabling the expression of eukaryotic genes.

These plasmids were tested with the expression of different genes, e.g., the gene trpA from *Salmonella typhimurium,* cloned in the plasmid pPLc23 (predecessor of pPLc236), which showed 40% induction of product in relation to the total cellular protein. pLc236 programmed in *E. coli* resulted in a expression of the gene ROP as 20% of the total protein (Muesing et al., 1984). The proteins p4 and p3 of the phage 29 of *Bacillus subtilis,* were also produced from pPLci and reached 30% and 6%, respectively, of the total cellular protein induced in *E. coli,* after thermal induction (Mellado & Salas, 1982).

In 1983, Remault et al. (1983a) built a plasmid pPLc245, derived from pPLc24, in which the initial coding region of replicase was deleted and a region with several unique cloning-sites was added, permitting direct expression. The gene for human α-interferon was cloned into this plasmid, resulting in induction of protein of approximately 2% to 4% of the total cellular protein. For α-interferon, the levels of expression varied from 3% to 25% of the cellular protein, depending on the plasmids used, e.g., pPLc245, pPLc28 and pCP40, and on the presence of a transcription-terminator from phage T4 (Simons et al., 1984). The plasmid pCP40, derived from pPL, was built by Remaut et al. (1983b). The promoter-region was transferred to a plasmid derived from pKN402 with temperature dependent 'runaway' replication. When the cultures are heated to 42° C., the repressor $cI^{857}$ is deactivated and the promoter $P_L$ is liberated, resulting in an increase in the number of copies of the plasmid pCP40, by approximately ten fold.

Crowl et al. (1985) relates to four plasmids containing the promoter $P_L$. The plasmid pRC23 was built containing the promoter $P_L$ and a synthetic Shine-Dalgarno region, without the codon ATG, cloned in the plasmid pRC2 (derived from pBR322). To build the other three plasmids, pEV-vrfl, pEV-vrf2 and pEV-vrf3, a region with unique cloning sites was inserted, adding the initial ATG codon, such that in each one the reading frames are on phase. The plasmid pRC23 was used for the expression of interleucine-2 and α-interferon, with a level of 10% to 20% of the total cellular protein.

Lautenberg et al. (1983) built the plasmid pJL6, containing the promoter $P_L$, which codes for initiation of translation of the gene cII of the phage, with unique ClaI and HindIII cloning sites, located at 50 bp from the initial ATG site. Genes, adequately cloned in these sites are induced, producing fusion proteins with the protein CII. Seth et al. (1986) modified this vector so that the induction of proteins could occur without fusion. Three plasmids were constructed, containing a KpnI site in pANK-12, an HpaI site in pANH-1, and an NdeI site in pPL2 of the initial codon ATG of the gene CII of pJL6. In pANH-1, the amino acid 'valine' occurred more frequently in the amino-end of the induced protein. Production of oncogenes was obtained from these vectors.

Chang and Peterson (1992) also modified the plasmid pJL6 and built a line of plasmids, pXC, in which the region for initiation of translation of the gene CII was substituted by a synthetic one. Additionally, a region was inserted having several unique cloning sites. The region CII affects the efficiency of the translation if the expression is required without fusion. With the synthetic region, the efficiency rose between 10 and 20 times, depending on the spacing region between SD and ATG. The expression reached 48% of the total cellular protein for the protein 14-3-3 of cow brain, of which the DNA had been amplified by PCR.

Schauder et al. (1987) built a line of plasmids derived from pJL6, containing the promoters $P_R$ and $P_L$ in tandem, the region SD of the gene atpE (for subunit of ATPase), with the transcription terminator of the bacteriophage fd and with the gene of the repressor $cI^{857}$. These plasmids were named pJLA501 to -05 and differ in the regions of the multiple cloning sites. On testing the expression of the gene atpA (for a subunit of ATPase), an induction of 50% of the total cellular protein was found. The genes sucC and sucD, respectively, showed 30% and 15% induced protein in relation to the total cellular protein.

Rosenberg et al. (1983) built the plasmid pKC30 and its derivatives. The vector pKC30 is used for the expression of bacterial genes containing their proper translation-regulation regions. This vector contains a unique cloning HpaI site, located 321 bp downstream from the promoter $P_L$, within the coding region of the gene N. The expression of the activator CII and eight mutants in just one amino acid was achieved in the vector pKC30. Because CII is quickly recycled in *E. coli* and deleterious for cell growth, with insertion and expression of its gene in pKC30, levels of 3% to 5% of the total cellular protein were reached. The production of the protein CII rose when the protein N (anti-terminator) was provided by the host-cell, because of the presence of the 'upstream' sequences of the gene CII of the sites nutL, nutR (for anti-termination) and $t_{r1}$ (for termination). Other proteins were expressed from pKC30, such as the protein B of the phage Mu (Chaconas et al., 1985) and the protein UvrA of *E. coli* expressed at levels of 15% and 7% of the total cellular protein respectively.

For the expression of eukaryotic genes the plasmid pAS1, derived from pKC30, was built with the cloned gene CII. The complete coding region of CII was deleted and a BamHI site was added immediately 'downstream' of the ATG initiation codon. In this manner, the regulating regions for translation were maintained in the vector and a eukaryotic or synthetic gene can be expressed if cloned correctly to the BamHI site. Expression of the gene for the antigen t of the virus SV40 resulted in this vector in levels of 10% of the total cellular proteins, after one hour of thermal induction (Rosenberg et al., 1983).

Lowman et al. (1988) modified the plasmid pAS1, introducing a NcoI site in the initial ATG, creating the plasmid named pAS1-N. Expression of the gene CAT and fusion with proteins of the virus SV40 were obtained. Later, Lowman & Bina (1990) used these products to study the effect of temperature in thermal induction.

Mott et al. (1985) used pKC30 and pAS1 to express the bacterial gene rho and verified that the thermal induction did not result in high levels of expression of the protein Rho. Induction with nalidixic acid and mitomicina C was tested in the host cI, which provoked the induction of the syntheses of Rec a, resulting in an inactivation of the repressor cI. In this manner, levels of expression varying from 5% to 40% of the cellular protein were reached.

Hence, the manipulation of plasmids for expression of a protein or peptide of interest is a developing area and a method for the induction of complex proteins such as pro-insulin via manipulation of a plasmid and a plasmid therefrom, have not heretofore been developed or suggested.

U.S. Pat. No. 4,734,362, to Hung et al., is directed to a method of isolating polypeptides produced recombinantly in inclusion bodies. The disclosed method includes the cell lysis, and recovery of inclusion bodies comprising the desired recombinant protein, solubilization with denaturant, protection of the sulfhydryl groups of the recombinant protein, derivatization of cationic amino groups of the protein, and recovery of the derivatized recombinant protein.

Olson, U.S. Pat. No. 4,518,526 relates to a method of releasing active proteins from inclusion bodies by cell lysis, centrifugation, denaturation and renaturation. The patent teaches the necessity of the disruption of the cell to separate the soluble and insoluble protein, followed by treatment of the insoluble fraction with a strong denaturant, and recovery of the renatured heterologous protein.

Rausch, U.S. Pat. No. 4,766,224 is directed to a method of purification and solubilization of proteins produced in transformed microorganisms as inclusion bodies. The purification is effected by solubilization of the inclusion bodies in detergent, treatment with a strong denaturant, followed by chromatographic separation to obtain renatured active protein.

Builder et al., U.S. Pat. No. 4,620,948 is concerned with a process for isolating and purifying inclusion bodies by lysing the cell culture, precipitation of protein, denaturation of the insoluble fraction, and renaturation to isolate the refractile protein.

Similarly, U.S. Pat. Nos. 4,734,368, 4,659,568, 4,902,783, 5,215,896, and EP 337,243 and WO 87/02673 are each directed to methods of purifying proteins entrapped in inclusion bodies. These methods use of the following techniques (alone or in combination): cell lysis, denaturation, chromatographic separation, centrifugation, manipulation of the denaturation/renaturation of the protein, and the attachment of leader peptides which facilitate the separation of the proteins from the inclusion bodies.

Each of the aforementioned prior art processes utilize methods which disrupt the cell to release the inclusion bodies from the cellular material. There is no teaching or suggestion of a means for isolating inclusion bodies from cellular material without the disruption of the cell, nor is there a motivation to derive such a method from the teachings of the prior art. However, the lysis or disruption of cells is disadvantageous as it allows contaminants to be present with the desired protein, such as lipopolysaccharides, which are very difficult to separate from the desired protein.

U.S. Pat. Nos. 4,877,830, 5,115,102, 5,310,663, and EP 656,419, WO 91/11454, WO 91/16912, WO 94/07912, Proc. Natl. Acad. Sci. (1991) 88 (20), and Mol. Biol. Rep. (1993) 18: 223–230 are each directed to affinity purification of proteins. These documents relate to the use of (alone or in combination): metal chelate affinity chromatography for chromatographic separation of proteins having neighboring histidine residues, immunoaffinity chromatography, and the use of amino acid mimetics as eluents in affinity purification of proteins.

U.S. Pat. Nos. 4,766,205, 4,599,197, 4,923,967, and EP 312,358, EP 302,469, Biochemistry (1968), 7 (12), 4247, and J. Biological Chemistry (1959), 234 (7), 1733 are each directed to methods of sulfitolysis, i.e., the treatment of a protein, solubilized in a strongly denaturing solution, with a mild oxidant in the presence of sulfite ion, which converts cysteine and cystine residues to protein-S-sulfonates. The strongly denaturing solution is weakened to permit refolding, and disulfide linkages are reformed using a sulfhydryl compound, in the presence of the corresponding disulfide (oxidized) form. Similarly, EP 208,539 and WO 87/02985 are directed to methods of facilitating protein refolding in vitro.

EP 264,250, GB 2,067574, EP 055,945, MMW (1983) 125 (52), 14, J. Biol. Chem. (1971) 246 (22), 6786–91, J. Chrom. (1989) 461: 45–61 are each directed to insulin, its production from pro-insulin, and the purification of insulin and pro-insulin.

U.S. Pat. No. 4,578,355, to Rosenberg, is directed to the derivation and use of the $P_L$ transcription unit. EP 363,896 is directed to the use of ultrafiltration in protein purification.

Human insulin, a proteolytic digestion product of pro-insulin, is a polypeptide hormone produced by beta cells of the islets of Langerhans in the pancreas. Its purpose is to decrease the amount of glucose in the blood by promoting glucose uptake by cells, and increasing the capacity of the liver to synthesize glycogen. The action of insulin is antagonistic to glucagon, adrenal glucocorticoids and adrenaline, and its deficiency or reduced activity produces diabetes with a raised blood sugar level.

Human insulin has been prepared from several sources, including: isolation from human pancreas, peptide synthesis, the semisynthetic conversion from porcine insulin and fermentation of E. coli bacteria or Saccharomyces cerevisiae yeast, suitably encoded by DNA recombinant methods. These methods suffer from poor yield and cost efficiency, and the development of a high yielding, cost effective method of producing human insulin for the treatment of diabetes has been the subject of much research efforts in recent years.

Hence, a method for the induction of human pro-insulin via recombinant techniques has not heretofore been realized, wherein the protein may be isolated in substantial quantities from inclusion bodies, especially such a method wherein cell lysis or cell disruption is avoided.

OBJECTS AND SUMMARY OF THE INVENTION

Objects of the present invention may include providing at least one of: a vector comprising at least one nucleic acid such as DNA for cloning of a nucleic acid or for expression of at least one heterologous protein by a cell such as Gram negative bacteria (the vector can comprise a nucleic acid molecule, e.g., DNA, encoding: an origin of replication region, optionally and preferably a selection marker (which can be a coding nucleic acid in a restriction site), a promoter, an initiation region e.g. a translation initiation region and/or a ribosome binding site, at least one restriction site for insertion of heterologous nucleic acid, e.g., DNA, encoding the heterologous protein, and a transcription terminator); a method for extracting a recombinant protein from within a cell such as a recombinant Gram negative bacteria having a cell membrane; and, a method for purifying an isolated recombinant human insulin.

Accordingly, the present invention provides a vector comprising at least one nucleic acid molecule such as DNA for cloning of a nucleic acid molecule, or more preferably, for expression of at least one heterologous protein by cell such as a Gram negative bacteria. The vector can comprise DNA encoding the following: an origin of replication region, optionally and preferably a selection marker (which can be coding DNA in a restriction site), a promoter, an initiation region e.g. a translation initiation region and/or a ribosome binding site, at least one restriction site for insertion of heterologous DNA encoding the heterologous protein, and a transcription terminator.

The Gram negative bacteria can be E. coli. The origin of replication region can be from plasmid pUC8. The initiation region can be a translation initiation region and can be synthetic, e.g., synthetic Shine-Dalgarno regions from gene 10 of phage T7. The selection marker can be a tetracycline resistance marker. Alternatively or additionally, selection of transformed cells containing the vector can be on the basis of a product expressed by the heterologous DNA encoding the heterologous protein. The promoter can be a $P_L$ promoter. And, the transcription terminator can be a Rho-independent one.

Thus, the invention can provide a vector comprising DNA for expression of a heterologous protein by a Gram negative bacteria. The vector can comprise at least one nucleic acid molecule, e.g., DNA, encoding the following: an origin of replication region, a selection marker, a promoter, a translation initiation region or a ribosome binding site, at least one restriction site for insertion of heterologous DNA encoding the heterologous protein, and a transcription terminator.

The DNA encoding the at least one restriction site preferably encodes multiple restriction sites; and, the multiple restriction sites are preferably NcoI, EcoRI, StuI, PstI, BamHI, and BspEI.

The present invention further provides a vector for expression of a pro-insulin by a Gram negative bacteria. That is, in the inventive vector, at the at least one restriction site for insertion of heterologous DNA (or a heterologous nucleic acid sequence) there can be inserted a nucleic acid molecule such as DNA encoding pro-insulin, e.g., human pro-insulin. The protein expressed by the inserted nucleic acid molecule, e.g., pro-insulin such as human pro-insulin, can contain tag or a marker, for instance, a His tag (which is useful for separating, isolating and/or purifying the protein).

And therefore, more generally, inventive vectors can include at least one exogenous coding nucleic acid molecule at the at least one restriction site for insertion of a heterologous nucleic acid molecule, e.g., exogenous coding DNA can be at the at least one restriction site for insertion of heterologous DNA. Further, the exogenous coding DNA can encode, in addition to the heterologous protein, a marker or tag, for instance a His tag.

Still further, the invention provides a method for extracting a recombinant protein such as pro-insulin, e.g., human pro-insulin, from within a cell such as a recombinant Gram negative bacteria having a cell membrane, without lysing the bacteria. The method can comprises the steps of:

(a) permeabilizing the cell membrane by contacting the bacteria with a detergent under conditions which facilitate the extraction of native cell proteins from the cell membrane without extracting the recombinant protein from the cell membrane;

(b) solubilizing the recombinant protein and cell membrane; and (c) separating the recombinant protein from the cell membrane.

The invention also provides a method for purifying an isolated recombinant protein such as pro-insulin, e.g., human insulin, comprising:

(a) subjecting the isolated recombinant human insulin to sulfitolysis and separating a liquid product therefrom, (b) subjecting the liquid product from (a) to a Ni-chelating column and obtaining an eluate, (c) renaturing the eluate from (b), (d) converting the product from (c) e.g., with trypsin and carboxypeptidase B, and (e) subjecting the product from (d) to purification, e.g., chromatography, to obtain purified isolated recombinant human insulin.

These and other embodiments are disclosed or are obvious from and encompassed by, the following Detailed Description.

BRIEF DESCRIPTION OF THE FIGURES

In the following Detailed Description reference will be made to the accompanying drawings, incorporated herein by reference, wherein:

FIGS. 5 and 5A shows a map of vector pLMT8.5;

Figure 10B-3:
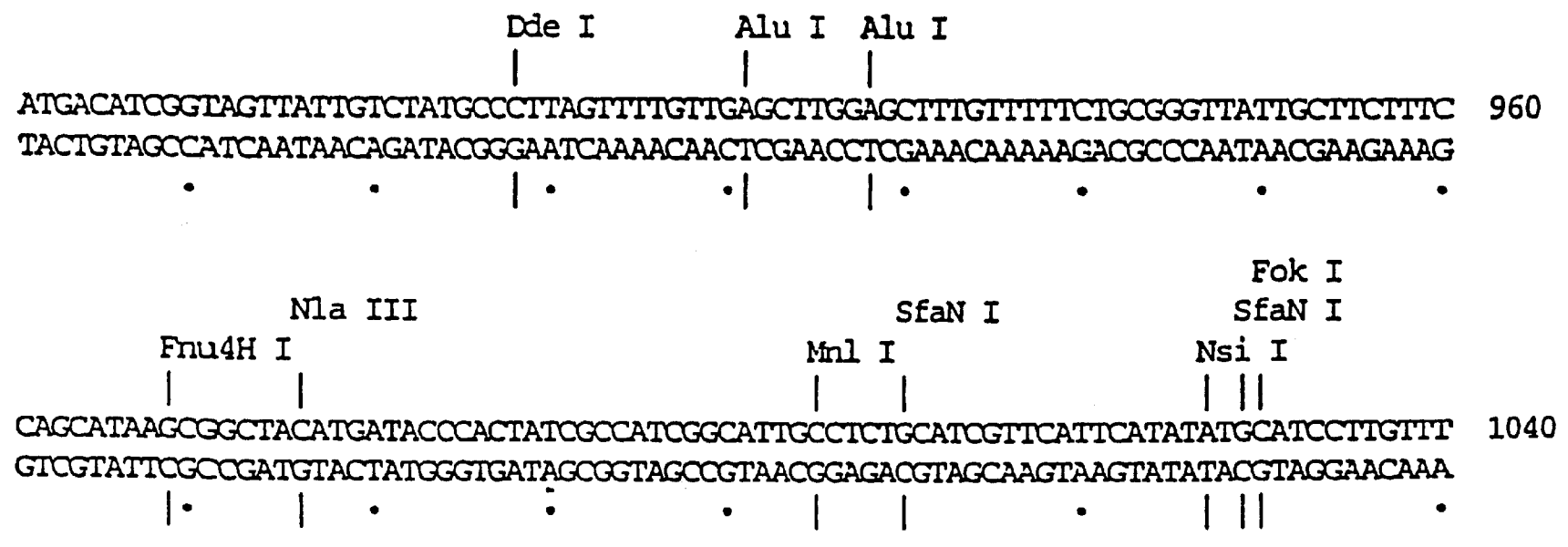
Figure 10D-1:
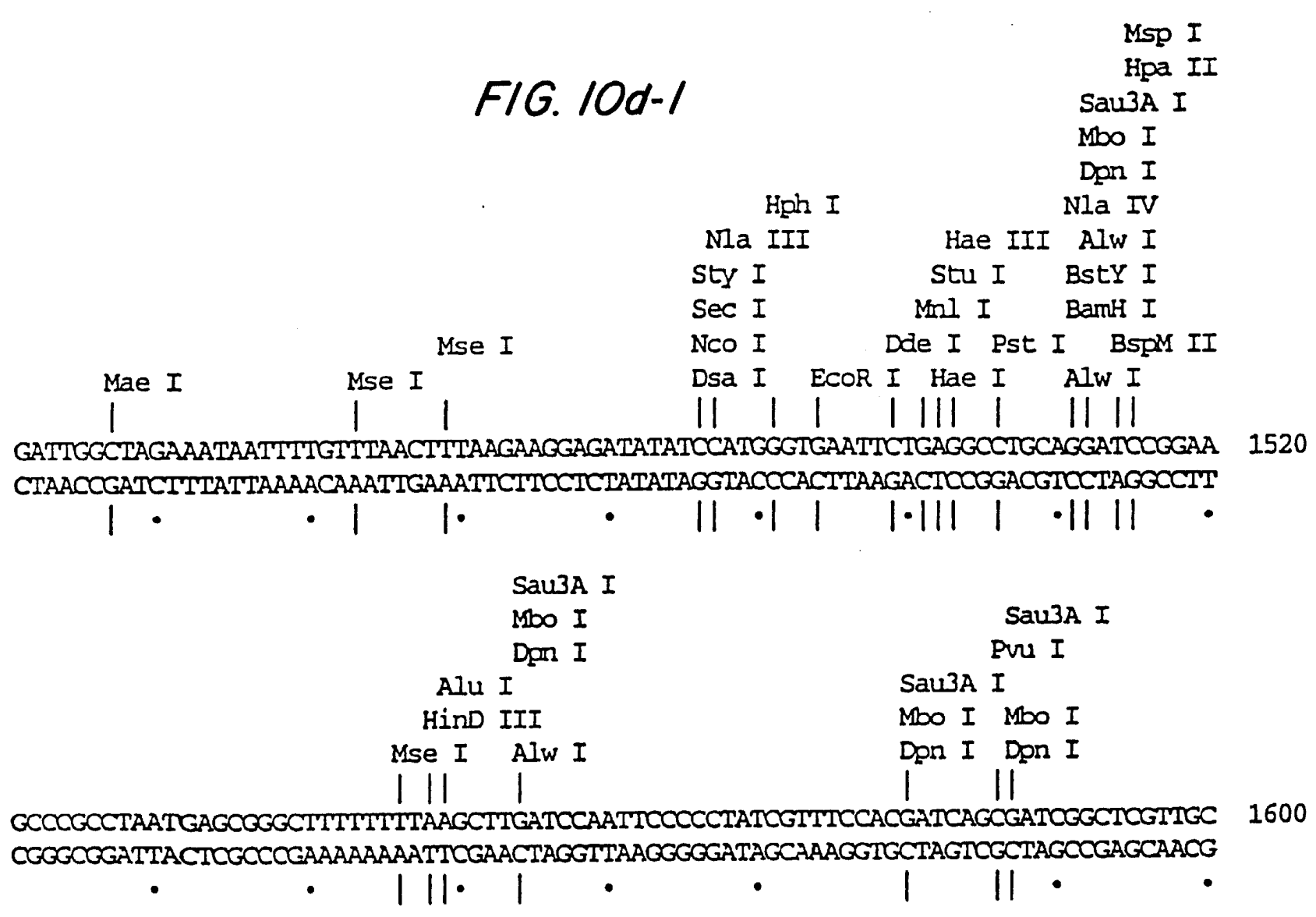
Figure 10D-2:
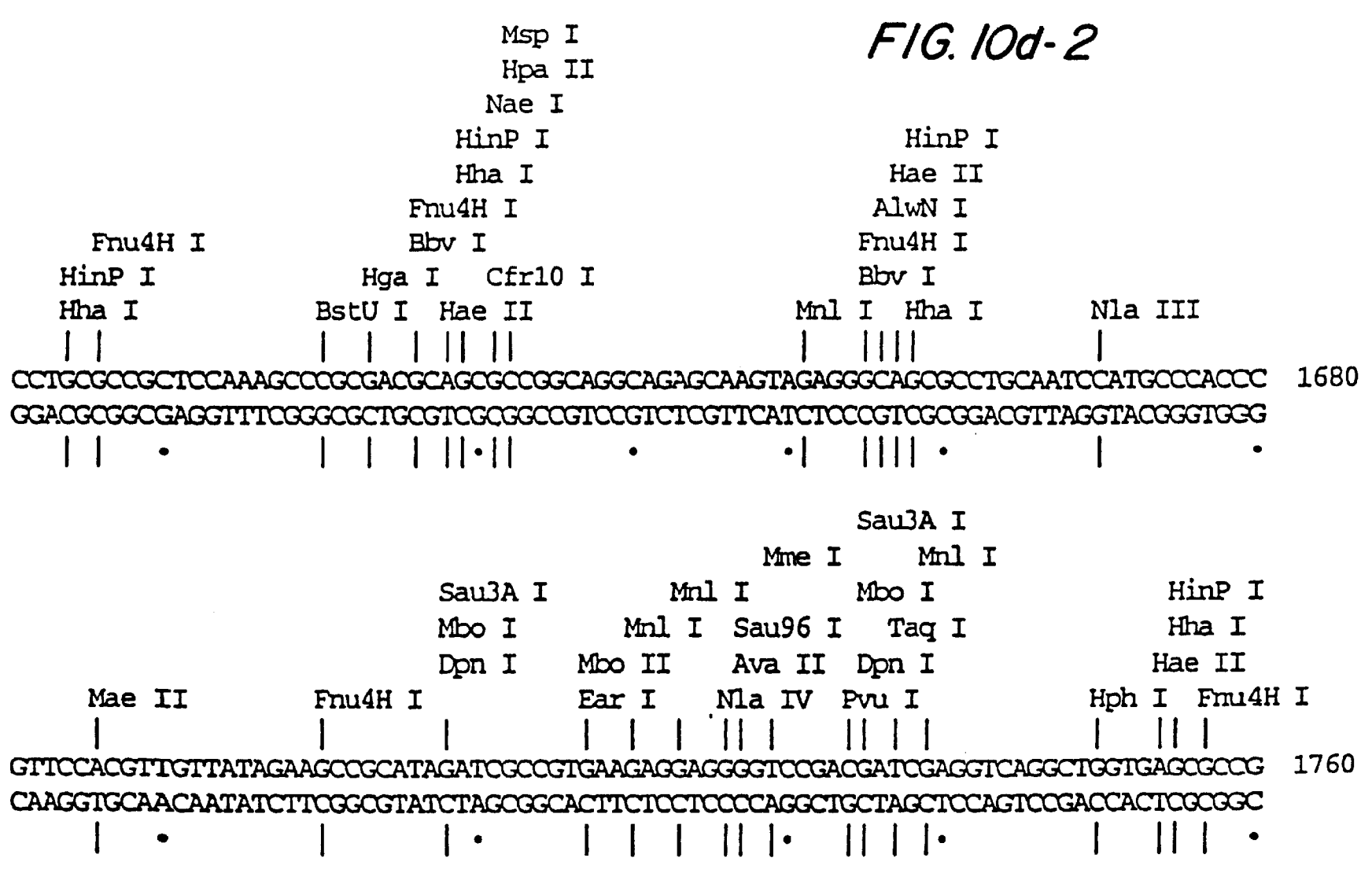
Figure 10G-2:
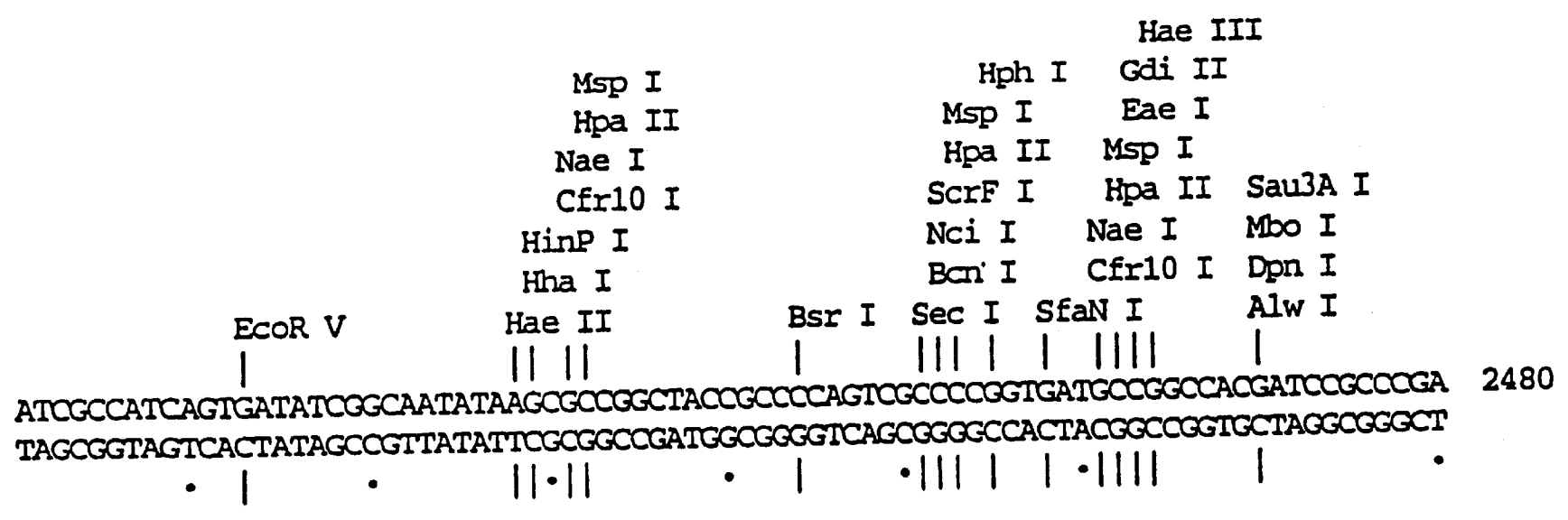
Figure 10H-1:
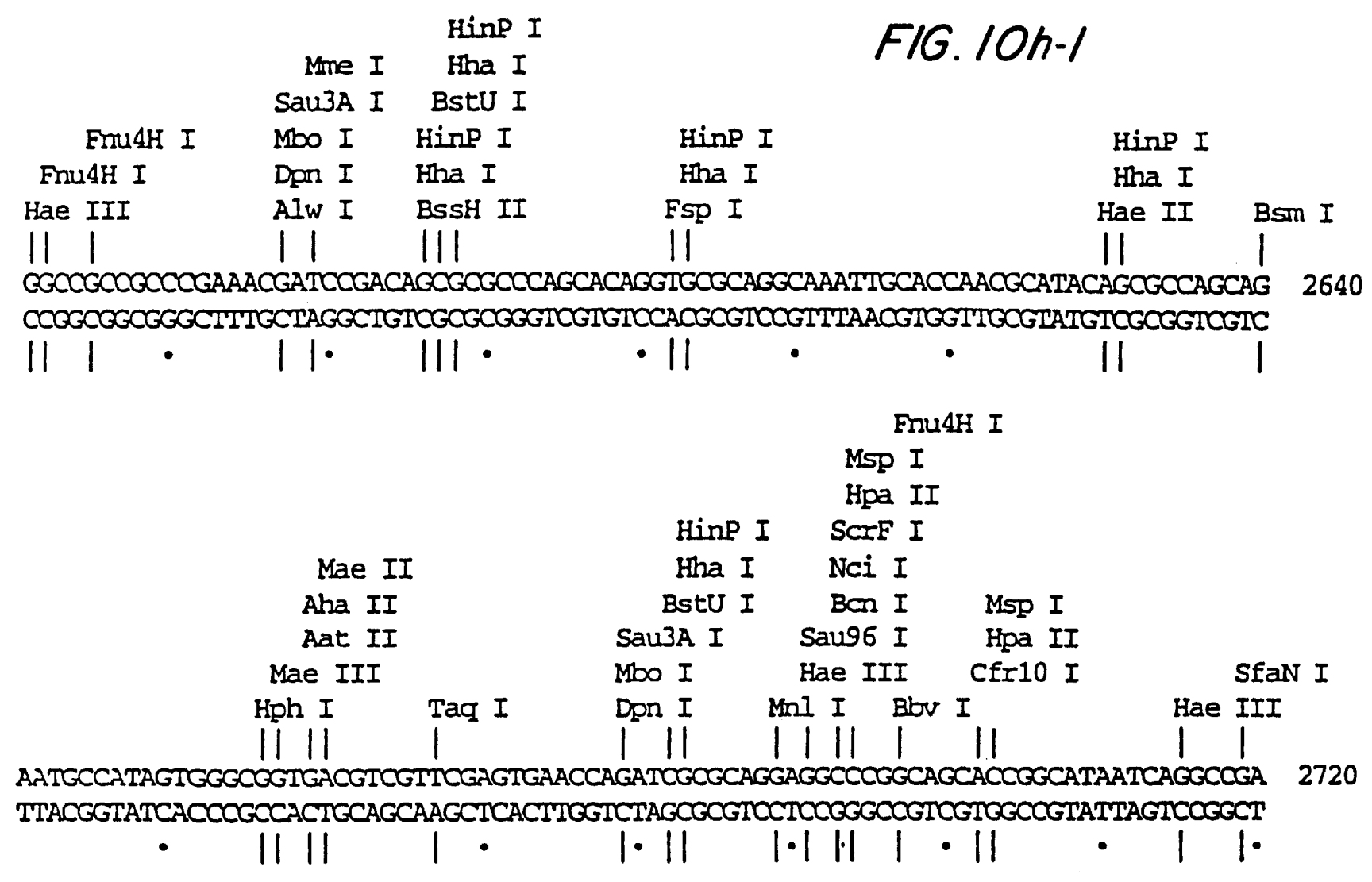
Figure 10H-2:
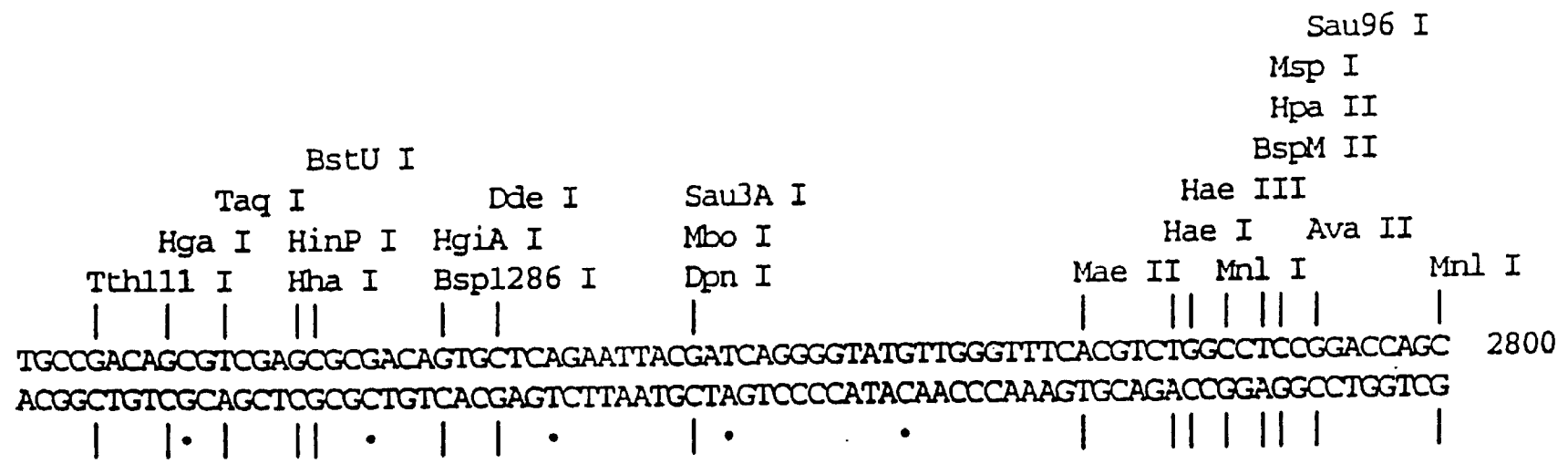
Figure 10I-1:
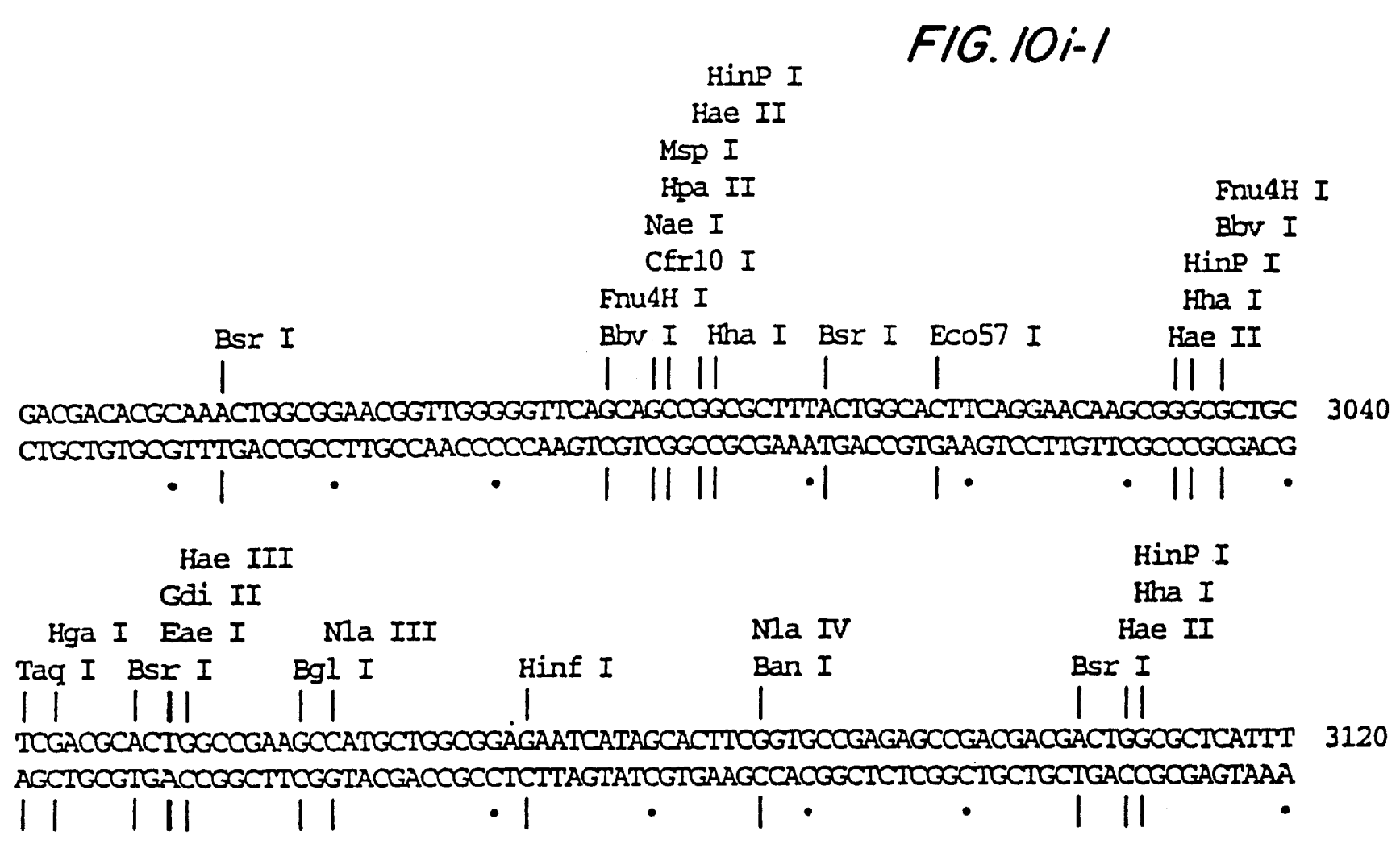
Figure 10I-2:
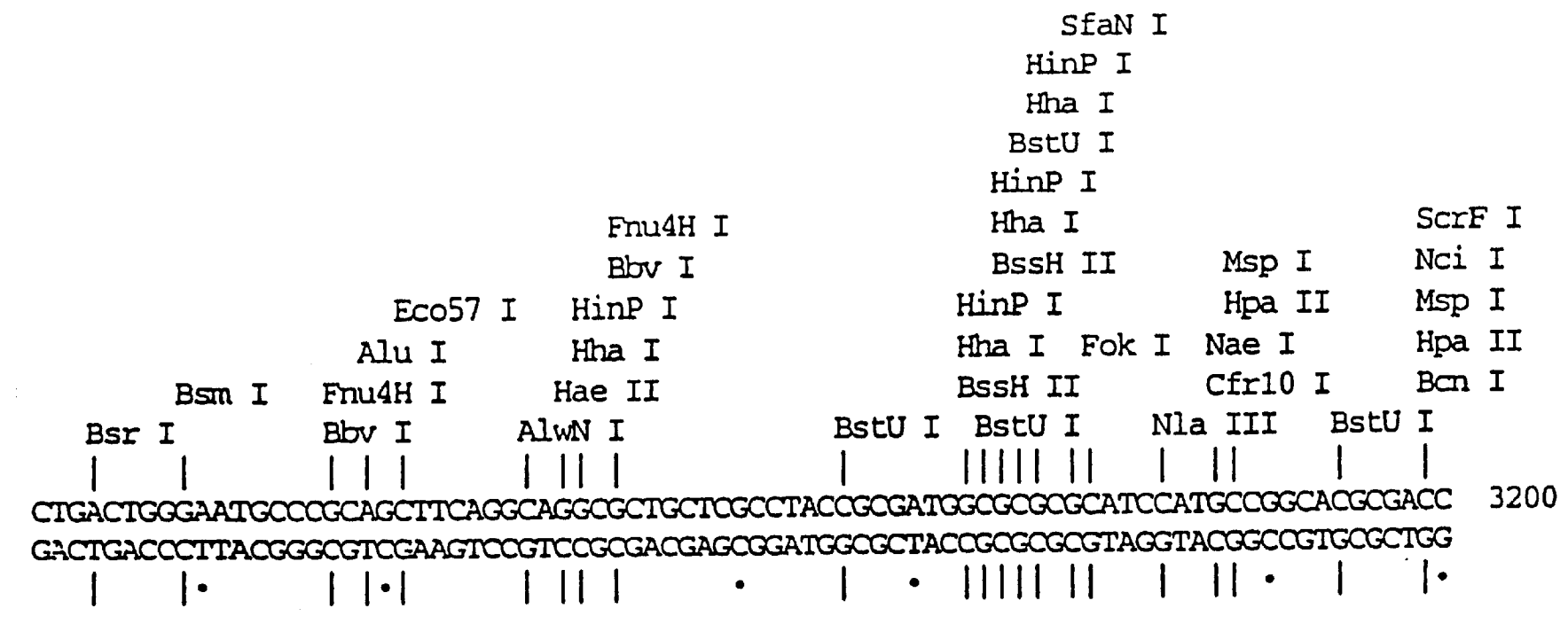
Figure 10J-1:
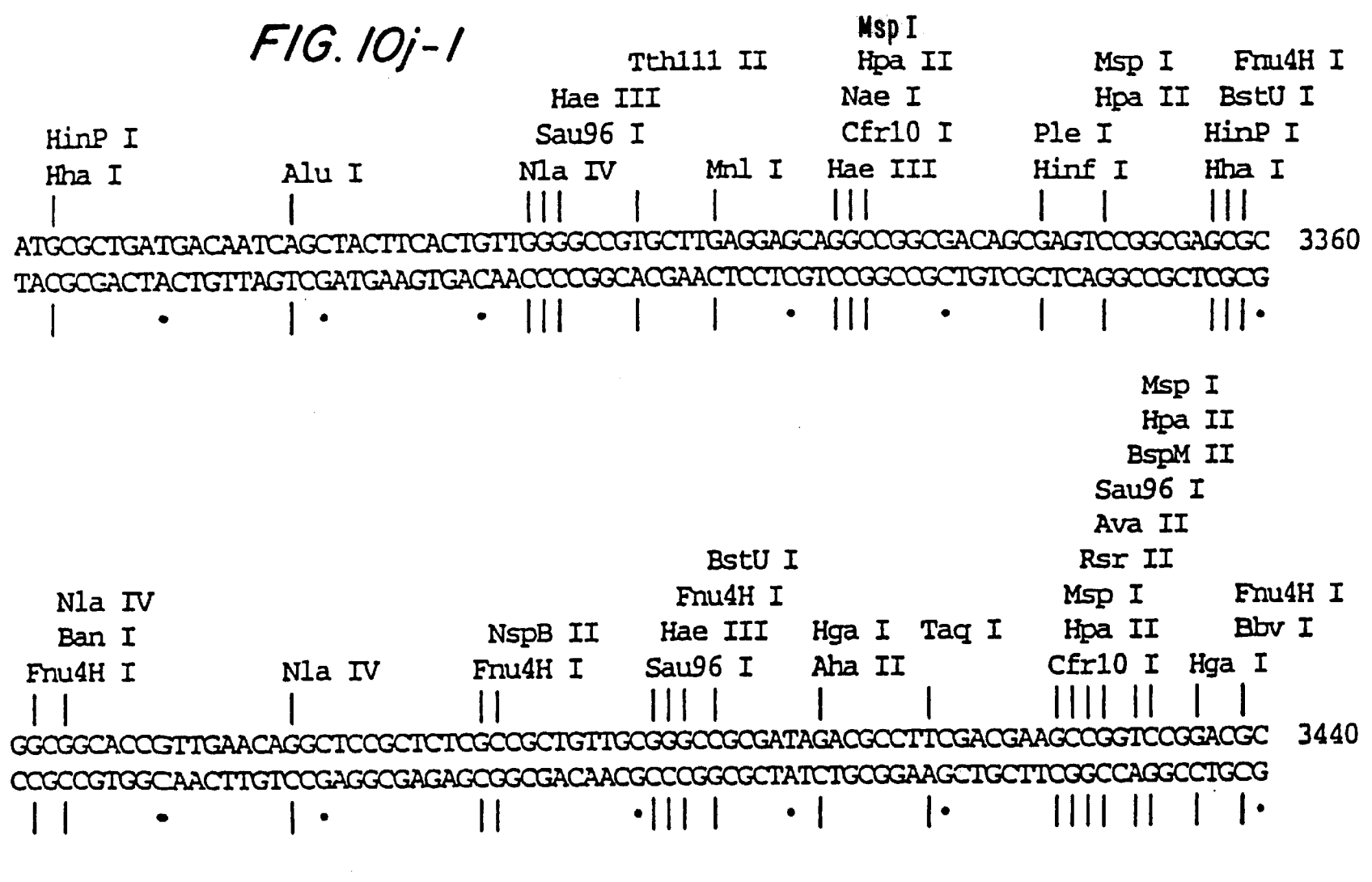
Figure 10K-1:
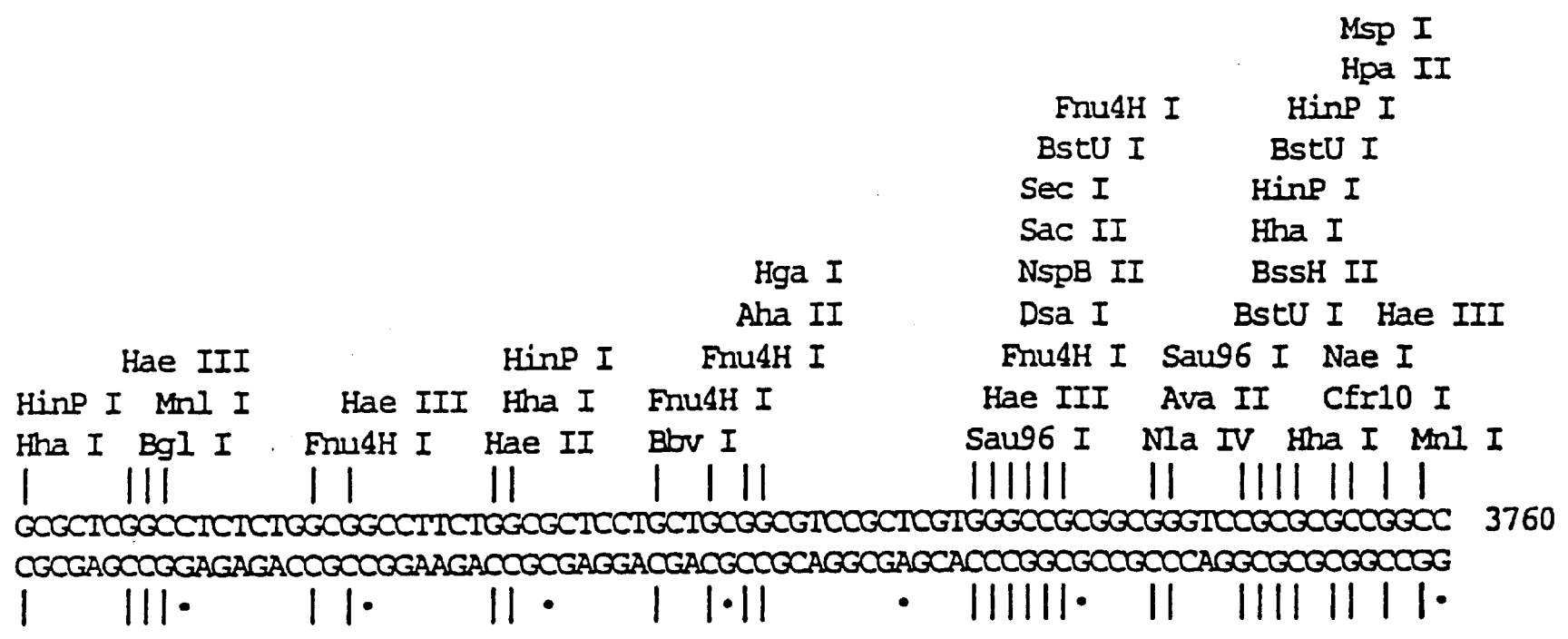

FIGS. 10A–M show the nucleotide sequence of pLMT8.5 SEQ ID NO.1 and the positions of restriction endonuclease sites;

FIGS. 11A–F show a tabulation of the restriction sites in the sequence of pLMT8.5 and the length of the restriction fragment produced;

FIGS. 14 and 15 show construction of pPLT4 and sequence containing lead of T7 SEQ ID NO. 2.

DETAILED DESCRIPTION OF THE INVENTION

Figure 1:
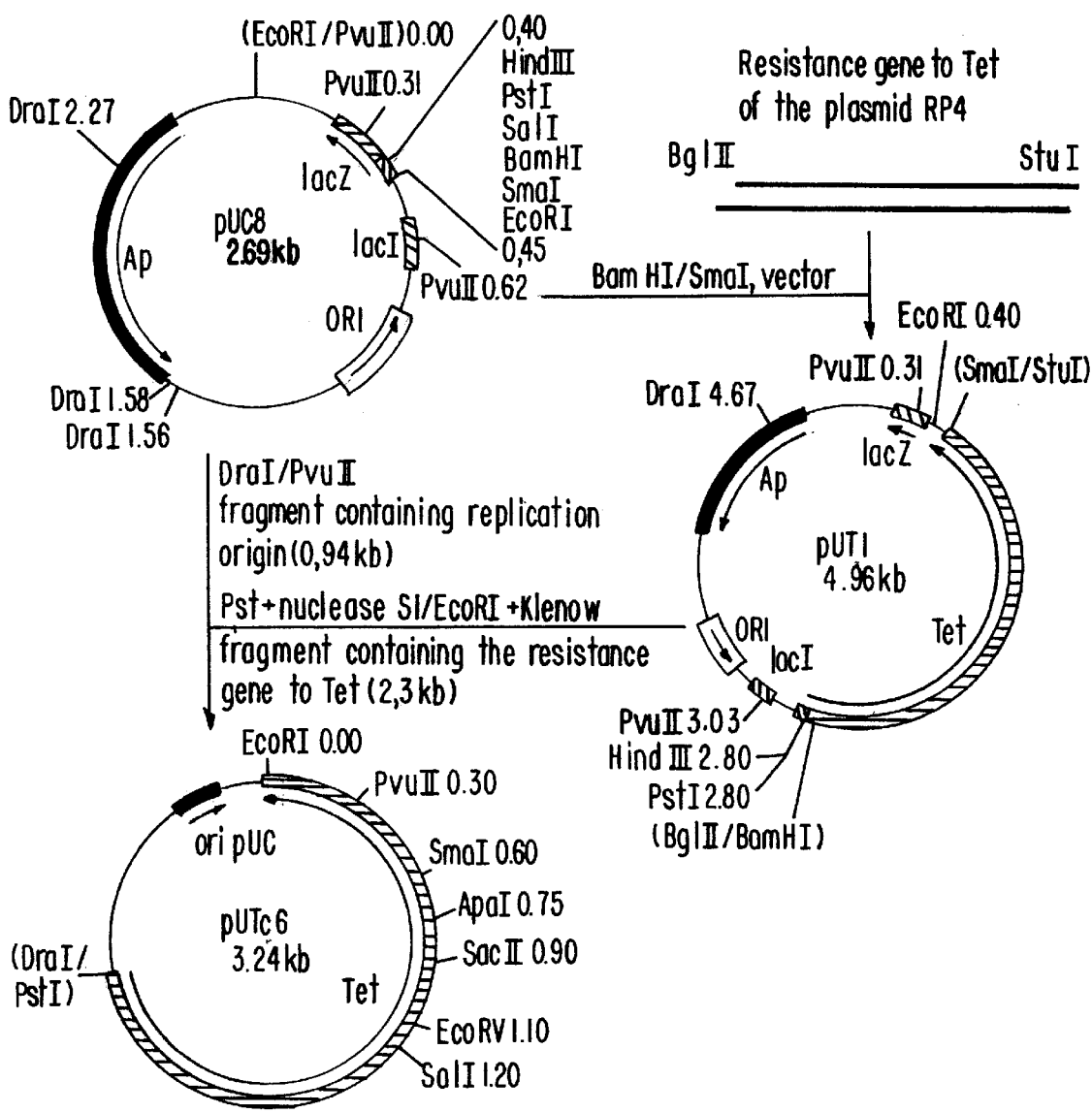
FIG. 1 shows a construction of the plasmid pUTc6 containing the gene of tetracycline resistance of plasmid pRP4 and the origin of replication pUC8 with only one EcoRI cloning site.

The present invention provides various embodiments, including at least one of: a vector comprising at least one nucleic acid such as DNA for cloning of a nucleic acid or for expression of at least one heterologous protein by a cell such as gram negative bacteria (the vector can comprise a nucleic acid molecule, e.g., DNA, encoding: an origin of replication region, optionally and preferably a selection marker (which can be a coding nucleic acid in a restriction site), a promoter, an initiation region e.g. a translation initiation region and/or a ribosome binding site, at least one restriction site for insertion of heterologous nucleic acid, e.g., DNA, encoding the heterologous protein, and a transcription terminator); a method for extracting a recombinant protein from within a cell such as a recombinant Gram negative bacteria having a cell membrane; and, a method for purifying an isolated recombinant human insulin. Without limiting the general nature of the foregoing, the following provides a discussion of various embodiments, in detail.

In an embodiment, the present invention relates to a method for permeabilization of a cell membrane of a cell such as a recombinant Gram negative bacteria, to extract a protein such as a recombinant protein, from within the cell membrane.

Heterologous proteins are proteins which are normally either not produced by a host cell, or those which are normally produced only in limited amounts. The advent of recombinant DNA technology and other standard genetic manipulations, such as point mutagenesis, has enabled the production of heterologous proteins in copious amounts from transfected host cell cultures.

In practice, these heterologous proteins are frequently produced by genetic expression in quantities that involve precipitation under conditions which maintain the solubility of host cellular proteins.

The present invention is directed to procedures for producing heterologous proteins and to methods of isolating and purifying heterologous proteins having minimal contamination by endotoxins.

The present invention further relates to a method of producing proteins by recombinant DNA technology. The invention relates to: a multi-purpose vector for expressing at least one heterologous protein in cells such as E. coli or other gram negative bacteria; methods for producing such vectors; a method for extracting protein from a cell, such as a recombinant protein from bacteria, without lysing the cell or bacteria; and a method for purifying isolated recombinant protein.

Recombinant DNA technology has enabled the expression of foreign (heterologous) proteins in microbial and other host cells. In this process, a vector containing genetic material directing a host cell to produce a protein encoded by a portion of a heterologous DNA sequence is introduced into the host, and the transformed host cells can be fermented and subjected to conditions which facilitate the expression of the heterologous DNA, leading to the formation of large quantities of the desired protein.

Plasmids are extensively used as vectors to clone DNA molecules. Most plasmid vectors are made by taking DNA from a variety of replicons (plasmids, bacteriophage chromosomes and bacterial chromosomes) and joining the DNA together (using restriction enzymes and DNA ligase) to form a plasmid which has an origin of replication, a selection marker (usually an antibiotic-resistance gene) and a promoter for expressing genes of interest in the required host cell.

In the present invention, DNA encoding a protein such as a precursor protein is inserted into a vector. The coding sequence to be expressed is inserted in the correct relationship to a host-specific promoter and other transcriptional regulatory sequences and in the correct reading frame, so that the heterologous protein is produced. The vector also contains sequences for efficient translation (e.g., the Shine-Dalgarno Region for expression in bacterial cells). Expression vectors usually contain a transcription termination site 3' to the inserted gene to ensure the mRNA produced to avoid run on through the plasmid.

In a preferred embodiment, the expression vector of the present invention, denoted pLMT8.5, contains the following:

i. Origin of replication, preferably of pUC8 (which insures a high copy number of the plasmid in the E. coli recipient cells);

ii. A marker, preferably a tetracycline resistance marker from plasmid pRP4;

iii. A promoter, preferably a $P_L$ promoter isolated from bacteriophage lambda;

iv. Shine-Dalgarno regions, preferably synthetic Shine-Dalgarno regions, and preferably such synthetic regions from T7 phage gene 10;

v. A transcription terminator such as synthetic efficient transcription terminator which is Rho-independent; and vi. At least one restriction site, and preferably a region of multiple restriction sites to facilitate the cloning of the genes to be expressed.

The construction of the plasmid pLMT8.5 is illustrated in FIGS. 1–5, and FIGS. 10A–M and 11A–F show the nucleotide sequence and restriction sites in pLMT8.5.

Into the at least one restriction site can be cloned at least one nucleotide sequence which can be exogenous, e.g., encoding an epitope of interest, a biological response modulator, a growth factor, a recognition sequence, a therapeutic gene, a fusion protein or other protein of interest (e.g., proinsulin) or combinations thereof. With respect to these terms, reference is made to the following discussion, and generally to Kendrew, THE ENCYCLOPEDIA OF MOLECULAR BIOLOGY (Blackwell Science Ltd., 1995) and Sambrook, Fritsch and Maniatis, *Molecular Cloning, A Laboratory Manual,* 2nd Ed., Cold Spring Harbor Laboratory Press, 1982.

An epitope of interest is an immunologically relevant region of an antigen or immunogen or immunologically active fragment thereof, e.g., from a pathogen or toxin of veterinary or human interest.

An epitope of interest can be prepared from an antigen of a pathogen or toxin, e.g., an antigen of a human pathogen or toxin, or from another antigen or toxin which elicits a response with respect to the pathogen, or from another antigen or toxin which elicits a response with respect to the pathogen, such as, for instance: a Morbillivirus antigen, e.g., a canine distemper virus or measles or rinderpest antigen such as HA or F; a rabies glycoprotein, e.g., rabies glycoprotein G; influenza antigen, e.g., influenza virus HA or N or an avian influenza antigen, e.g., turkey influenza HA, Chicken/Pennsylvania/1/83 influenza antigen such as a nucleoprotein (NP); a bovine leukemia virus antigen, e.g., gp51, 30 envelope; a Newcastle Disease Virus (NDV) antigen, e.g., HN or F; a feline leukemia virus antigen (FeLV), e.g., FeLV envelope protein; RAV-1 env; matrix and/or preplomer of infectious bronchitis virus; a Herpesvirus glycoprotein, e.g., a glycoprotein from feline herpesvirus, equine herpesvirus, bovine herpesvirus, pseudorabies virus, canine herpesvirus, HSV, Marek's Disease Virus, Epstein-Barr or cytomegalovirus; a flavivirus antigen, e.g., a Japanese encephalitis virus (JEV) antigen, a Yellow Fever antigen, or a Dengue virus antigen; a malaria (Plasmodium) antigen, an immunodeficiency virus antigen, e.g., a feline immunodeficiency virus (FIV) antigen or a simian immunodeficiency virus (SIV) antigen or a human immunodeficiency virus antigen (HIV); a parvovirus antigen, e.g., canine parvovirus; an equine influenza antigen; an poxvirus antigen, e.g., an ectromelia antigen, a canarypox virus antigen or a fowlpox virus antigen; an infectious bursal disease virus antigen, e.g., VP2, VP3, VP4; a Hepatitis virus antigen, e.g., HBsAg; a Hantaan virus antigen; a C. tetani antigen; a mumps antigen; a pneumococcal antigen, e.g., PspA; a Borrelia antigen, e.g., OspA, OspB, OspC of Borrelia associated with Lyme disease such as *Borrelia burgdorferi, Borrelia afzelli* and *Borrelia garinii;* or a chicken pox (varicella zoster) antigen.

Of course, the foregoing list is intended as exemplary, as the epitope of interest can be derived from any antigen of any veterinary or human pathogen; and, to obtain an epitope of interest, one can express an antigen of any veterinary or human pathogen. Nucleic acid molecules encoding epitopes of interest such as those listed can be found in the patent and scientific literature such that no undue experimentation is required to practice the claimed invention with respect to any exogenous DNA encoding at least one epitope of interest.

Since the heterologous DNA can be for a growth factor or therapeutic gene, reference is made to U.S. Pat. No. 5,252,479, which is incorporated herein by reference, together with the documents cited in it and on its face, and to WO 94/16716, each of which is also incorporated herein by reference, together with the documents cited therein (see Kendrew, supra, especially at page 455 et seq.). The growth factor or therapeutic gene, for example, can encode a disease-fighting protein, a molecule for treating cancer, a tumor suppressor, a cytokine, a tumor associated antigen, or interferon; and, the growth factor or therapeutic gene can, for example, be selected from the group consisting of a gene encoding alpha-globin, beta-globin, gamma-globin, granulocyte macrophage-colony stimulating factor, tumor necrosis factor, an interleukin, macrophage colony stimulating factor, granulocyte colony stimulating factor, erythropoietin, mast cell growth factor, tumor suppressor p53, retinoblastoma, interferon, melanoma associated antigen or B7. U.S. Pat. No. 5,252,479 provides a list of proteins which can be expressed in an adenovirus system for gene therapy, and the skilled artisan is directed to that disclosure. WO 94/16716 provide genes for cytokines and tumor associated antigens and the skilled artisan is directed to that disclosure.

As to epitopes of interest, one skilled in the art can determine an epitope or immunodominant region of a peptide or polypeptide and ergo the coding DNA therefor from the knowledge of the amino acid and corresponding DNA sequences of the peptide or polypeptide, as well as from the nature of particular amino acids (e.g., size, charge, etc.) and the codon dictionary, without undue experimentation. See also Ivan Roitt, *Essential Immunology,* 1988; Kendrew, supra; Janis Kuby, *Immunology* (1992), pp. 79–80; Bocchia, M. et al, Specific Binding of Leukemia Oncogene Fusion Protein Peptides to HLA Class I Molecules, Blood 85:2680–2684; Englehard, VH, Structure of peptides associated with class I and class II MHC molecules Ann. Rev. Immunol. 12:181 (1994)); Gefter et al., U.S. Pat. No. 5,019,384, issued May 28, 1991, and the documents it cites, incorporated herein by reference (Note especially the "Relevant Literature" section of this patent, and column 13 of this patent which discloses that: "A large number of epitopes have been defined for a wide variety of organisms of interest. Of particular interest are those epitopes to which neutralizing antibodies are directed. Disclosures of such epitopes are in many of the references cited in the Relevant Literature section.")

With respect to expression of a biological response modulator, reference is made to Wohlstadter, "Selection Methods," WO 93/19170, published Sep. 30, 1993, and the documents cited therein, incorporated herein by reference.

With respect to expression of fusion proteins by inventive vectors, reference is made to Sambrook, Fritsch, Maniatis, *Molecular Cloning, A LABORATORY MANUAL* (2d Edition, Cold Spring Harbor Laboratory Press, 1989) (especially Volume 3), and Kendrew, supra, incorporated herein by reference. The teachings of Sambrook et al., can be suitably modified, without undue experimentation, from this disclosure, for the skilled artisan to generate recombinants or vectors expressing fusion proteins.

Thus, one skilled in the art can create recombinants or vectors expressing a growth factor or therapeutic gene and use the recombinants or vectors, from this disclosure and the knowledge in the art, without undue experimentation.

Moreover, from the foregoing and the knowledge in the art, no undue experimentation is required for the skilled artisan to construct an inventive vector which expresses an epitope of interest, a biological response modulator, a growth factor, a recognition sequence, a therapeutic gene, or a fusion protein or any protein of interest such as pro-insulin; or for the skilled artisan to use an expression product from an inventive vector.

Figure 12:
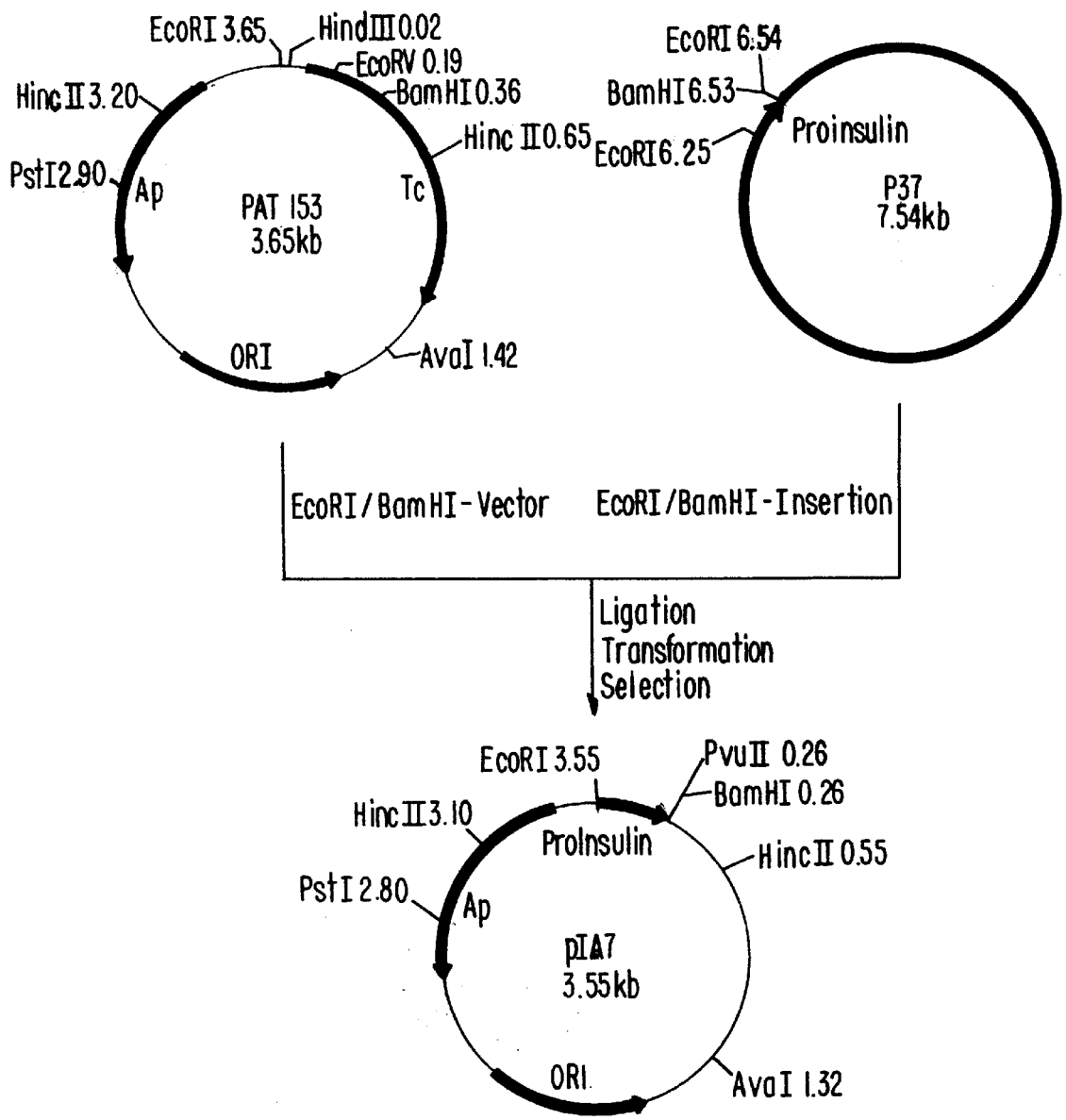
FIGS. 12 and 13 show the strategy for obtaining a fragment from pLA7 containing the pro-insulin sequence and a histidine tag and inserting them into the restriction site of the multiple cloning sites of vector plasmid pLMT8.5 to yield vector plasmid pHIS.
Figure 13:
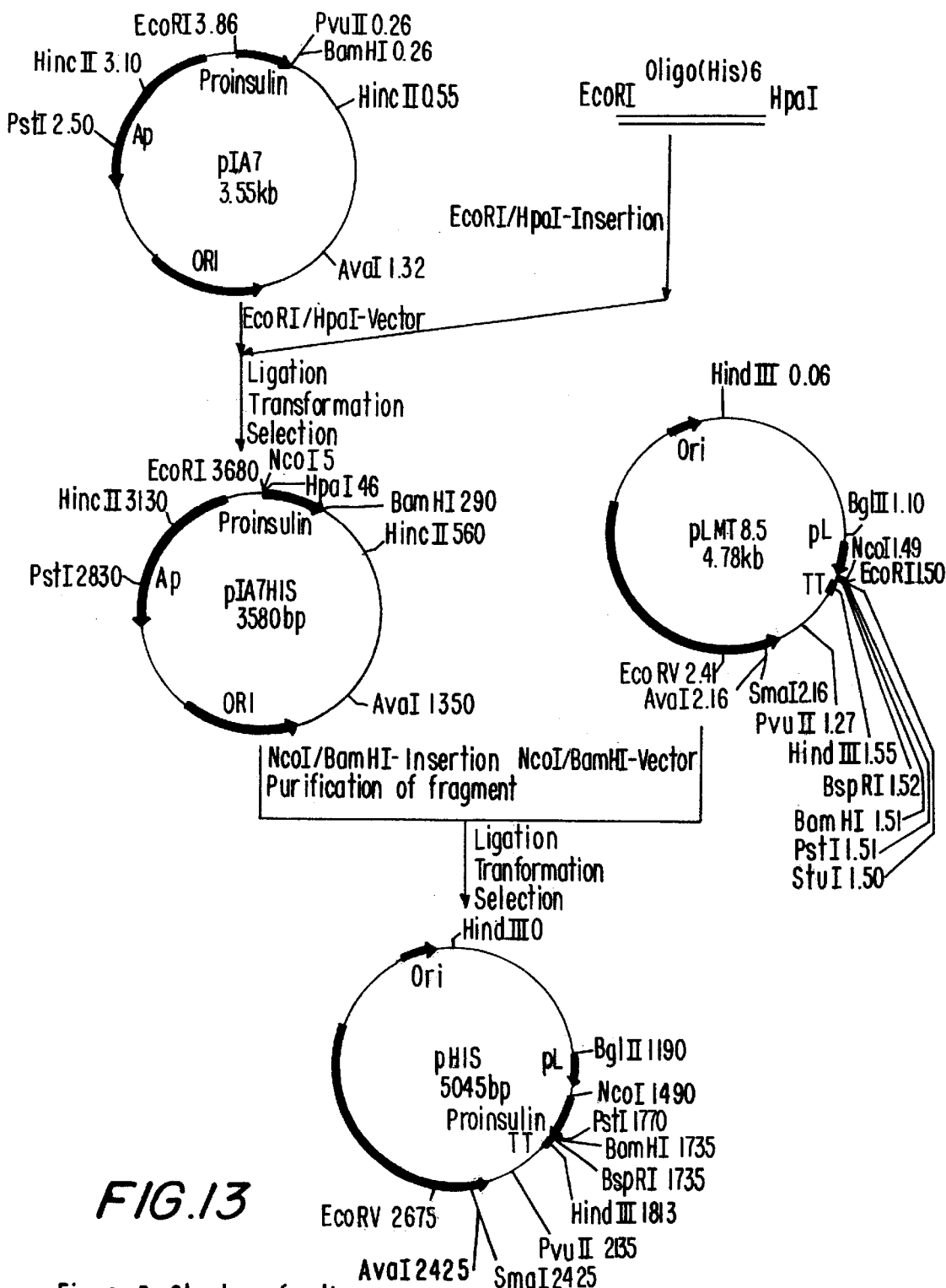
Figure 14:
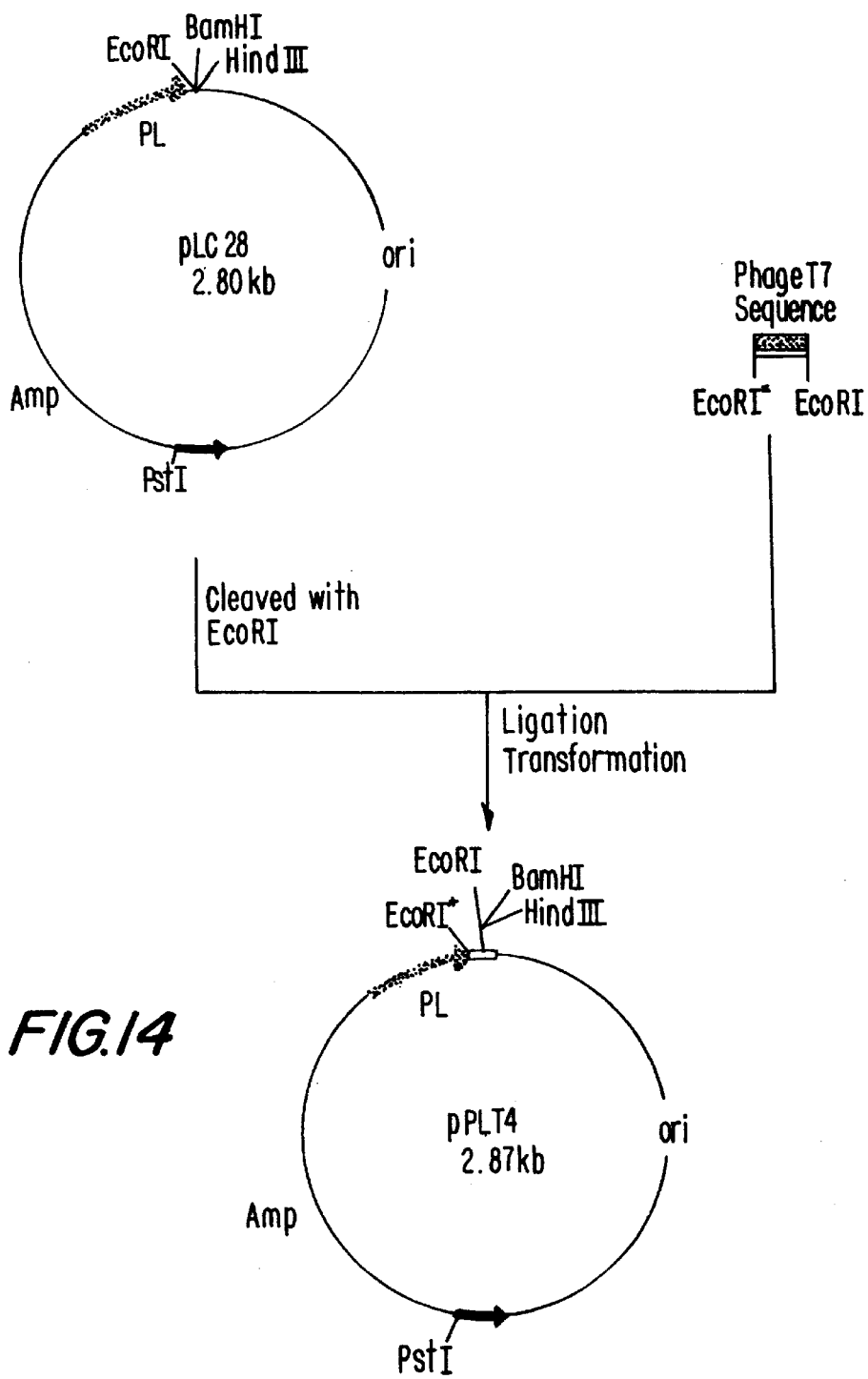

Further preferred embodiments of the invention include plasmid vectors containing a nucleic acid molecule (inserted into a restriction site) encoding pro-insulin and pro-insulin with a His tag, e.g., plasmids pPTAl and pHIS (which are akin to pLMT8.5, but contain DNA encoding pro-insulin and pro-insulin with a His tag in a restriction site; see FIGS. 12 and 13). The pro-insulin with a His tag is useful for isolation of the pro-insulin (see Example 7).

The stability of the protein can be a limiting factor in the expression of its gene in *E. coli,* which is affected by many factors, including the presence or absence of proteolytic enzymes in the medium, as well as the sequence of the protein itself.

The formation of inclusion bodies of the produced recombinant protein can facilitate protection against proteolysis. The inclusion bodies are produced depending on the protein, and can have certain advantages if one wants to induce proteins which are insoluble or which are toxic for *E. coli* (Schein, 1989; Kane & Hartley, 1988; Hellebust et al., 1989). Generally, they are formed as cytoplasmatic aggregates which can be purified after lesion of the cell followed by centrifugation and mixing the proteins with a strong denaturant, e.g. urea or guanidine.

With regard to the stability of the induced protein as it is affected by the protein sequence, the half-life of a protein should also be considered in relation to its amino-terminal residue, also known as N-end rule. Tobias et al. (1991) confirm the existence of this rule in *E. coli.* The residues arginine, lysine, leucine, phenylalanine, tyrosine and tryptophan at the amino terminus, tend to decrease the half-life of the protein, i.e., the half life can be on the order of two minutes, whereas other residues provide proteins having a half-life of more than ten hours for the same protein. The amino acids arginine and leucine act as secondary destabilizing residues because their activity depends on conjugation with the primary destabilizing residues, leucine and phenylalanine, through the transference protein-tRNA-phenylalanine/leucine (transferase L/F). This enzyme, which is present in Gram-negative bacteria and absent in eukaryotes, catalyzes the conjugation of leucine and phenylalanine in N-arginine ends and lysine sterically accessible in proteins or peptides. The protease Clp(Ti), one of the two known ATP dependent proteases in *E. coli* (the other one is La), is needed for degradation in vivo of N-end rule substrates. Clp (750 kd) is a protein containing two subunits, ClpA (21 Kda) and ClpP (21 Kda), being comparable to the 20 S proteasomes of the eukaryotes. Even though the mutations clpA⁻ of *E. coli* lose the standard of the N-end rule, they grow at the rate of the wild *E. coli*, showing normal phenotypes and not stablizing various short-life proteins of *E. coli* (Varshavsky, 1992).

Another way to form a more stable, heterologous protein in *E. coli* is by producing it as a protein that fuses with a part of native/natural protein of the bacteria. Some of the heterologous proteins are rapidly degenerated by the protease of the host and genetic fusion stabilizes the produced protein within the cell, also providing a strategy for later purification (Sherwood, 1991). One example of this method is the addition of a region, rich in arginine at the carboxyl-end of urogastrone, that aids in the protection against proteolysis and in the purification of the protein in an ion-exchange column (Smith et al., 1984).

The present invention provides an alternative method for the development of stable, isolatable, heterologous proteins, which method overcomes the above-identified problems associated with the stability of the induced protein.

The present invention provides a method to improve the expression of the heterologous proteins, by employing a vector for expression, the plasmid pLMT8.5 and derivatives thereof, e.g., pPTA1 and pHIS, which are strong enough to result in a rate of protein production higher than the degradation rate.

The present invention provides a process for constructing a vector for expression of heterologous proteins, preferably low molecular weight proteins, e.g., less than 10 Kda, in *E. coli*.

The present invention provides a highly efficient process for thermo-regulated production of heterologous proteins in *E. coli* and in other Gram-negative bacteria, preferably for the production of human pro-insulin.

The method of the present invention for thermo-regulated highly efficient production of heterologous proteins in *E. coli* and other Gram-negative bacteria, includes thermal induction of a culture of bacteria containing the plasmid pLMT8.5 and the gene for cloning, in which the plasmid pLMT8.5 is prepared according to the process described herein and the cloning is achieved without genetic fusion. In a preferred embodiment, the heterologous protein is human pro-insulin from the synthetic gene for pro-insulin.

Recombinant *E. coli* cells almost always express the heterologous protein in the form of insoluble cytoplasmic inclusion bodies. In other words, the recombinant protein is not excreted into the culture media. An additional characteristic of recombinant *E. coli* is the accumulation of high amounts of acetate in the media, mainly during the induction phase. The deleterious effect of acetate accumulation (>5 g/L) on cell growth and recombinant protein expression is well documented in the literature.

Additionally, with regard to the accumulation of high concentrations of acetate in the media, which is a general consequence of working with *E. coli*, the present invention facilitates the development of fermentation conditions, wherein both high biomass accumulation (>70 g/dry weight/L) and maintenance of low acetate concentration (<2.0 g/L) are achieved, while the production of a increased concentration of expressed recombinant protein is obtained.

With regard to the method outlined herein for the purification of protein isolated from inclusion bodies, it will be understood that minor modifications in the purification protocol may be made without departing from the spirit or scope of the invention, i.e., specifically in regard to the choice of solvents, buffers, detergents, denaturants, proteolytic enzymes, separation methods and chromatographic media. It will be understood from the disclosure that while the preferred detergent for use in the method of the present invention is Triton X-100, one of ordinary skill in the art may employ any such nonionic detergent in practicing the instant invention. Similarly, with regard to the choice of proteolytic enzymes, while trypsin and carboxypeptidase B are preferred, one may substitute any appropriate proteolytic enzyme, e.g., the substitution of Endoproteinase Lys-C for trypsin, in order to convert pro-insulin to insulin, and such a substitution is well within the gambit of knowledge of the skilled artisan acquainted with available proteolytic enzyme preparations and their respective specificities.

A better understanding of the present invention and of its many advantages will be had from the following non-limiting Examples, given by way of illustration.

EXAMPLES

Example 1

Vector Preparation

The inventive process for the construction of a vector for use in thermo-regulated production of heterologous proteins in *E coli*, and the construction of an inventive vector of the invention was comprised of the following stages:

i. Construction of plasmid pULTDK7.1 (FIG. 1)

The construction of pULTDK7.1 was initiated by the isolation of the fragment containing the promoter $P_L$ of the phage lambda. This fragment extends from the HindIII site to the HpaI site of the phage and was cloned into the HindIII and SmaI sites of the polylinker of pUC19, forming the recombinant plasmid pUCPL2.7. Oligonucleotides 011929 and 011930, which contain the Shine-Dalgarno region of the gene 10 of the phage T7, were annealed and ligated to the EcoRI site of pUCPL2.7, forming plasmid pULT7.2.4. Plasmid pULT7.2.4 was cleaved at the BspEI and XbaI sites, treated with DNA polymerase I fragment Klenow and relegated, resulting in a deletion of the coding region of the gene N of the phage lambda and formation of plasmid pULTDK7.1.

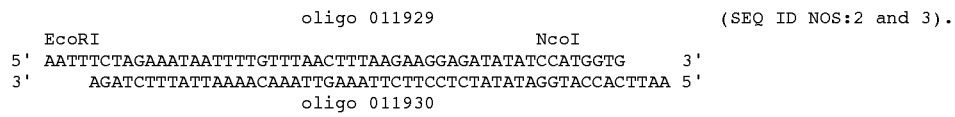

Figure 2:
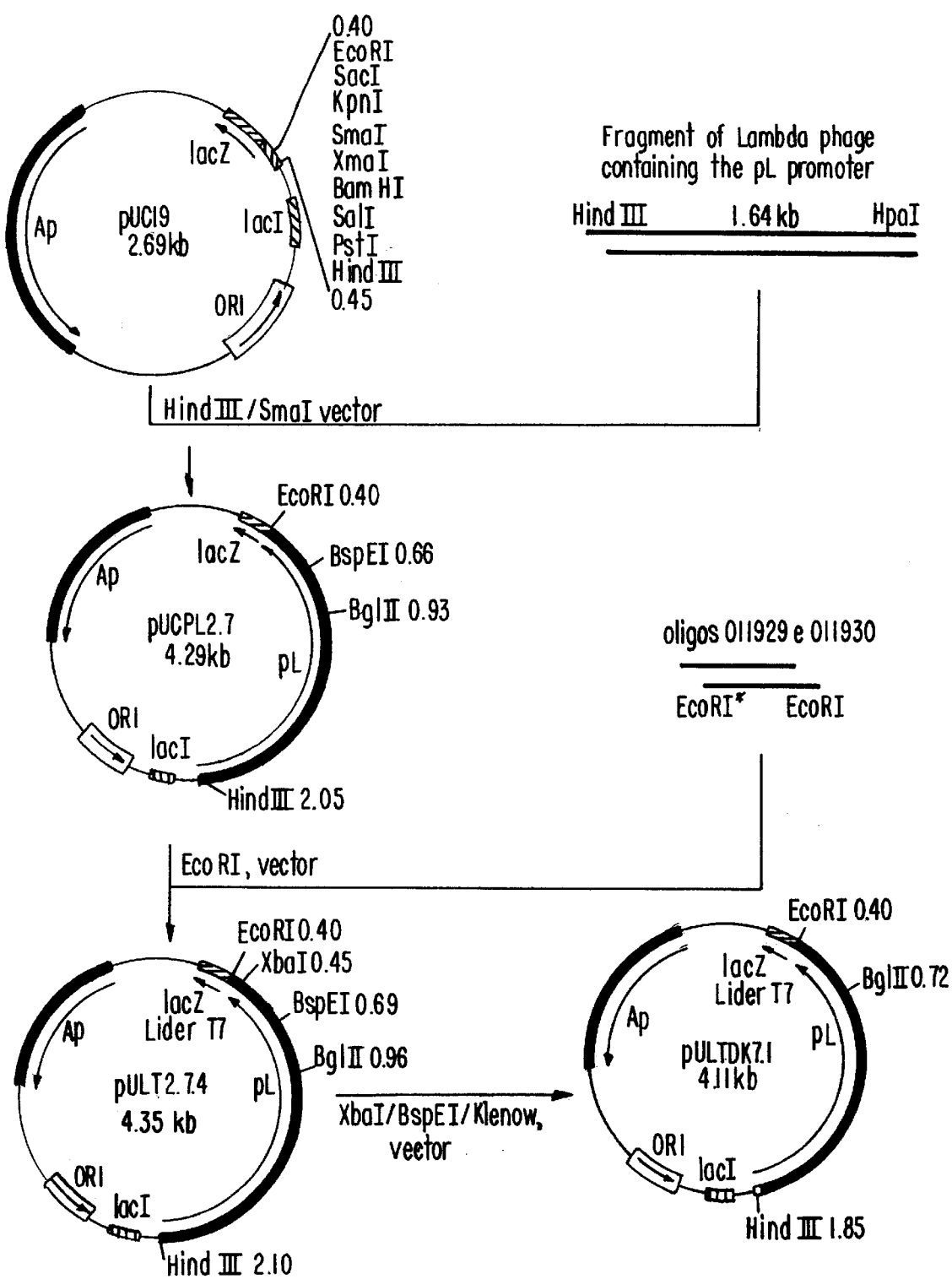
FIG. 2 shows a construction of plasmid pULTDK 7.1 containing the $P_L$ promoter of phage lambda and the Shine-Dalgarno region of gene 10 of phage T7.

```
                        oligo 011929                          (SEQ ID NOS:2 and 3).
       EcoRI                                   NcoI
    5' AATTTCTAGAAATAATTTTGTTTAACTTTAAGAAGGAGATATATCCATGGTG      3'
    3'     AGATCTTTATTAAAACAAATTGAAATTCTTCCTCTATATAGGTACCACTTAA 5'
                             oligo 011930
``` ii. Construction of Plasmid pUTC6 (FIG. 2)

Figure 3:
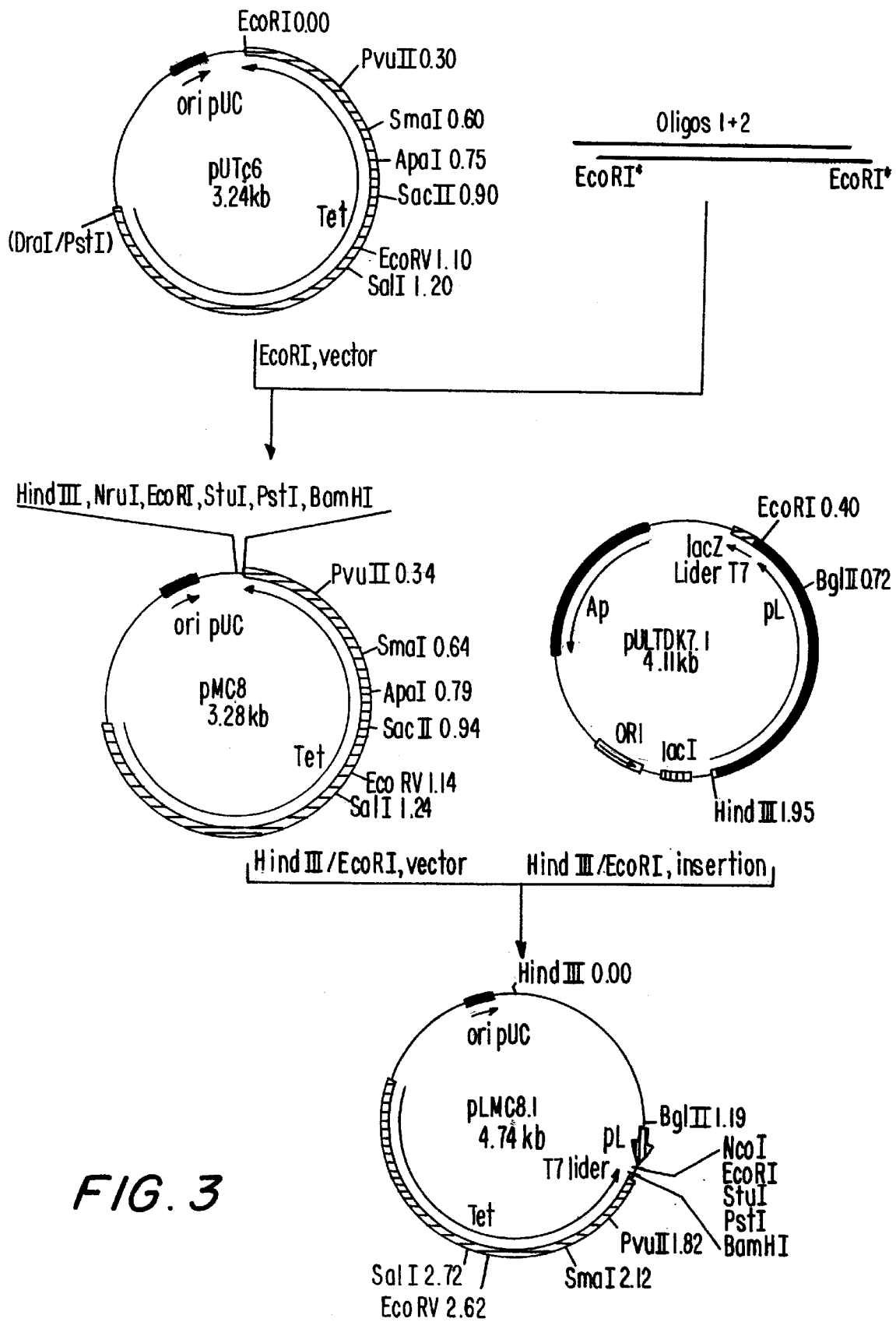
FIG. 3 shows a polylinker addition in pUTC6 and subsequent cloning of the fragment containing the Pl promoter and Shine-Dalgarno region of plasmid pULTDK 7.1 and a construction of pLMC 8.1.

The construction of pUTC6 began by the isolation of the gene for resistance to tetracycline (Tc), by means of digestion of the plasmid pRP4 with BGlII and StuI, which liberated a fragment of 1.4 kb, which was cloned in the BamHI and SmaI sites of plasmid pUC8, forming plasmid pUT1. A 0.9 kb pUC8 fragment was liberated by digestion with DraI and PvuII and ligated to pUT1 after digestion with PstI, treatment with S1 nuclease, digested with EcoRI and treated with Klenow, to obtain the plasmid pUTC6, which maintains the site EcoRI and contains the origin of replication and the gene for resistance to Tc.

iii. Construction of Plasmid pLMC8.1 (FIG. 3)

Figure 4:
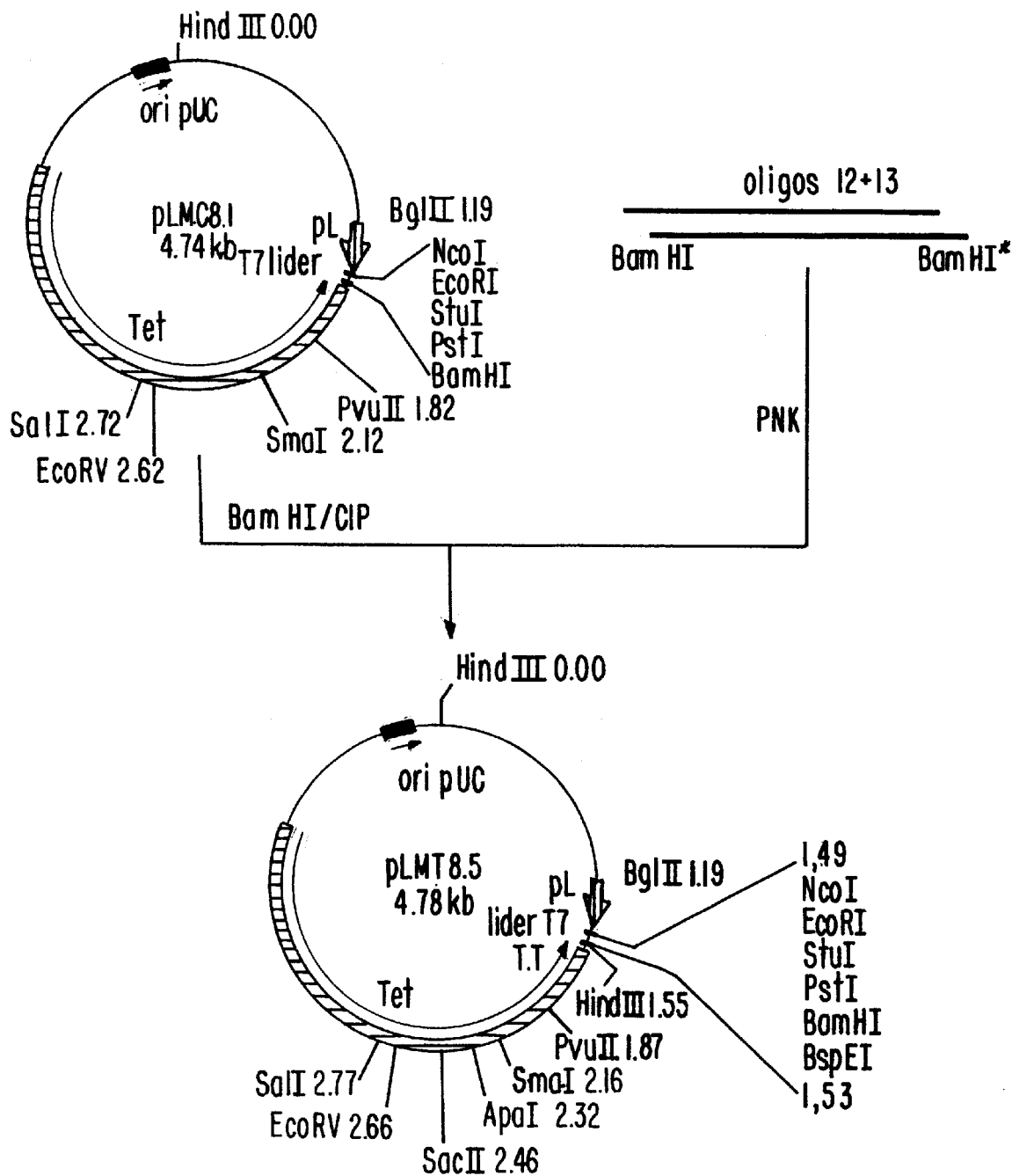
FIG. 4 shows a final construction of hyperexpression vector pLMT8.5 by addition of the synthetic transcription terminator in pLMC8.1.
Figure 5:
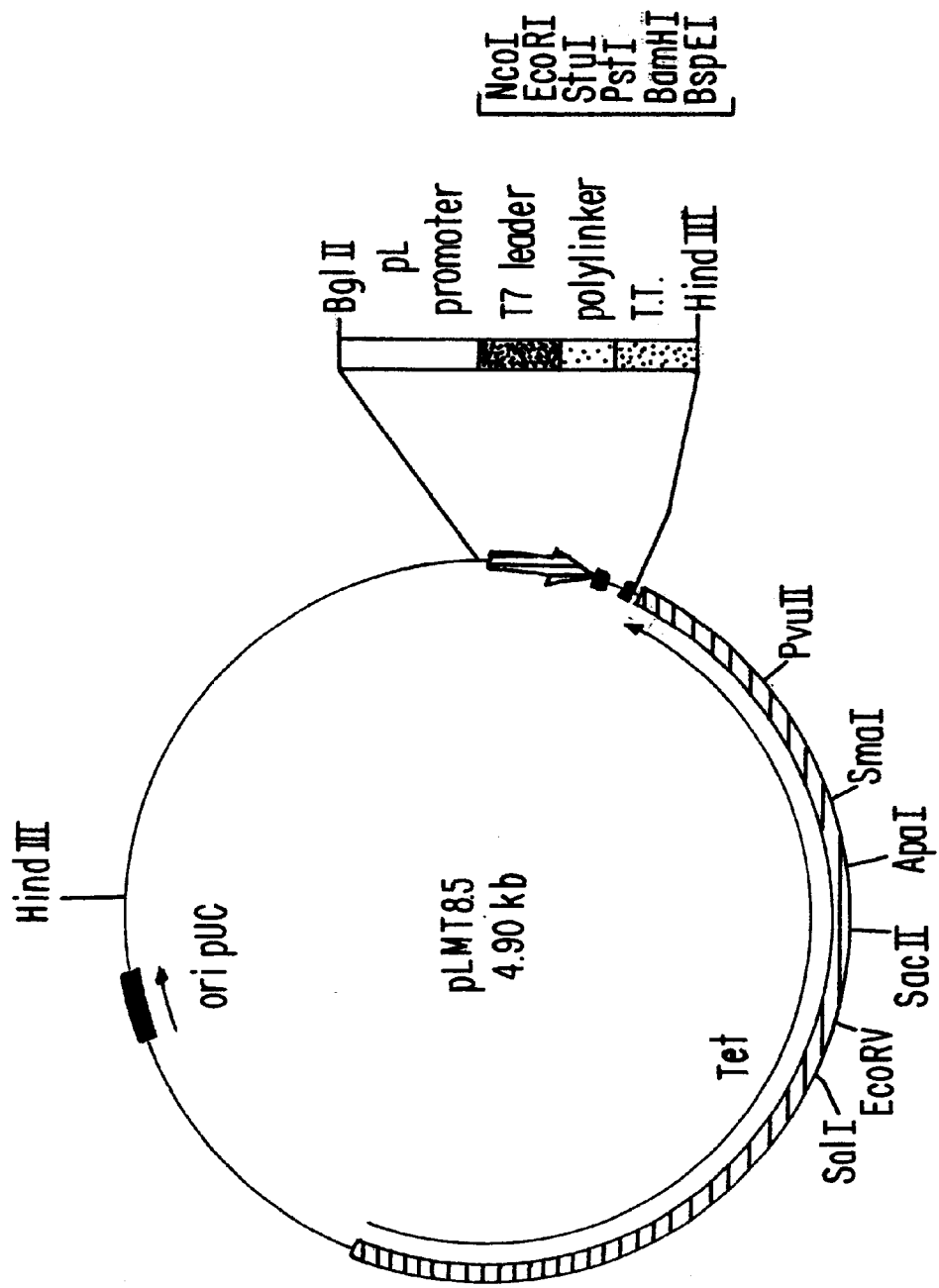

Annealed oligonucleotides 1 and 2 were ligated to the EcoRI site of pUTC6 to form the plasmid pMC8, containing a region of restriction sites for molecular cloning. Subsequently, pULTDK7.1 was liberated by digestion with the HindIII and EcoRI and ligated to pMC8, also digested with HindIII and EcoRI, to yield the recombinant plasmid pLMC8.1, containing the gene for resistance to Tc, the origin of replication, the promoter $P_L$, the Shine-Dalgarno region and a polylinker for molecular cloning.

iv. Construction of Plasmid pLMT8.5 (FIG. 4)

An efficient transcription-terminator was inserted from oligonucleotides 12 and 13 which were annealed and ligated to the BamHI site of the plasmid pLMC8.1, preserving the site at the 5' end of the oligonucleotides and creating a HindIII site at the 3' end, yielding the expression vector pLMT8.5 for *E. coli* and other gram-negative bacteria.

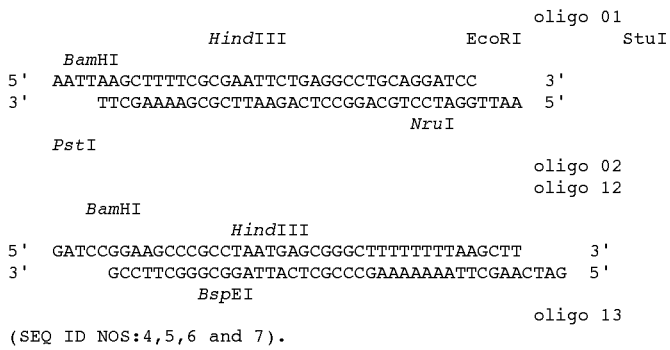

(SEQ ID NOS:4,5,6 and 7).

Hence, pLMT8.5, prepared according to the method described hereinabove, contains: (1) origin of replication of pUC8; (2) the gene for resistance to tetracycline of pRP4; (3) the promoter Pl of the Lambda phage; (4) the SD-region of the gene 10 of the phage T7; (5) multiple cloning sites for cloning without fusion; and (6) Rho-independent terminator of transcription (See FIGS. 1–5, 10A–M, 11A–F).

To obtain a vector expressing pro-insulin, coding DNA therefor was inserted into a restriction site of the multiple cloning sites of vector plasmid pLMT8.5. In particular, the synthetic gene for proinsulin was cloned on a polylinker yielding vector plasmid pPTA1 (pLMT8.5 +proinsulin). The vector was then inserted into *E. coli* and cultures thereof were grown for expression of pro-insulin (e.g., N4830-1 (cI$^{857}$) strain; see Examples below).

v. Construction of plasmids pLA7 and pHIS

A fragment from pLA7 containing the pro-insulin sequence and a histidine tag was inserted into the restriction site of the multiple cloning sites of vector plasmid pLMT8.5 yielding vector plasmid pHIS. The cloning strategy is depicted in FIGS. 12 and 13. The vector was then inserted into *E. coli* and cultures thereof were grown for expression of pro-insulin (e.g., N4830-1 (cI$^{857}$) strain; see Examples below). pHIS contains the pro-insulin gene with the oligo encoding a (HIS)6 insertion (Met-Ala-His-His-His-His-His-His-Met-Gly-Arg).

(The synthetic gene for proinsulin, constructed by inventors, using oligonucleotides was, cloned into the NcoI and BamHI sites in the polylinker region of pLMT8.5 vector to make the pPTA1 and pHIS proinsulin expression vector, see Example 8.)

Example 2

High Biomass Formation with Low Acetate Accumulation

Experimental results showed that programmed additions of yeast extract were necessary for high biomass formation. To maintain the acetate concentration at low levels, the pH of the fermentation was controlled automatically via a glucose loop. Under these conditions not only could the pH be controlled at any desirable value (e.g. 6.8 or lower), but also the glucose level in the fermentation broth could be maintained at very low levels (<0.10 g/L) throughout the fermentation, precluding the accumulation of acetate.

Under these conditions dry cell weights of up to 95 g/L and expression of 194 mg of fusion protein per gram of dry cell weight were obtained.

Example 3

Permeabilization and Solubilization of Inclusion Bodies Containing Pro-Insulin

As a rule, inclusion bodies are recovered from the host organism by two procedures: (a) Mechanical or physical rupture of the cell envelope by passing the cell paste through a Manton-Gaulin press or by grinding the cell suspension in a colloidal mill such as a Dyno-Mill; and (b) Digestion of the cell envelope by treatment with lysozyme. However, both of the above-identified techniques are costly, and potentially detrimental to the overall yield of the desired protein.

Hence, the method of the present invention employs alternative methods for the purification and direct solubilization of inclusion bodies.

*E. coli* cells (K-12 strain N 4830-1 containing the pro-insulin gene under the control of the $P_L$ promoter; plasmids pPTA1 and pHIS, see Example 1) were grown in 10 liters of medium containing yeast extract (20 g/L), peptone (6.0 g/L), NaCl (5.0 g/L), glucose (10.0 g/L), Antifoam A (2.0 g/L), and ampicillin (100 ug/ml), pH 6.8 (after sterilization). The medium was inoculated at 10% volume with a pre-culture prepared from an isolated colony grown overnight in the same medium. At an optical density of approximately 6.0 at 540 nm, synthesis of pro-insulin was induced by raising the temperature from 30 to 38° C. Induction could also be initiated at temperatures of 40 to 42° C. Cells were harvested after 2 to 5 hours of induction. Inclusion body formation was monitored by phase contrast microscopy.

The cells were harvested by centrifugation, resuspended twice in deionized water, and recovered by centrifugation. Known amounts of wet cell cake were resuspended in 0.1M Tris-Hcl, pH 8.5, and appropriate amounts of permeabilization compounds, alone, or in combination, were added to a concentration of up to ten times the volume of the weight of the wet cell cake, as shown in Table 1. After overnight agitation at room temperature, the cells were recovered by centrifugation, wet weight of the cell cakes and the wet pellet were homogenized in 10 times their weight of 0.1M Tris-Hcl, pH 8.5 containing 8M urea, and agitation was continued at room temperature for up to 24 hours. Supernatants were recovered by centrifugation, and cell pellets were washed by centrifugation. Fusion protein concentrations were determined by SDS-PAGE analysis using both the supernatant and pellets after the washing step. Weight determinations made on the wet pellets prior to the pretreatment step, after pretreatment, and after 8M urea treatment showed that a substantial weight loss took place, shown in Table 1.

TABLE 1

Effect of some pre-treatments on the weight loss of the cell pellets

| Samples n° | Buffers | Wet Cell Weight | | % Weight Loss | |
|---|---|---|---|---|---|
| | | Initial | After Pre-treatment | After Pre-treatment | After Pre-treat. + 8M urea |
| 1 | Tris 0.1M pH 8.5 | 6.43 | 4.94 | 23.2 | 42.3 |
| 2 | Tris 0.1M pH 8.5/ Toluene | 6.49 | 4.57 | 29.6 | 52.2 |
| 3 | Tris 0.1M pH 8.5/ EDTA | 6.38 | 4.28 | 33.0 | 71.0 |
| 4 | Tris 0.1M pH 8.5/ Triton X-100 | 6.41 | 3.47 | 45.8 | 58.7 |
| 5 | Tris 0.1M pH 8.5/ Toluene/Triton | 6.26 | 3.73 | 40.4 | 58.5 |
| 6 | Tris 0.1M pH 8.5/Toluene/EDTA | 6.38 | 3.81 | 40.3 | 84.6 |
| 7 | Tris 0.1M pH 8.5/EDTA/Triton | 6.47 | 2.21 | 65.8 | 86.3 |
| 8 | Tris 0.1M pH 8.5/Toluene/EDTA/ Triton | 6.38 | 3.58 | 43.9 | 81.7 |

Example 4
Concomitant Permeabilization and Solubilization of Inclusion Bodies Containing Pro-Insulin In preliminary experiments, the pre-treated cells were cleaned of the cytoplasmic proteins and other contaminating material extracted from the cells (grown as in Example 3), by centrifugation, followed by resuspension of the pre-treated and washed cells in buffer containing 8M urea.

Figure 6:
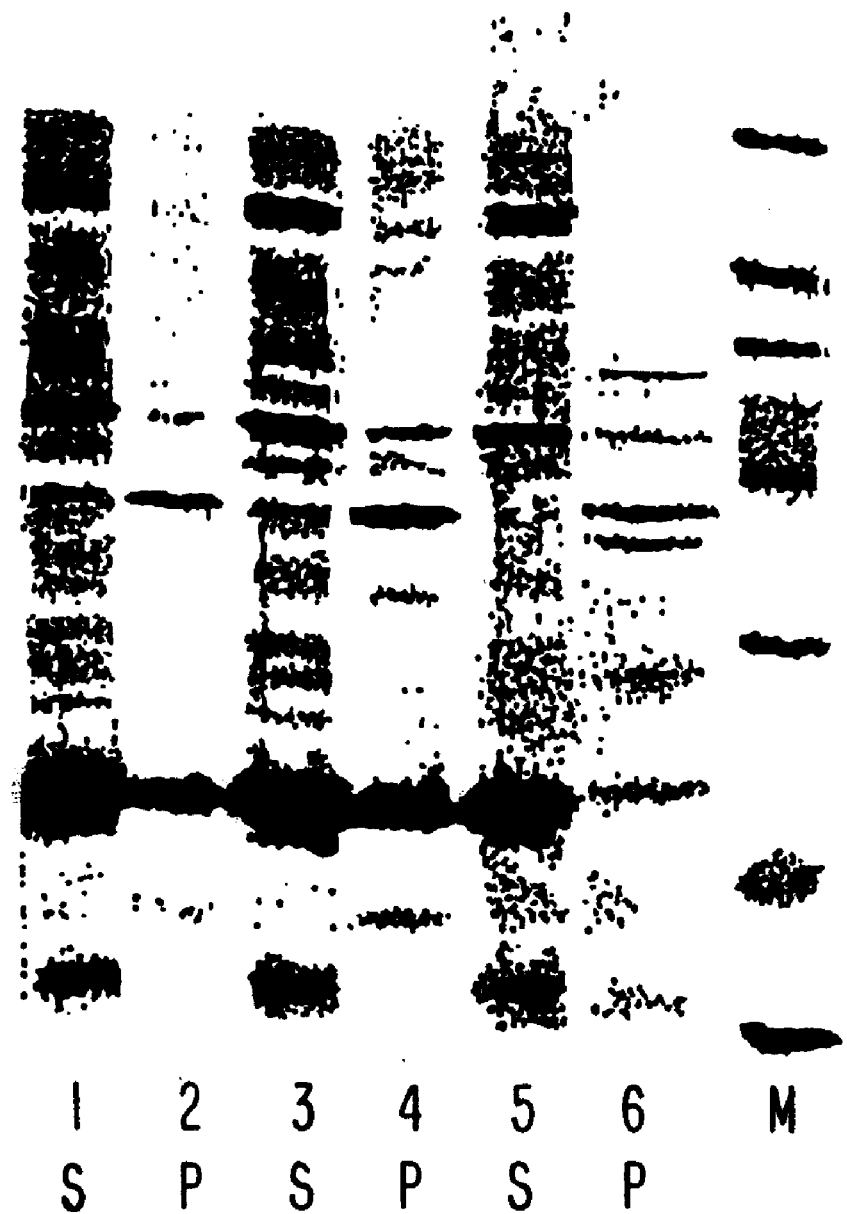
FIG. 6 shows the results of direct inclusion body solubilization of pre-treated cells with 8M urea versus time (lanes 1–2 represent 6 hours of solubilization; lanes 3–4 represent 8 hours of solubilization; and lanes 5–6 represent 24 hours of solubilization wherein M denotes molecular weight marker, S denotes supernatant and P denotes residual pellet)

One liter aliquots of a fermentation broth, prepared as in Example 3, were concentrated to 100 ml by cross flow filtration. Aliquots of the concentrated cell suspension were diafiltered with 10 volumes of 0.1M Tris-Hcl, pH 8.5 buffer containing either 5 Mm EDTA, 1% toluene, or deionized water. Solid urea was added to a final concentration of 8M, and the volume was brought to 200 ml with buffer. Samples taken at different time intervals, up to 24 hours, were analyzed by SDS-PAGE. A highly effective purification and solubilization of the inclusion bodies was obtained in as little as 6 hours of urea treatment, as shown in FIG. 6.

Example 5
Cell Permeabilization Procedure Using 20% Triton X-100

Cell cultures grown as in Example 4 were harvested by centrifugation, resuspended twice in deionized water and recovered by centrifugation. Known amounts of the wet cell cake were resuspended in 0.1M Tris-Hcl, pH 8.5, containing 20% Triton X-100, and the solutions were agitated overnight at room temperature. Fusion protein concentrations were determined by SDS-PAGE analysis, and it was found that under these conditions, a substantial amount of cytoplasmic material diffuses out of the cell, leaving an empty shell containing essentially the inclusion body with few contaminating cellular proteins.

Figure 7:
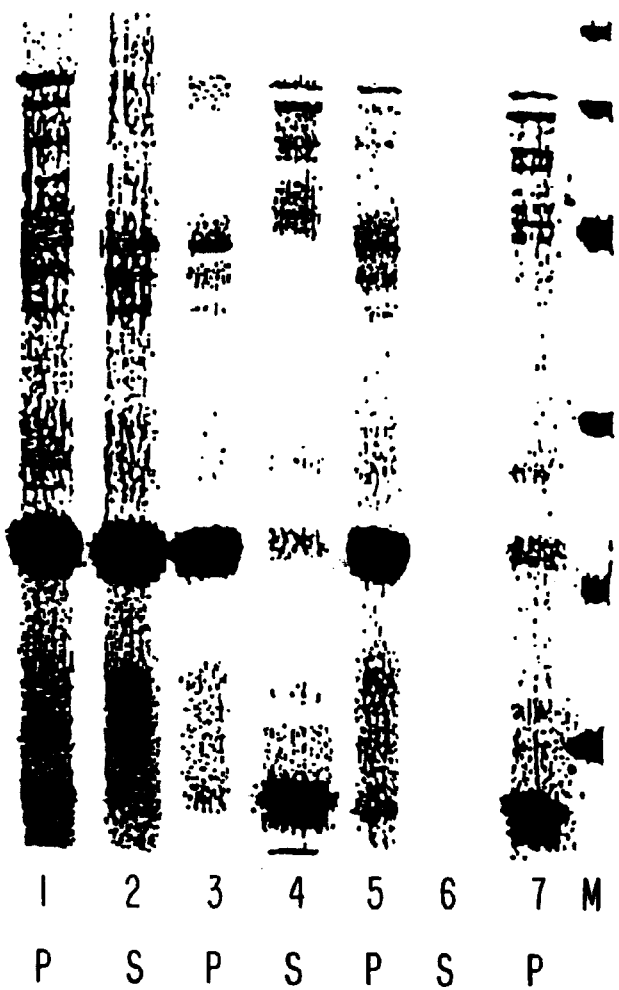
FIG. 7 shows the purification of pro-insulin fusion protein by pH precipitation, wherein aliquots of solubilized (8M urea) and dialyzed fusion protein were precipitated at different pH values (at pH 4.5, all the recombinant protein could be recovered in the precipitate (lane 5); lanes 1 to 7 represent pH values of 5.5, 5.5, 5.0, 5.0, 4.5, 4.5, 4.0 and molecular weight marker, respectively, with P referring to pellet and S referring to supernatant)
Figure 8:
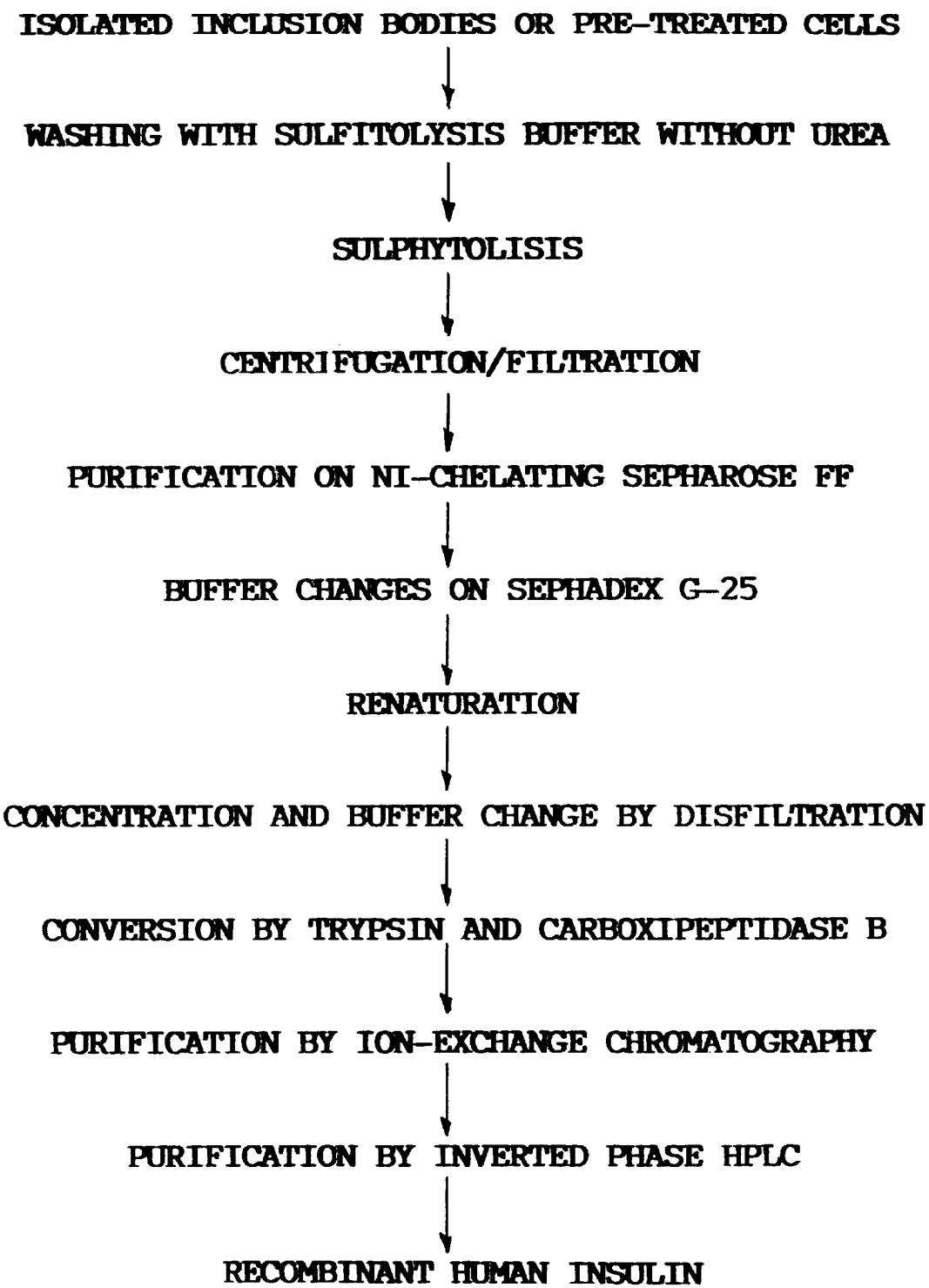
FIG. 8 shows a schematic representation of the inventive process for isolating recombinant human insulin.

Example 6
Purification and Concentration of the Solubilized Inclusion Bodies by pH Precipitation Cell cultures are grown and pre-treated, and the inclusion bodies solubilized as in Examples 3 or 4. The solution of solubilized inclusion bodies was dialyzed, or ultrafiltered, to eliminate urea. A fractional pH precipitation step resulted in the enhanced purity of the solubilized protein. The pH of the protein solution was lowered, either by the addition of mineral acids, i.e., hydrochloride or sulfuric acids, or by organic acids, i.e., acetic acid. The pH was lowered to 6.0 by this method, and the precipitate was removed by centrifugation. The fusion protein was precipitated from the solution by lowering the pH to 5.0 by the same method. A complete recovery of the fusion protein was achieved. The precipitated fusion protein was dissolved in alkaline buffer at pH 8.5. The purification of protein by fractional pH precipitation is shown in FIG. 7.

Example 7
Purification and Isolation of Insulin

The isolated inclusion bodies or whole pre-treated cells from cells containing and expressing plasmid pHIS were washed twice with 50 Mm ammonium acetate buffer, pH 9.0 and centrifuged. The precipitate was dissolved in 50 Mm ammonium acetate buffer, pH 9.0, containing 8M urea, and sodium sulphite (1.25 g/g of sample) and sodium tetrathioate (0.55 g/g of sample) were added. The sample was stirred, at room temperature. The sulfitolysis reaction was monitored by analysis of aliquots on a Mono-Q column. After 24 to 48 hours, the sample was diluted 3 times with deionized water, centrifuged, and the supernatant was filtered to give a clear solution.

The filtered supernatant was applied to a Ni-chelating sepharose FF column (Pharmacia Biotech, Upsala Sweden), equilibrated with 0.1M sodium phosphate, 50 mM NaCl, pH 7.3. The sample was eluted in a stepwise gradient, with the equilibration buffer containing 8M urea and 0.08M imidazole, followed by washing with the equilibration buffer containing 8M urea and 0.3M imidazole. The chromatographic separation was monitored by absorbance measurement at 280 nm. The buffer of the solution containing pure S-sulfonated protein isolated by metal affinity chromatography was changed to 10 Mm glycine, pH 10.0, by gel filtration chromatography on Sephadex G-25.

The pure sulfonated protein was renatured (0.5 mg protein/ml) by the addition of 0.5 mM cystine and 0.5 mM beta-mercaptoethanol, with agitation for 18 to 24 hours at 4 to 8° C., and the reaction was monitored by injection of aliquots of the reaction mixture on HPLC equipped with an Aquapore RP-300 column. The renatured samples were concentrated and the buffer was changed by diafiltration.

To 1.0 ml of renatured sample (8 mg/ml) in 0.1M Tris-Hcl, pH 7.5, containing 0.01M EDTA, was added 35 ug of trypsin and 0.6 ug of carboxypeptidase B. The reaction was monitored by HPLC analysis on an Aquapore RP-300 column, and the reaction was complete after 1 hour at 37° C. The reaction mixture was diluted 3 times with water, and purified by ion-exchange chromatography and reversed-phase HPLC.

Example 8
Test of Efficiency of the Vector of Expression

Figure 9:
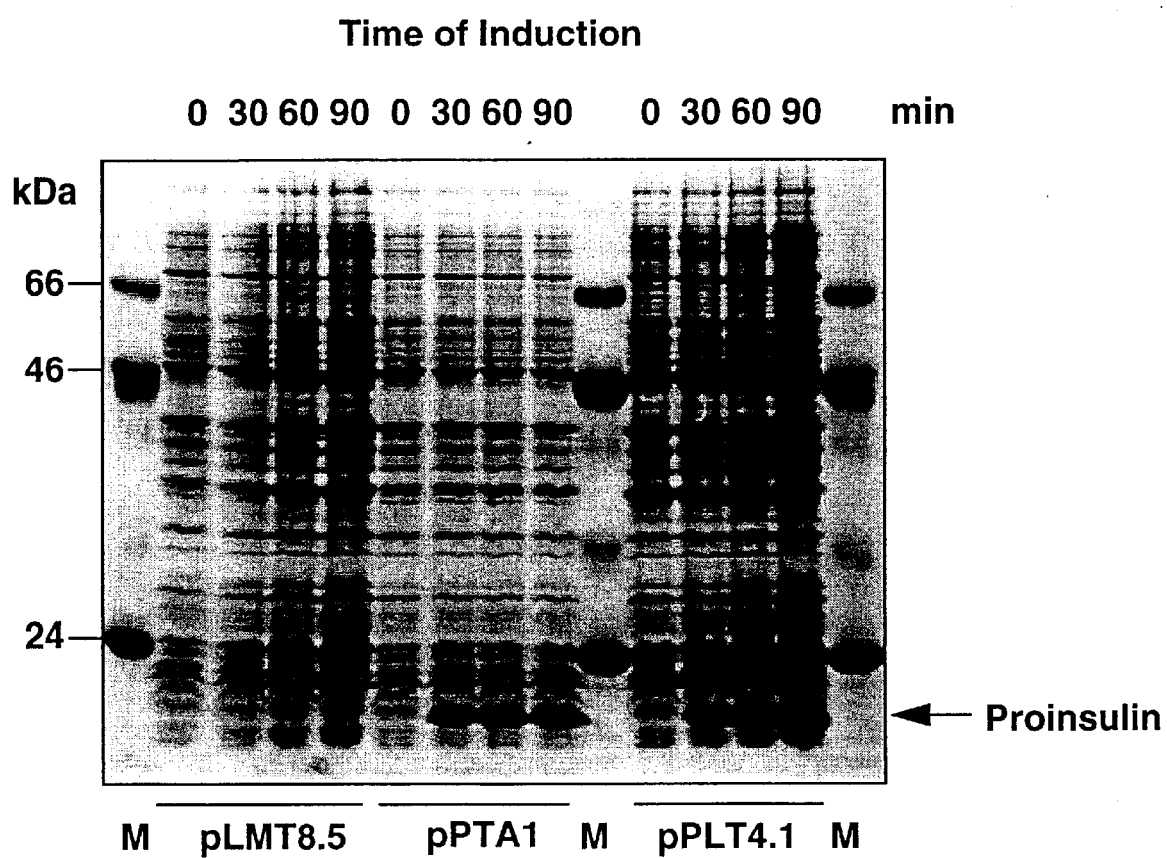
FIG. 9 shows an analysis in a 15% denaturing gel of total cellular protein from cultures transformed with pLMT8.5, pPTA1 or pPLT4.1, at different induction times at 40° C. (the arrow indicates the induced recombinant pro-insulin protein)

A synthetic gene for proinsulin, constructed by inventors, using oligonucleotides was cloned into the NcoI and BamHI sites in the polylinker region of pLMT8.5 vector to make the pPTA1 and pHIS proinsulin expression vectors (see Example 1). In tests it was found that, after thermal induction of a culture of E. coil N4830-1 (cl$^{857}$) strain, containing the plasmid pPTA1 (pLMT8.5 +proinsulin), there was induction of the recombinant protein of approximately 10 Kda, in a fraction of 20% of the total proteins of the bacteria over a period of 90 minutes, and that it loses the capacity to multiply during the thermal shock, leaving it only to the production of the recombinant protein, as shown in FIG. 4. The plasmid pPLT4 was also used in this test. This plasmid is a derivative of the plasmid pPLc28 (Remaut et al., 1981), modified by inventors, in which the same synthetic Shine Dalgarno site and the proinsulin gene of the plasmids pLMT8.5 and pPTA1 were cloned. By comparison with this plasmid, showing an induction of the protein of 11% and cell-growth during the thermal shock, it was found that, over a period of 90 minutes, pLMT8.5 was 100% more efficient (See FIG. 9).

In this manner a hyper-expression-vector for E. coli, denoted pLMT8.5, was obtained. When tested on the production of human proinsulin from the synthetic gene, high levels of protein expression were found to be induced from this gene.

Plasmids pLMT8.5, pPLT4, pHIS, and pPTA1 were deposited on Jun. 24, 1997 with the American Type Culture Collection (ATCC), 12301 Parklawn Drive, Rockville, Md., 20852, USA, under ATCC accession numbers 98474, 98475, 98476 and 98473.

Example 9
Additional Expression Vectors

A gene for any of: an epitope of interest, a biological response modulator, a growth factor, a recognition sequence, a therapeutic gene, a fusion protein or another protein of interest or combinations thereof (as discussed in the Detailed Description) cloned on a polylinker and inserted into plasmid of Example 1, e.g., pLMT8.5, pHIS, and pPTA1; and, plasmids resulting therefrom are inserted into E. coli, e.g., N4830-1 (cl$^{857}$) strain (containing the plasmid pLMT8.5 +gene). After thermal induction there is induction of the recombinant protein akin to that observed in Example 8 showing that pLMT8.5 is extremely efficient.

In this manner a hyper-expression-vector for E. coli, denoted pLMT8.5, is obtained. When tested on the production of human proinsulin from the synthetic gene, high levels of protein expression were found to be induced from this gene; and, high levels of expression are obtainable from using vector plasmid pLMT8.5 and other exogenous genes. As discussed herein, the selection marker can be omitted from pLMT8.5 or derivatives thereof, e.g., pHIS, and pPTA1, and selection can be based on expression of a gene product, e.g., of insulin or of insulin with a His tag. Methods for selection based on expression of an exogenous coding sequence are known in the art and can include immunoprecipitation or other antibody-based screening methods which employ antibodies which bind to the expression product, or selective media with respect to the expression product (see, e.g., U.S. Pat. Nos. 4,769,330, 4,603,112, 5,110,587 regarding selection using selective media with respect to an expression product; U.S. Pat. No. 5,494,807 regarding selection using antibody-based screening methods).

Example 10
Manipulation of Fermentation Conditions to Enhance Protein Expression Productivity of the fermenter could be increased substantially (<40%) by withdrawing approximately 70% of the broth volume, after an induction period at 42° C. for 5 hours, adding fresh media, returning the temperature to 30° C. for an additional 5 hours, followed by an additional 5 hours of induction at 42° C. In this way, without increasing the overall fermentation time (20–22 hrs.), an increased volume of biomass and recombinant protein is obtained.

Thus, alternating 5 hours of fermentation at 30° C. with 5 hours of induction at 42° C., resulted in a higher percentage of recombinant protein expression than when starting the induction after prolonged fermentation (approximately 17 hours) at 30° C.

Heat inactivation was found to negatively influence the inclusion body purification steps due to considerable coagulation of cytoplasmic proteins, at the heat inactivation temperature (80° C.).

Cell inactivation and permeabilization was performed concomitantly by overnight treatment of the harvested cells with 1% Toluene and 50 Mm EDTA. Further purification was achieved by resuspending the recovered biomass in Tris 0.1M, pH 8.5 buffer, containing 1.0% Triton X-100, and agitating for five hours or overnight. Cells pre-treated in this manner, after centrifugation, can be used directly in the ensuing purification steps.

Additionally, by further lysozyme treatment, a suspension of isolated inclusion bodies can be obtained which can be separated from the cell debris by centrifugation, in a highly purified state.

Having thus described in detail preferred embodiments of the present invention, it is to be understood that the invention defined by the appended claims is not to be limited to particular details set forth in the above description as many apparent variations thereof are possible without departing from the spirit or scope of the present invention.

REFERENCES

1. Denhardt, D. T. & Colasanti, J. 1987. A survey of vectors for regulating expression of cloned DNA in E.coli. In Vectors—a survey of molecular cloning vectors and their uses. R. L. Rodrigues and D. T. Denhardt, eds. Butterworth Publishers, Soneham, Mass., U.S.A.
2. Remaut, E.; Stanssens, P. & Fiers, W. 1981. Plasmid vectors for high efficiency expression controlled by the Pl promoter coliphage lambda. Gene, 15:81–93.
3. Mellado R. P. & Salas, M. 1982. High level synthesis in Escherichia coli of the Bacillus subtilis phage Ø29 proteins p3 and p4 under the control of phage lambda PL promoter. Nucl.Acids Res., 10:5773–84.
4. Remault E.; Stanssens, P. & Fiers, W. 1983a. Inducible high level synthesis of mature human fibroblast interferon in Escherichia coli. Nucl. Acids Res., 11:4677–88.
5. Simons, G.; Remaut, E.; Allet, B. Devos, R. & Fiers, W. 1984. High-level expression of human interferon gamma in Escherichia coli under control of the Pl promoter of bacteriophage lambda. Gene, 28:55–64.
6. Remaut, E.; Tsao, H. & Fiers, W. 1983b. Improved plasmid vectors with a thermoinducible expression and temperature-regulated runaway replication. Gene, 22:103–13.
7. Crowl, R.; Seamans, C.; Lomedico, P. & McAndrew, S. 1985. Versatile expression vectors for high-level synthesis of cloned gene products in Escherichia coli. Gene, 38:31–8.
8. Lautenberg, J. A.; Court, D. & Papas, T. S. 1983. High level expression in Escherichia coli of the carboxyterminal sequences of the avian myelocytomatosis virus (MC29) v-myc protein. Gene, 23:75–84.
9. Seth A.; Lapis, P.; Vande Woude, G. F. & Papas, T. 1986. High level expression vectors to synthesize unfused proteins in *Escherichia coli*. Gene, 42:49–57.
10. Cheng X. & Patterson, T. A. 1992. Construction and use of I PL promoter vector for direct cloning and high level expression of PCR amplified DNA coding sequences. Nucl. Acids Res., 20:4591–8.
11. Schauder, B.; Blocker, H.; Frank, R. & McCarthy, J. E. G. 1987. Inducible expression vectors incorporating the *Escherichia coli* atp E translational initiation region. Gene, 52:279–83.
12. Rosenberg, M.; HO, Y. S & Shatzman, A. 1983. The use of pKC30 and its derivatives for controlled expression of genes. Meth. in Enzymol., 101:123–38.
13. Chaconas, G.; Gloor, G. & Miller, J. L., 1985. Amplification and purification of the bacteriophage Mu encoded B transposition protein. J.Biol.Chem., 260:2662–9.
14. Lowman, H. B.; Behm, M.; Brown, S. & Bina, N. 1988. High-level expression of the simian virus 40 genes LP1, VP1 and VP2 as fusion protein in *Escherichia coli*. Gene, 68:23–33.
15. Mott, J. E.; Grant, R. A.; HO, Y. S. & Platt, T. 1985. Maximizing gene expression from plasmid vectors containing the λ PL promoter: strategies for overproducing transcription termination factor p.Proc.Natl.Acad.Sci.USA,82:88–92.
16. Schein, C. H. 1989. Production of soluble recombinant proteins in bacteria. Bio/technology, 7:1141–9.
17. Kane, J. F. & Hartley, D. L. 1988. Formation of recombinant protein inclusion bodies in *Escherichia coli*. Tibtech, 6:95–101.
18. Hellebust, H.; Abrahmsén, L.; Uhlén, M. & Enfors, S. O. 1989. Different approaches to stabilize a recombinant fusion protein. Bio/technology, 7:165–8.
19. Tobias, J. W.; Shrader, T. E.; Rocap, G. & Varshavsky, A. 1991. The N-end rule in bacteria. Science, 254:1374–7.
20. Varshavsky, A. 1992. The N-end rule. Cell, 69:725–35.
21. Smith, J. C.; Derbyshire, R. B.; Cook, E.; Dunthorne, L.; Viney, J.; Brewer, S. J.; Sassenfeld, H. M. & Bell, L. D., 1984. Chemical synthesis and cloning of a poly (arginine)-coding gene fragment designed to aid polypeptide purification. Gene, 32:321–7.

What we claim is:

1. A method of extracting recombinant pro-insulin from within inclusion bodies of a recombinant Gram negative bacteria having a cell membrane, without lysing the bacteria comprising the steps of:
   (a) permeabilizing the cell membrane by contacting the bacteria with a surfactant or permeabilizing agent which separates native cell proteins from the cell membrane without separating the recombinant pro-insulin from the cell, whereby the inclusion bodies remain intact, and a permeabilized cell membrane product is obtained;
   (b) solubilizing the permeabilized cell membrane product comprising the recombinant pro-insulin within the cell, and
   (c) separating the recombinant pro-insulin from the cell.

2. The method of claim 1 wherein the surfactant or permeabilizing agent in step (a) is Triton X-100.

3. The method of claim 1 wherein step (a) includes separating the native cell proteins from the permeabilized cell membrane product by centrifugation and a resultant pellet therefrom contains the recombinant pro-insulin within the cell membrane product.

4. A method for extracting recombinant pro-insulin from within inclusion bodies of a recombinant Gram negative bacteria having a cell membrane, without lysing the bacteria, comprising the steps of:

(a) solubilizing the recombinant pro-insulin with a surfactant or permeabilizing agent, wherein the inclusion bodies remain intact, and wherein a permeabilized cell membrane product is obtained;

(b) extracting the recombinant pro-insulin protein within the cell membrane product with urea, and (c) harvesting the solubilized recombinant pro-insulin protein by centrifugation.

5. The method of claim 4 wherein the surfactant in step (a) is Triton X- 100.

6. The method of claim 4 wherein step (a) includes separating the native cell proteins from the cell membrane by centrifugation and a resultant pellet therefrom contains the recombinant pro-insulin protein within the cell.

7. The method of claim 4 wherein in step (b), the extracting is by contacting the recombinant pro-insulin protein within the cell membrane from step (b) with urea.

8. The method of claim 4 wherein, in step (c), centrifugation provides a resultant supernatant which contains the recombinant pro-insulin protein.

9. The method of claim 1 wherein the recombinant pro-insulin within the recombinant Gram negative bacteria is expressed within the inclusion bodies of the Gram negative bacterial cell.

10. The method of claim 2 wherein the recombinant pro-insulin within the recombinant Gram negative bacteria is expressed within the inclusion bodies of the Gram negative bacterial cell.

11. The method of claim 3 wherein the recombinant pro-insulin within the recombinant Gram negative bacteria is expressed within the inclusion bodies of the Gram negative bacterial cell.

* * * * *